United States Patent [19]

Graham et al.

[11] Patent Number: 5,736,539
[45] Date of Patent: Apr. 7, 1998

[54] INHIBITORS OF FARNESYL-PROTEIN TRANSFERASE

[75] Inventors: Samuel L. Graham, Schwenksville; Theresa M. Williams, Harleysville, both of Pa.

[73] Assignee: Merck & Co., Inc., Rahway, N.J.

[21] Appl. No.: 549,829

[22] PCT Filed: May 19, 1994

[86] PCT No.: PCT/US94/05634

§ 371 Date: Nov. 16, 1995

§ 102(e) Date: Nov. 16, 1995

[87] PCT Pub. No.: WO95/00497

PCT Pub. Date: Jan. 5, 1995

Related U.S. Application Data

[63] Continuation-in-part of Ser. No. 237,586, May 11, 1994, abandoned, which is a continuation-in-part of Ser. No. 80,028, Jun. 18, 1993, abandoned.

[51] Int. Cl.$^6$ .................. A61K 31/495; A61K 31/55; C07D 243/08; C07D 401/00
[52] U.S. Cl. .................. 514/218; 514/252; 514/255; 540/575; 544/361; 544/363; 544/387
[58] Field of Search .................. 514/252, 255, 514/218; 540/575; 544/361, 363, 387

[56] References Cited

U.S. PATENT DOCUMENTS

| | | | |
|---|---|---|---|
| 5,043,268 | 8/1991 | Stock | 435/15 |
| 5,141,851 | 8/1992 | Brown et al. | 435/15 |
| 5,238,922 | 8/1993 | Graham et al. | 514/18 |
| 5,326,773 | 7/1994 | de Solms et al. | 514/336 |
| 5,340,828 | 8/1994 | Graham et al. | 514/357 |
| 5,352,705 | 10/1994 | Deana et al. | 514/630 |
| 5,439,918 | 8/1995 | de Solms et al. | 514/307 |
| 5,504,212 | 4/1996 | de Solms et al. | 546/336 |

FOREIGN PATENT DOCUMENTS

| | | |
|---|---|---|
| 0 456 180 A1 | 11/1991 | European Pat. Off. |
| 0 670 314 A1 | 3/1995 | European Pat. Off. |
| WO 91/16340 | 10/1991 | WIPO |
| WO 92/20661 | 11/1992 | WIPO |
| WO 95/10514 | 4/1995 | WIPO |
| WO 95/10515 | 4/1995 | WIPO |
| WO 95/10516 | 4/1995 | WIPO |

OTHER PUBLICATIONS

Kohl, N.E., et al., "Inhibition of farnesyltransferase induces regression of mammary and salivary carcinomas in ras transgenic mice," Nature Medicine, vol. 1, No. 8, pp. 792–797 (1995).

James, G.L., et al., "Benzodiazepine Peptidomimetic BZA–5B Interrupts the MAP Kinase Activation Pathway in H-Ras-transformed Rat-1 Cells, but Not in Untransformed Cells," Jour. of Biol. Chem., vol. 269, No. 44, pp. 27705–27714 (1994).

Sepp-Lorenzino, L., et al., "A Peptidomimetic Inhibitor of Farnesyl:Protein Transferase Blocks the Anchorage-dependent and -independent Growth of Human Tumor Cell Lines," Cancer Research, vol. 55, pp. 5302–5309 (1995).

Goldstein, J.L. et al., "Nonfarnesylated Tetrapeptide Inhibitors of Protein Farnesyltransferase," The Jour. of Biol. Chem., vol. 266, No. 24, pp. 15575–15578 (1991).

Kohl, N.E. et al., "Selective Inhibition of ras-Dependent Transformation by a Farnesyltransferase Inhibitor", Science, vol. 260, pp. 1934–1937 (1993).

James, G.L. et al., "Benzodiazepine Peptidomimetics: Potent Inhibitors of Ras Farnesylation in Animal Cells," Science, vol. 260, pp. 1937–1942 (1993).

Gibbs, J.B. et al., "Selective Inhibition of Farnesyl-Protein Transferase Blocks Ras Processing in Vivo," The Jour. of Biol. Chem., vol. 268, No. 11, pp. 7617–7620 (1993).

Pompliano, D.L., "Steady-State Kinetic Mechanism of Ras Farnesyl:Protein Transferase," Biochemistry, vol. 31, pp. 3800–3807 (1992).

Kohl, N.E. et al., "Protein farnesyltransferase inhibitors block the growth of ras-dependent tumors in nude mice", Proc. Nat'l. Acad. Sci., USA, vol. 91, pp. 9141–9145 (1994).

*Primary Examiner*—Mukund J. Shah
*Assistant Examiner*—Bruck Kifle
*Attorney, Agent, or Firm*—David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras. The compounds of formula A are representative of the compounds of the present invention:

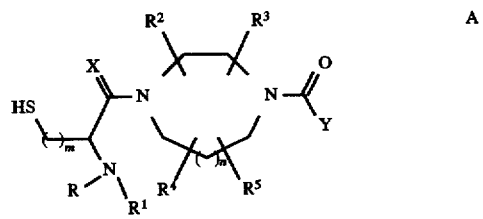

19 Claims, No Drawings

INHIBITORS OF FARNESYL-PROTEIN TRANSFERASE

RELATED APPLICATION

The present patent application is a continuation application of copending application PCT International Ser. No. US 94/05634, filed May 19, 1994, which is a continuation-in-part application of application Ser. No. 08/237,586, filed May 11, 1994, now abandoned, which is a continuation-in-part application of application Ser. No. 08/80,028, filed Jun. 18, 1993, now abandoned.

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171-286 (1989). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583-586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., Cell 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093-1098 (1989); Hancock et al., *Cell* 57:1167-1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., Cell, 62:81-88 (1990); Schaber et al., *J. Biol. Chem.*, 265:14701-14704 (1990); Schafer et al., Science, 249:1133-1139 (1990); Manne et al., *Proc. Natl. Acad. Sci USA*, 87:7541-7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630-6634(1989)). Cytosollocalized forms of Ras with normal GTPase activity do not act as inhibitors. Gibbs et al., ibid, showed this effect in *Xenopus oocytes* and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides containing cysteine as an amino terminal residue with the CAAX sequence inhibit Ras farnesylation (Schaber et al., ibid; Reiss et. al., ibid; Reiss et al., *PNAS*, 88:732-736 (1991)). Such inhibitors may inhibit while serving as alternate substrates for the Ras farnesyl-transferase enzyme, or may be purely competitive inhibitors (U.S. Pat. No. 5,141, 851, University of Texas).

Recently, it has been demonstrated that certain inhibitors of farnesyl-protein transferase selectively block the processing of Ras oncoprotein intracellularly (N. E. Kohl et al. *Science*, 260:1934-1937 (1993) and G. L. James et al. *Science*, 260:1937-1942 (1993).

It is, therefore, an object of this invention to develop non-peptide compounds which will inhibit farnesyl-protein transferase and the growth of cancer cells. It is a further object of this invention to develop chemotherapeutic compositions containing the compounds of this invention, and methods for producing the compounds of this invention.

SUMMARY OF THE INVENTION

The present invention includes substituted piperazine analogs which inhibit farnesyl-protein transferase and the farnesylation of the oncogene protein Ras, chemotherapeutic compositions containing the compounds of this invention, and methods for producing the compounds of this invention.

The compounds of this invention are illustrated by the formulae A, B and C:

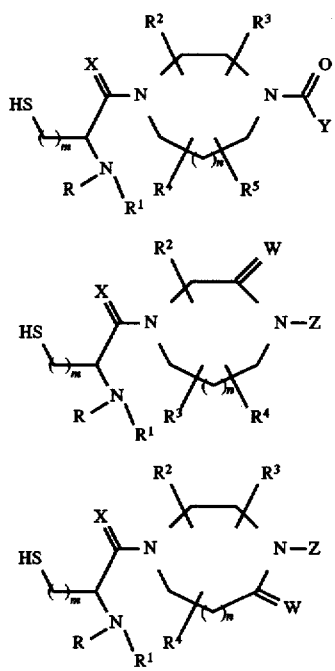

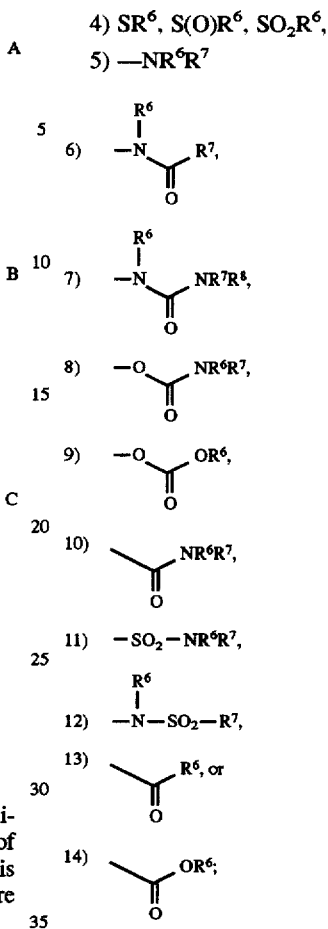

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula A:

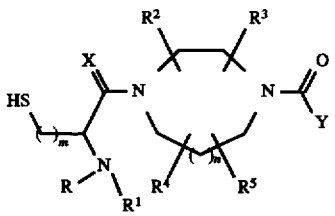

wherein
X is O or $H_2$;
m is 1 or 2
n is 0 or 1;
t is 1 to 4;
R and $R^1$ are independently selected from H, $C_{1-4}$ alkyl, or aralkyl;
$R^2$, $R^3$, $R^4$, and $R^5$ are independently selected from: H; $C_{1-8}$ alkyl, alkenyl, alkynyl, aryl, heterocycle,

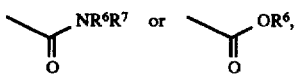

unsubstituted or substituted with one or more of
1) aryl or heterocycle, unsubstituted or substituted with:
   a) $C_{1-4}$ alkyl,
   b) $(CH_2)_tOR^6$,
   c) $(CH_2)_tNR^6R^7$,
   d) halogen,
2) $C_{3-6}$ cycloalkyl,
3) $OR^6$,
4) $SR^6$, $S(O)R^6$, $SO_2R^6$,
5) $-NR^6R^7$ 6) $-\underset{\underset{R^6}{|}}{N}\underset{O}{\overset{\|}{C}}R^7$, 7) $-\underset{\underset{R^6}{|}}{N}\underset{O}{\overset{\|}{C}}NR^7R^8$, 8) $-O\underset{O}{\overset{\|}{C}}NR^6R^7$, 9) $-O\underset{O}{\overset{\|}{C}}OR^6$, 10) $\underset{O}{\overset{\|}{C}}NR^6R^7$,

11) $-SO_2-NR^6R^7$,

12) $-\underset{\underset{R^6}{|}}{N}-SO_2-R^7$,

13) $\underset{O}{\overset{\|}{C}}R^6$, or

14) $\underset{O}{\overset{\|}{C}}OR^6$;

and any two of $R^2$, $R^3$, $R^4$, and $R^5$ are optionally attached to the same carbon atom;

Y is aryl, heterocycle, unsubstituted or substituted with one or more of:
1) $C_{1-4}$ alkyl, unsubstituted or substituted with:
   a) $C_{1-4}$ alkoxy,
   b) $NR^6R^7$,
   c) $C_{3-6}$ cycloalkyl,
   d) aryl or heterocycle,
   e) HO,
2) aryl or heterocycle,
3) halogen,
4) $OR^6$,
5) $NR^6R^7$,
6) CN,
7) $NO_2$, or
8) $CF_3$;

$R^6$, $R^7$ and $R^8$ are independently selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
   a) $C_{1-4}$ alkoxy,
   b) aryl or heterocycle,
   c) halogen, d) HO, e) 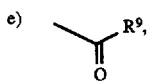

f) —SO$_2$R$^9$ g) NRR$^1$, wherein

R$^6$ and R$^7$ may be joined in a ring, and

R$^7$ and R$^8$ may be joined in a ring;

R$^9$ is C$_{1-4}$ alkyl or aralkyl;

or the pharmaceutically acceptable salts thereof.

In a second embodiment of this invention, the inhibitors of farnesyl-protein transferase are illustrated by the formula B:

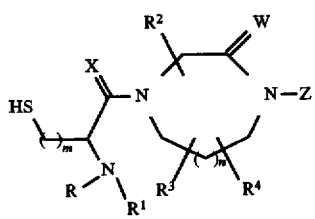

B wherein:

X is O or H$_2$;

m is 1 or 2;

n is 0 or 1;

t is 1 to 4;

R and R$^1$ are independently selected from H, C$_{1-4}$ alkyl, or aralkyl;

R$^2$, R$^3$ and R$^4$ are independently selected from: H; C$_{1-8}$ alkyl, alkenyl, alkynyl, aryl, heterocycle,

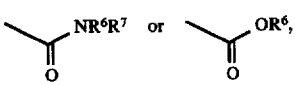

unsubstituted or substituted with one or more of 1) aryl or heterocycle, unsubstituted or substituted with:
 a) C$_{1-4}$ alkyl,
 b) (CH$_2$)$_r$OR$^6$,
 c) (CH$_2$)$_r$NR$^6$R$^7$,
 d) halogen, 2) C$_{3-6}$ cycloalkyl,

3) OR$^6$,

4) SR$^6$, S(O)R$^6$, SO$_2$R$^6$,

5) —NR$^6$R$^7$

6) 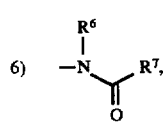

7) 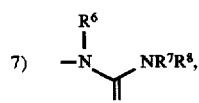

8) 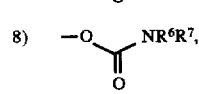

9) 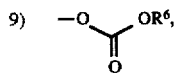

10) 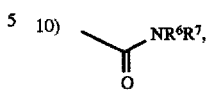

11) —SO$_2$—NR$^6$R$^7$,

12) 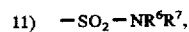

13) 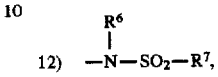, or

14) ;

and any two of R$^2$, R$^3$ and R$^4$ are optionally attached to the same carbon atom;

and wherein the carbon adjacent to the C=W moiety is substituted by at least one non-hydrogen group;

W is H$_2$ or O;

Z is aryl, heteroaryl, arylmethyl, heteroarylmethyl, arylsulfonyl, heteroarylsulfonyl, unsubstituted or substituted with one or more of the following:

1) C$_{1-4}$ alkyl, unsubstituted or substituted with:
 a) C$_{1-4}$ alkoxy,
 b) NR$^6$R$^7$,
 c) C$_{3-6}$ cycloalkyl,
 d) aryl or heterocycle, or
 e) HO, 2) aryl or heterocycle, 3) halogen,

4) OR$^6$,

5) NR$^6$R$^7$,

6) CN,

7) NO$_2$, or

8) CF$_3$,

R$^6$, R$^7$ and R$^8$ are independently selected from: H; C$_{1-4}$ alkyl, C$_{3-6}$ cycloalkyl, heterocycle, aryl, aroyl, heteroaroyl, arylsulfonyl, heteroarylsulfonyl, unsubstituted or substituted with:

a) C$_{1-4}$ alkoxy, b) aryl or heterocycle, c) halogen, d) HO, e) 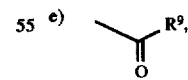

f) —SO$_2$R$^9$ g) NRR$^1$, wherein

R$^6$ and R$^7$ may be joined in a ring, and

R$^7$ and R$^8$ may be joined in a ring;

R$^9$ is C$_{1-4}$ alkyl or aralkyl;

or the pharmaceutically acceptable salts thereof.

In a third embodiment of this invention, the inhibitors of farnesyl-protein transferase are illustrated by the formula C:

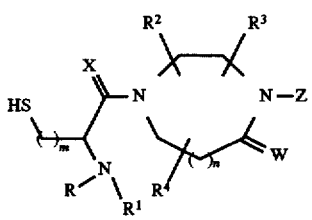

wherein:

X is O or $H_2$;
m is 1 or 2;
n is 1;
t is 1 to 4;
R and $R^1$ are independently selected from H, $C_{1-4}$ alkyl, or aralkyl;
$R^2$, $R^3$ and $R^4$ are independently selected from: H; $C_{1-8}$ alkyl, alkenyl, alkynyl, aryl, heterocycle,

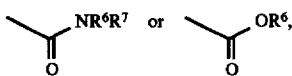

unsubstituted or substituted with one or more of 1) aryl or heterocycle, unsubstituted or substituted with:
   a) $C_{1-4}$ alkyl,
   b) $(CH_2)_tOR^6$,
   c) $(CH_2)_tNR^6R^7$,
   d) halogen,
2) $C_{3-6}$ cycloalkyl,
3) $OR^6$,
4) $SR^6$, $S(O)R^6$, $SO_2R^6$,
5) —$NR^6R^7$ 6) 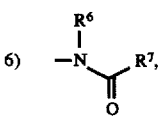

7) 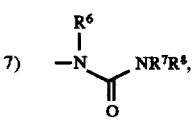

8) 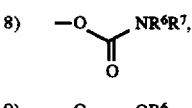

9) 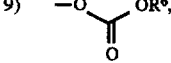

10) 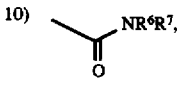

11) —$SO_2$—$NR^6R^7$,

12) 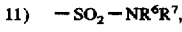

13) 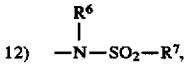

14) 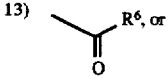

and any two of $R^2$, $R^3$ and $R^4$ are optionally attached to the same carbon atom;

and wherein the carbon adjacent to the C=W moiety is substituted by two hydrogens;

W is O;

Z is aryl, heteroaryl, arylmethyl, heteroarylmethyl, arylsulfonyl, heteroarylsulfonyl, unsubstituted or substituted with one or more of the following:

1) $C_{1-4}$ alkyl, unsubstituted or substituted with:
   a. $C_{1-4}$ alkoxy,
   b. $NR^6R^7$,
   c. $C_{3-6}$ cycloalkyl,
   d. aryl or heterocycle, or
   e. HO,
2) aryl or heterocycle,
3) halogen,
4) $OR^6$,
5) $NR^6R^7$,
6) CN,
7) $NO_2$, or
8) $CF_3$;

$R^6$, $R^7$ and $R^8$ are independently selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
   a) $C_{1-4}$ alkoxy,
   b) aryl or heterocycle,
   c) halogen,
   d) HO, e) 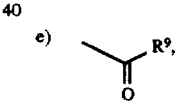

f) —$SO_2R^9$
g) $NRR^1$, wherein
$R^6$ and $R^7$ may be joined in a ring, and
$R^7$ and $R^8$ may be joined in a ring;
$R^9$ is $C_{1-4}$ alkyl or aralkyl;
or the pharmaceutically acceptable salts thereof.

The preferred compounds of this invention are illustrated by the following formula:

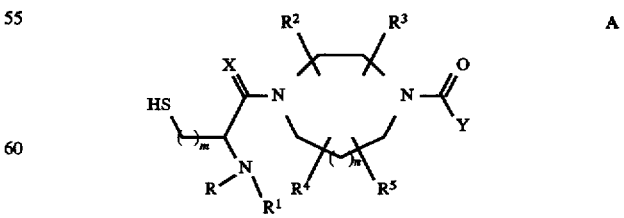

X is $H_2$;
n is 0;
m is 1;
R, $R_1$, $R^3$, $R^4$, $R^5$ is H or $CH_3$;

9

R² is H; C₁₋₅ alkyl, or

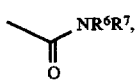

unbranched or branched, unsubstituted or substituted with one or more of:
1) aryl,
2) heterocycle,
3) OR⁶,
4) SR⁶, SO₂R⁶, or 5) 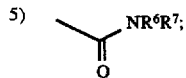

and any two of R², R³, R⁴, and R⁵ are optionally attached to the same carbon atom;

Y is aryl, heterocycle, unsubstituted or substituted with one or more of:
a) C₁₋₄ alkyl,
b) C₁₋₄ alkoxy,
c) halogen, or
d) NR⁶R⁷;

R⁶, R⁷ is independently selected from:
H; C₁₋₄ alkyl, C₃₋₆ cycloalkyl, aryl, heterocycle, unsubstituted or substituted with:
a) C₁₋₄ alkoxy,
b) halogen, or
c) aryl or heterocycle;
or the pharmaceutically acceptable salts thereof.

The most preferred compounds of this invention are illustrated by the following formula:

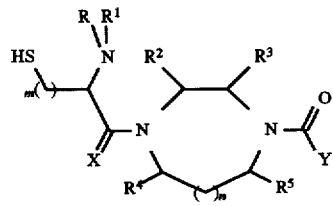

X is H₂;
m is 1;
n is 0;
R, R¹, R³, R⁴, R⁵ is H;
R² is C₁₋₄ alkyl, unsubstituted or substituted with one or more of:
1) phenyl,
2) pyridyl,
3) OR⁶, or
4) SR⁶, SO₂R⁶;

Y is Dihydrobenzofuryl, isoquinolinyl, naphthyl, quinolinyl, phenyl, unsubstituted or substituted with one or more of:
a) C₁₋₃ alkyl,
b) C₁₋₃ alkoxy, or
c) F, Cl;

R⁶ is
1) C₁₋₄ alkyl unsubstituted or substituted with:
a) phenyl,
b) pyridyl,
c) C₃₋₆ cycloalkyl,

10

2) phenyl,
3) pyridyl, or
4) C₃₋₆ cycloalkyl;

or the pharmaceutically acceptable salts thereof.

The preferred compounds of this invention are as follows:

1-[2-(R)-Amino-3-mercaptopropyl]-2(S)-(1-butyl)-4-(2,3-dimethyl-benzoyl)piperazine dihydrochloride

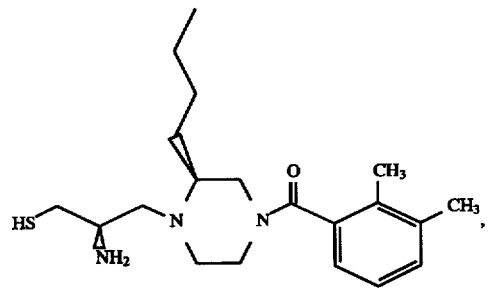

1-[2(R)-Amino-3-mercaptopropyl]-2(S)-(n-butyl)-4-(1-naphthoyl)piperazine

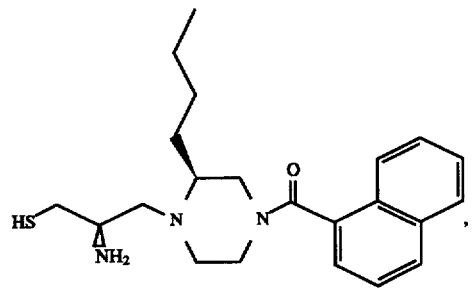

1-[2-(R)-Amino-3-mercaptopropyl]-2(S)-benzyl-4-[1-(2,3-dimethyl)benzoyl] piperazine

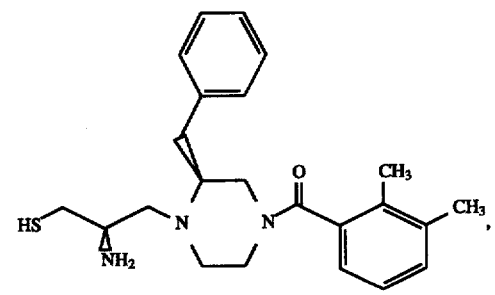

1-[2(R)-Amino-3-mercaptopropyl]-2(S)-(2-methoxy)ethyl-4-[1-(2,3-dimethyl)benzoyl] piperazine

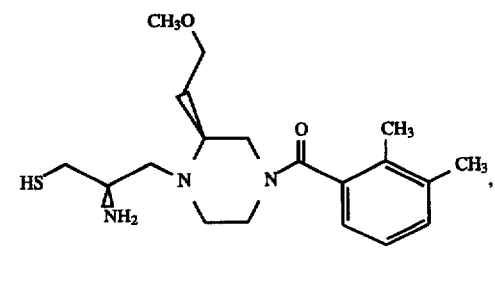

-continued

1-[2(R)-Amino-3-mercaptopropyl]-2(S)-(2-methylthio)ethyl-4-[1-(2,3-dimethyl)benzoyl]piperazine

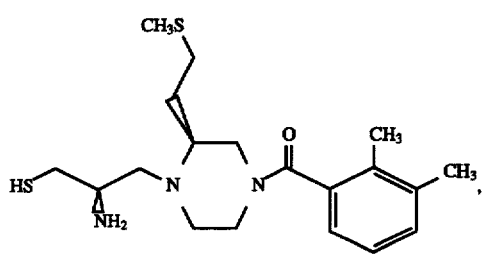

1-[2(R)-Amino-3-mercaptopropyl]-2(S)-(n-butyl)-4-[7-(2,3-dihydrobenzofuroyl)]piperazine

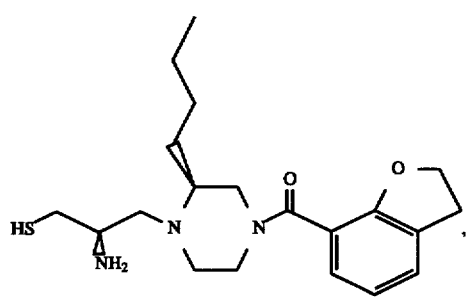

1-(2(R)-Amino-3-mercaptopropyl)-4-(1-naphthoyl)-2(S)-pyridinylcarboxyl-4-piperazine dihydrochloride

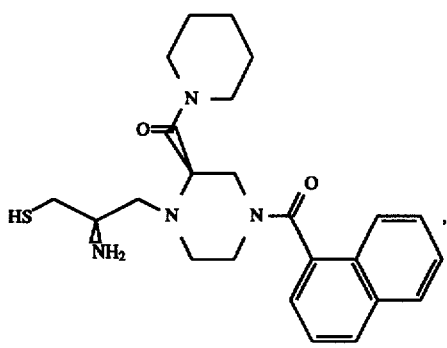

Methyl 4-(2(R)-amino-3-mercaptopropyl)-1-(1-naphthylmethyl)piperazine-2-carboxylate hydrochloride

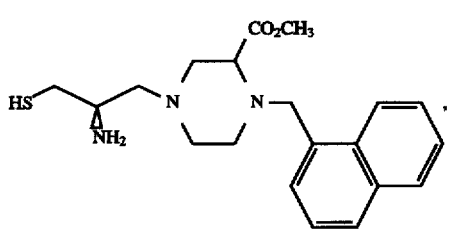

1-[2(R)-Amino-3-mercaptopropyl]-2(S)-(2-methoxyethyl)-4-(1-naphthoyl)piperazine

-continued

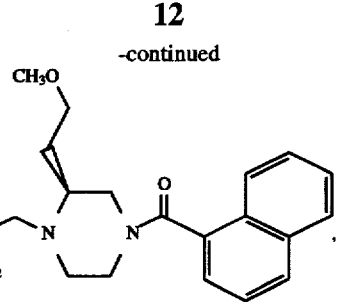

1-[2(R)-Amino-3-mercaptopropyl]-2(S)-n-butyl-4-(8-quinolinylcarbonyl)piperazine

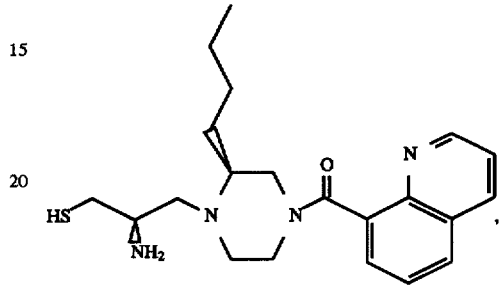

1-[2(R)-Amino-3-mercaptopropyl]-2-(S)-(2-(1-propoxy)ethyl)-4-(1-naphthoyl)piperazine

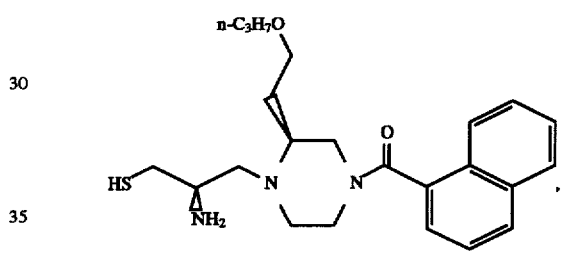

1-[2(R)-Amino-3-mercaptopropyl]-2(S)-(3-methoxy-1-propyl)-4-(1-naphthoyl)piperazine

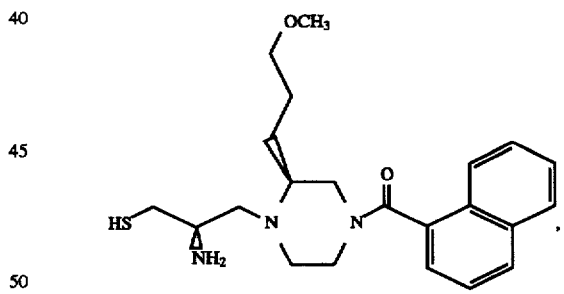

1-[2(R)-Amino-3-mercaptopropyl]-2(S)-(2-(1-propoxy)ethyl)-4-(8-quinolinoyl)piperazine

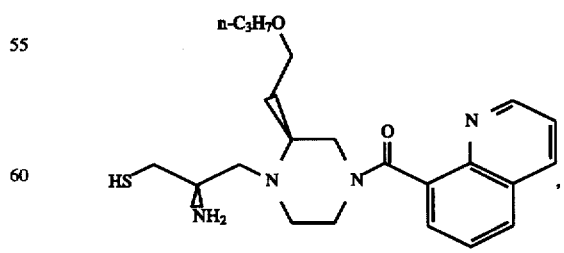

1-[2(R)-Amino-3-mercaptopropyl]-2(S)-[(3-pyridyl)methoxyethyl)]-4-(1-naphthoyl)piperazine -continued

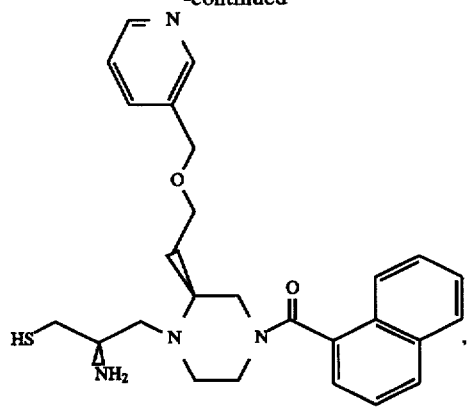

1-[2(R)-Amino-3-mercaptopropyl]-4-naphthoyl-2(S)-(2-phenylsulfonyl-ethyl)piperazine dihydrochloride

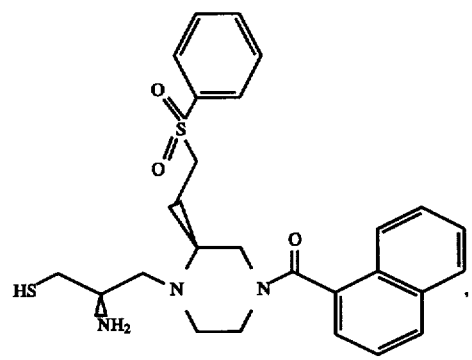

bis-1,1'-[2(R)-Amino-3-(2(S)-(2-methoxyethyl)-4-naphthoyl-1-piperazinyl)]propyl disulfide tetrahydrochloride

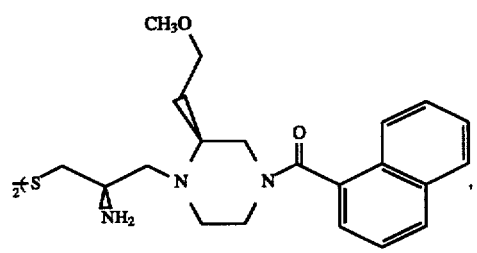

bis-1,1'-[2(R)-Amino-3-(-4naphthoyl-2(S)-(2-phenylsulfonylethyl)-1-piperazinyl)]propyl disulfide tetrahydrochloride

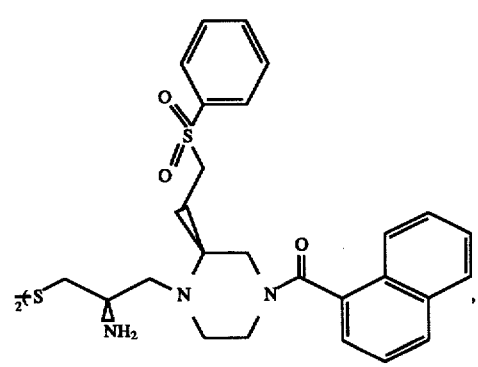

1-[2(R)-Amino-3-mercaptopropyl]-4-naphthoyl-2(S)-(2-cyclopropyloxyethyl)piperazine dihydrochloride -continued

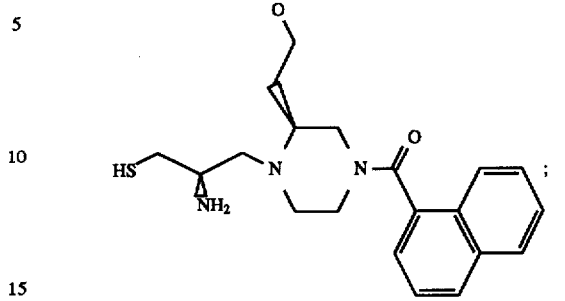

1-[2(R)-Amino-3-mercaptopropyl]-4-(1-naphthoyl)-2(S)-(4-acetamidobutyl)piperazine dihydrochloride

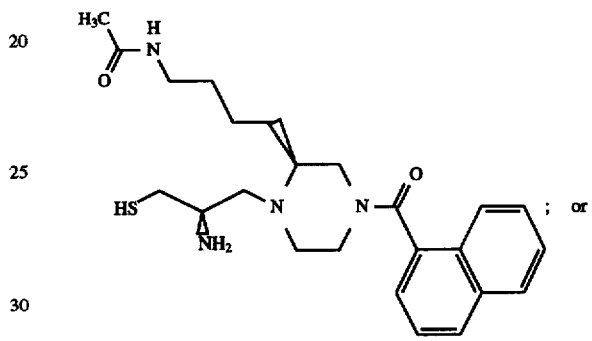; or

1-[2(R)-Amino-3-mercaptopropyl]-4-naphthoyl-2(S)-(2-cyclopropylmethylsulfonylethyl)piperazine dihydrochloride

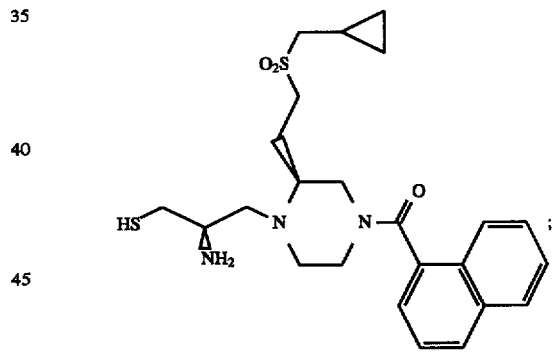;

or the pharmaceutically acceptable salts thereof.

The most preferred compounds of this invention are as follows:

1-[2(R)-Amino-3-mercaptopropyl]-2(S)-(2-methoxyethyl)-4-(1-naphthoyl)piperazine

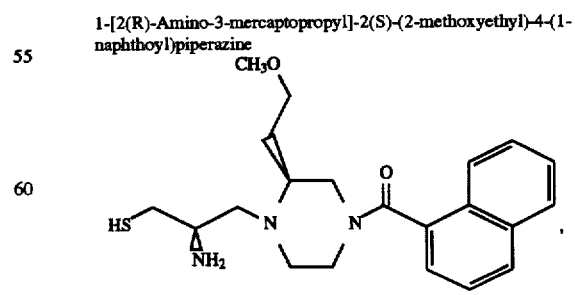

1-[2(R)-Amino-3-mercaptopropyl]-2(S)-n-butyl-4-(8-quinolinyl-carbonyl)piperazine 1-[2(R)-Amino-3-mercaptopropyl]-2(S)-(2-(1-propoxy)ethyl)-4-(1-naphthoyl)piperazine

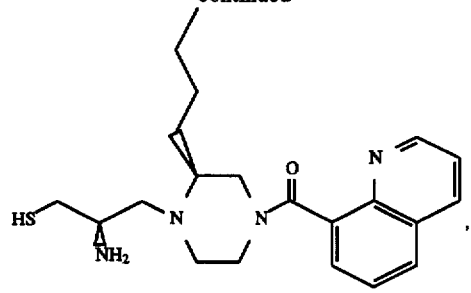

1-[2(R)-Amino-3-mercaptopropyl]-2(S)-(3-methoxy-1-propyl)-4-(1-naphthoyl)piperazine

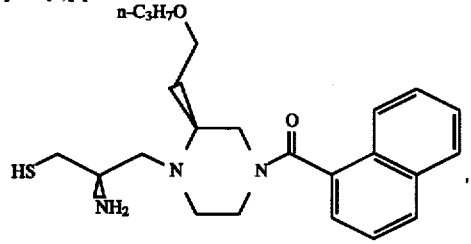

1-[2(R)-Amino-3-mercaptopropyl]-2(S)-(2-(1-propoxy)ethyl)-4-(8-quinolinoyl)piperazine

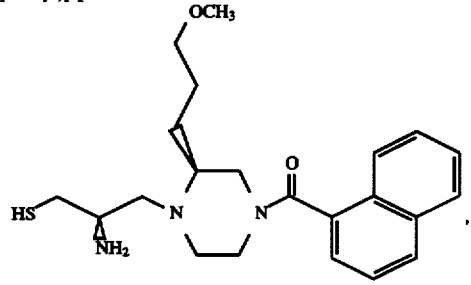

1-[2(R)-Amino-3-mercaptopropyl]-2(S)-[(3-pyridyl)methoxyethyl)]-4-(1-naphthoyl)piperazine

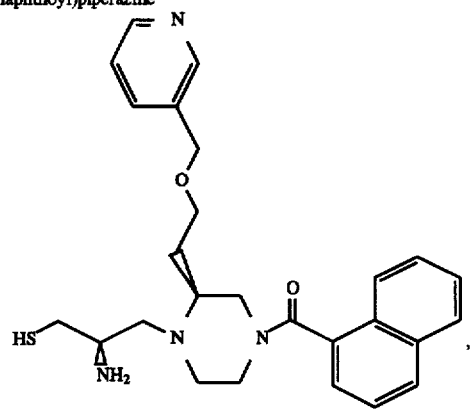

1-[2(R)-Amino-3-mercaptopropyl]-4-naphthoyl-2(S)-(2-phenylsulfonylethyl)piperazine dihydrochloride

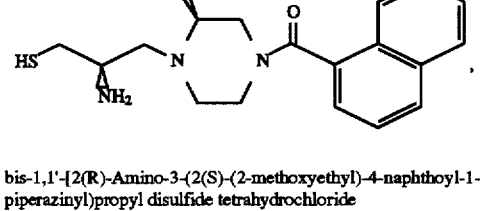

bis-1,1'-[2(R)-Amino-3-(2(S)-(2-methoxyethyl)-4-naphthoyl-1-piperazinyl)propyl disulfide tetrahydrochloride

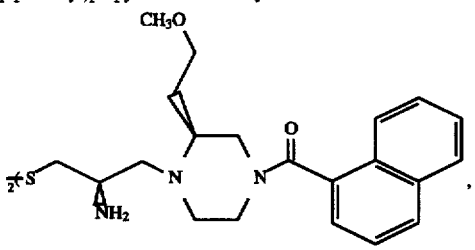

bis-1,1'-[2(R)-Amino-3-(4-naphthoyl-2(S)-(2-phenylsulfonylethyl)-1-piperazinyl)propyl disulfide tetrahydrochloride

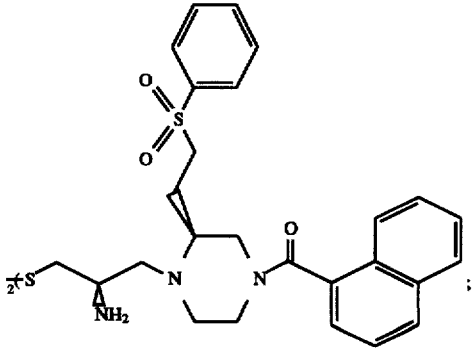

1-[2(R)-Amino-3-mercaptopropyl]-4-naphthoyl-2(S)-(2-cyclopropyloxyethyl)piperazine dihydrochloride

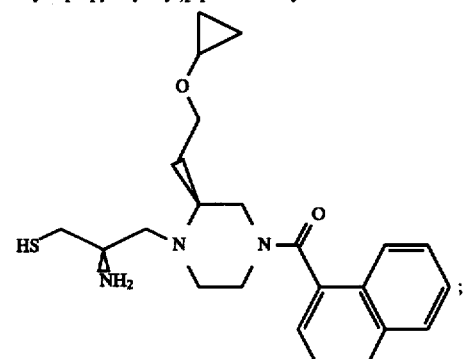

1-[2(R)-Amino-3-mercaptopropyl]-4-(1-naphthoyl)-2(S)-(4-acetamidobutyl)piperazine dihydrochloride -continued

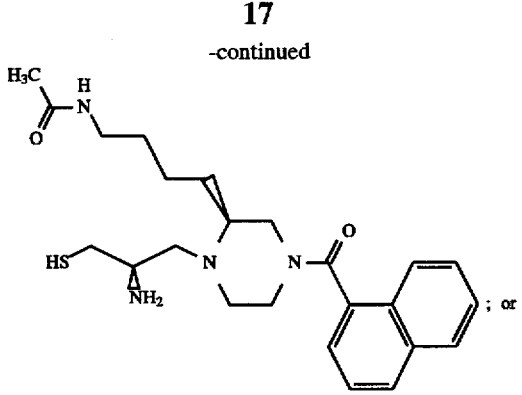

1-[2(R)-Amino-3-mercaptopropyl]-4-naphthoyl-2(S)-(2-cyclopropylmethylsulfonylethyl)piperazine dihydrochloride

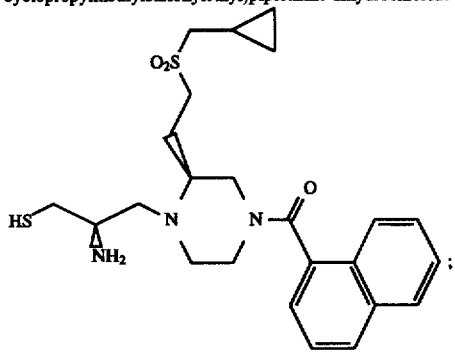

or the pharmaceutically acceptable salts thereof.

The compounds of the present invention may have asymmetric centers and occur as racemates, racemic mixtures, and as individual diastereomers, with all possible isomers, including optical isomers, being included in the present invention. The present invention further includes all disulfides of the claimed compounds, derived from two of the same compounds. When any variable (e.g. aryl, heterocycle, R¹, R² etc.) occurs more than one time in any constituent, its definition on each occurence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic, bicyclic or tricyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic or stable 11–15 membered tricyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Reaction Schemes 1–9, in addition to other standard manipulations such as ester hydrolysis, cleavage of protecting groups, etc., as may be known in the literature or exemplified in the experimental procedures. Substituents $R^a$ and $R^b$, as shown in the Schemes, represent the substituents $R^2$, $R^3$, $R^4$, and $R^5$; however their point of attachment to the ring is illustrative only and is not meant to be limiting.

These reactions may be employed in a linear sequence to provide the compounds of the invention or they may be used to synthesize fragments which are subsequently joined by the alkylation reactions described in the Reaction Schemes.

Synopsis of reaction Schemes 1–9

The requisite intermediates are in some cases commercially available, or can be prepared according to literature procedures, for the most part. In Scheme 1, for example, the synthesis of 2-alkyl substituted piperazines is outlined, and is essentially that described by J. S. Kiely and S. R. Priebe in Organic Preparations and Procedings Int., 1990, 22, 761–768. Boc-protected amino acids I, available commercially or by procedures known to those skilled in the art, can be coupled to N-benzyl amino acid esters using a variety of dehydrating agents such as DCC (dicyclohexycarbodiimide) or EDC.HCl (1-ethyl-3-(3-dimethylaminopropyl) carbodiimide hydrochloride) in a solvent such as methylene chloride, chloroform, dichloroethane, or in dimethylformamide. The product II is then deprotected with acid, for example hydrogen chloride in chloroform or ethyl acetate, or trifluoroacetic acid in methylene chloride, and cyclized under weakly basic conditions to give the diketopiperazine III. Reduction of III with lithium aluminum hydride in refluxing ether gives the piperazine IV, which is protected as the Boc derivative V. The N-benzyl group can be cleaved under standard conditions of hydrogenation, e.g., 10% palladium on carbon at 60 psi hydrogen on a Parr apparatus for 24–48 h. The product VI can be be treated with an acid chloride, or a carboxylic acid under standard dehydrating conditions to furnish the carboxamides VII; a final acid deprotection as previously described gives the intermediate VIII. This is reductively alkylated with the protected cysteinal XI, which is prepared from the appropriately protected cysteine derivative IX according to the procedure described by O. P. Goel, U. Krolls, M. Stier and S. Kesten in *Organic Syntheses*, 1988, 67, 69–75. The reductive alkylation can be accomplished at pH 5–7 with a variety of reducing agents, such as sodium triacetoxyborohydride or sodium cyanoborohydride in a solvent such as dichloroethane, methanol or dimethylformamide. The product XII can be deprotected to give the final compounds XIII with trifluoroacetic acid in methylene chloride in the presence of triethylsilane. The final product XIII is isolated in the salt form, for example, as a trifluoroacetate, hydrochloride or acetate salt, among others.

Alternatively, the protected piperazine intermediate V can be deprotected under acidic conditions as previously described to give IV; or IV can be used directly from Scheme 1 and reductively alkylated with the aldehyde XI as previously described to give compound XIV. The benzyl group can be removed from XIV with chloroethyl chloroformate under buffered conditions, followed by methanol to give compound XV. Elaboration as previously described results in the desired compounds XIII.

The disulfide of XIII can be prepared according to Scheme 4, wherein an alcoholic solution of a salt of XIII is treated with iodine.

Depending on the identity of the amino acid I, various side chains can be incorporated. For example when I is the Boc-protected β-benzyl ester of aspartic acid, the intermediate diketopiperazine XVII where n=1 and R=benzyl is obtained, as shown in Scheme 5. Subsequent lithium aluminum hydride reduction reduces the ester to the alcohol XVIII, which can then be reacted with a variety of alkylating agents such as an alkyl iodide, under basic conditions, for example, sodium hydride in dimethylformamide or tetrahydrofuran. The resulting ether XIX can then be carded on to final products as described in Scheme 2.

N-Aryl piperazines can be prepared as described in Scheme 6. An aryl amine XX is reacted with bis-chloroethyl amine hydrochloride in refluxing n-butanol to furnish compounds XXI. This is reductively alkylated with the aldehyde XI, and the product subjected to a final deprotection to give compounds XXIII.

Piperazin-5-ones can be prepared as shown in Scheme 7. Reductive amination of Boc-protected amino aldehydes XXV (prepared from I as descibed previously) gives rise to XXVI. This is then reacted with bromoacetyl bromide under Schotten-Baumann conditions; ring closure is effected with a base such as sodium hydride in a polar aprotic solvent such as dimethylformamide to give XXVII. The carbamate protecting group is removed under acidic conditions such as trifluoroacetic acid in methylene chloride, or hydrogen chloride gas in methanol or ethyl acetate, and the product reductively alkylated with the protected cysteinal XI as previously described to give, after final deprotection, the desired compounds.

The isomeric piperazin-3-ones can be prepared as described in Scheme 8. The imine formed from arylcarboxamides XXX and 2-aminoglycinal diethyl acetal can be reduced under a variety of conditions, including sodium triacetoxyborohydride in dichloroethane to give the amine XXXI. Amino acids I can be coupled to amines XXXI under standard conditions, and the resulting amide XXXII when treated with aqueous acid in tetrahydrofuran cyclized to the unsaturated XXXIII. Catalytic hydrogenation under standard conditions gives the requisite intermediate XXXIV, which is elaborted to final products as described in Scheme 7.

Access to alternatively substituted piperazines is described in Scheme 9. Following deprotection with trifluoroacetic acid, the N-benzyl piperazine V can be acylated with an aryl carboxylic acid. The resulting N-benzyl aryl carboxamide XXXVI can be hydrogenated in the presence of a catalyst to give the piperazine carboxamide XXXVII. Reductive alkylation of XXXVII with the protected cysteine aldehyde XI gives the fully elaborated XXXVIII, which can be deprotected to yield the desired isomer XXXIX.

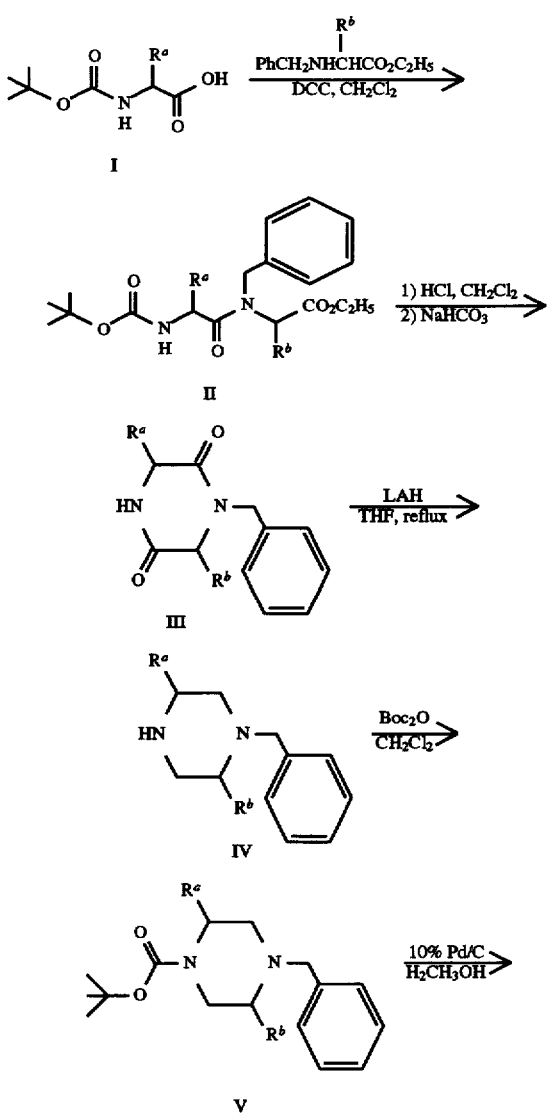

SCHEME 1

SCHEME 1
-continued
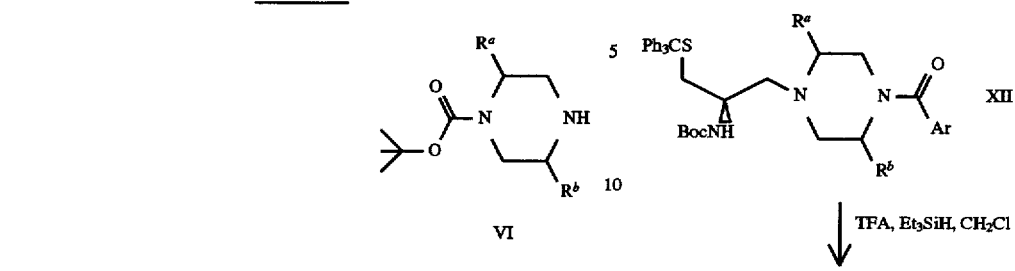
SCHEME 2
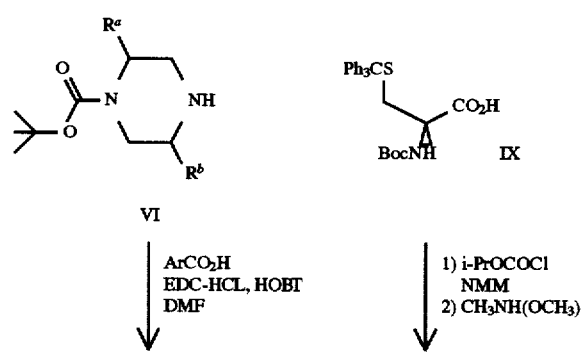
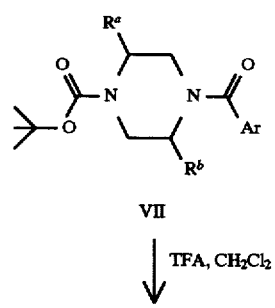
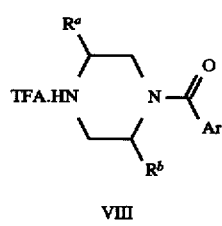
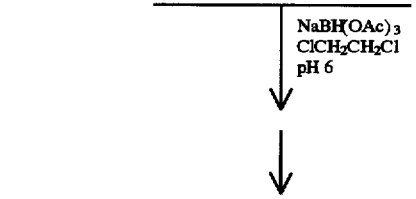
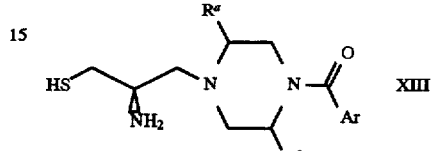
SCHEME 3
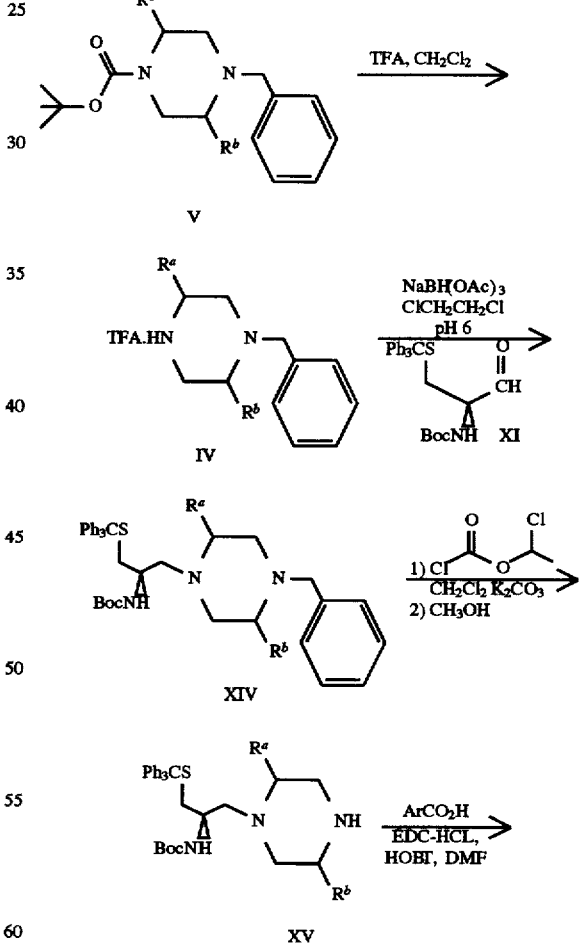

-continued
SCHEME 3
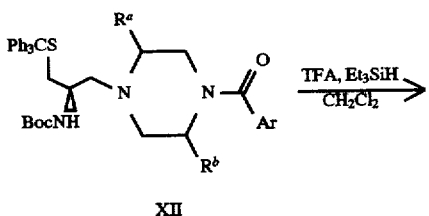
XII
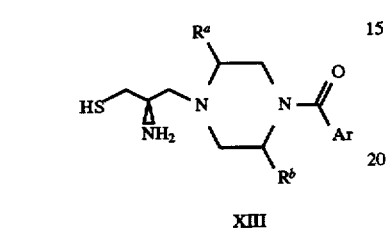
XIII
SCHEME 4
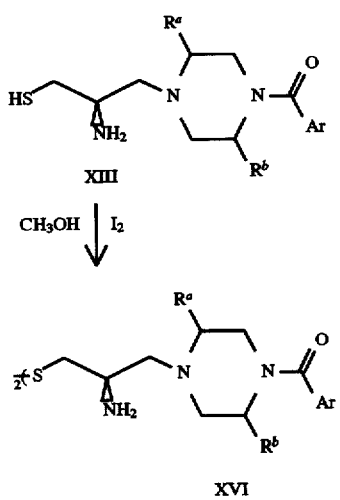
XVI
SCHEME 5
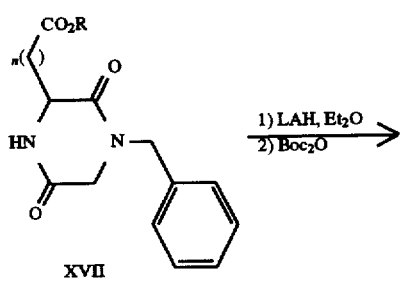
XVII
-continued
SCHEME 5
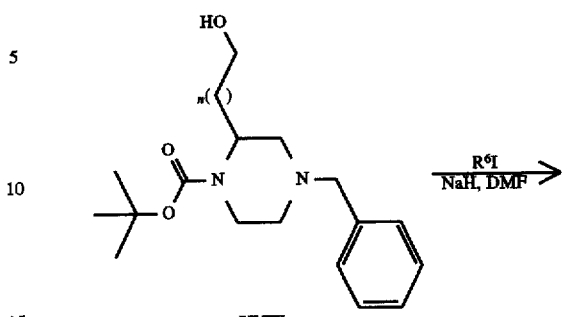
XVIII
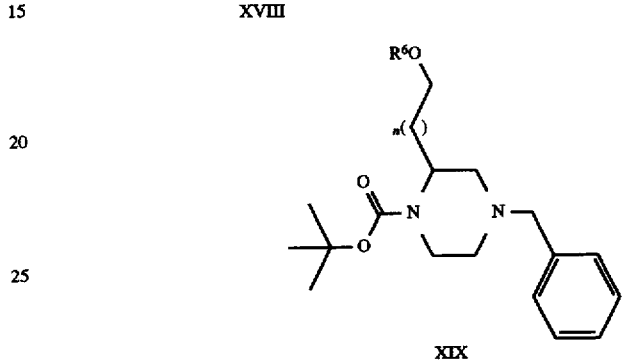
XIX
SCHEME 6
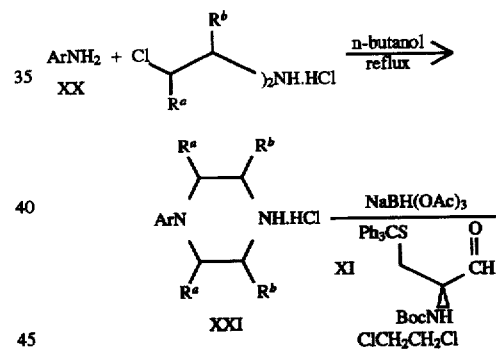
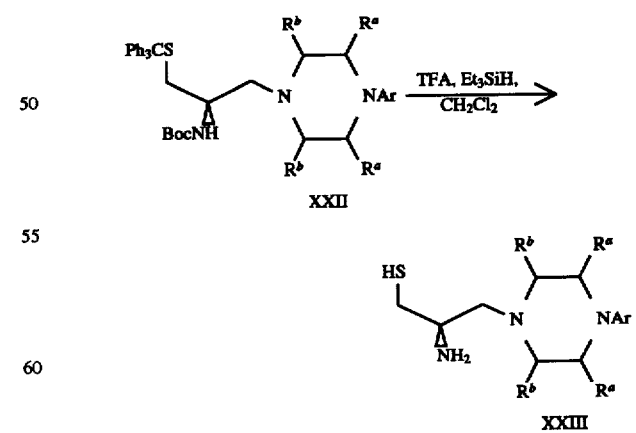
XXIII

SCHEME 7
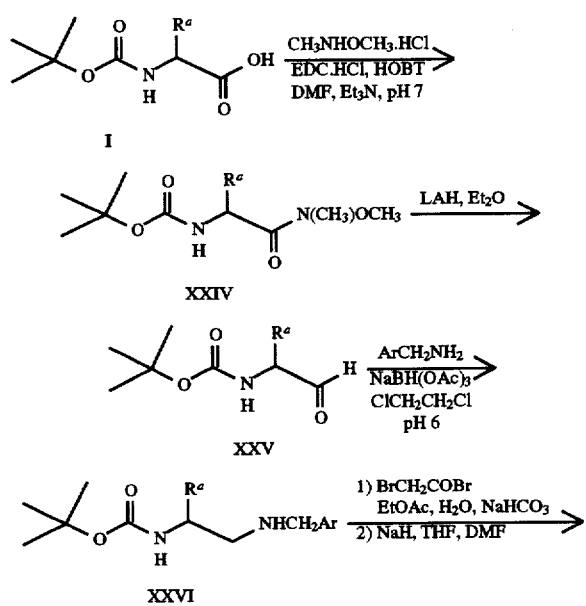
SCHEME 8
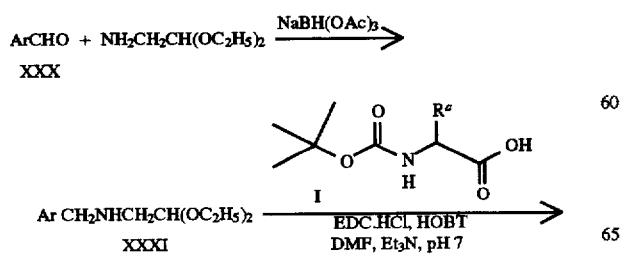
SCHEME 8 -continued
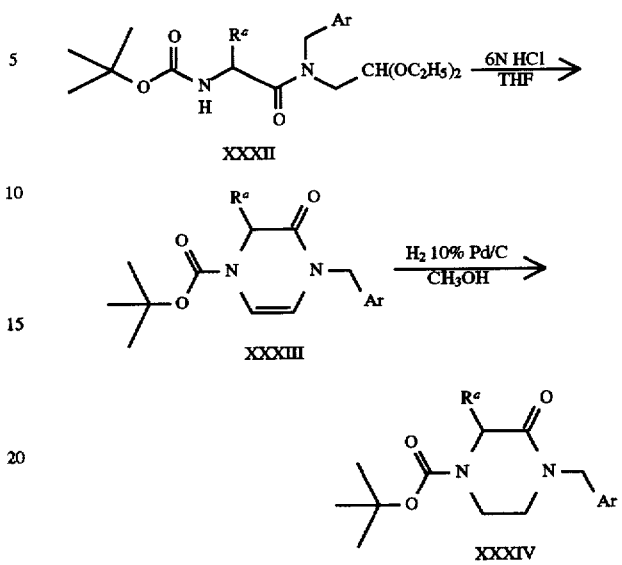
SCHEME 9
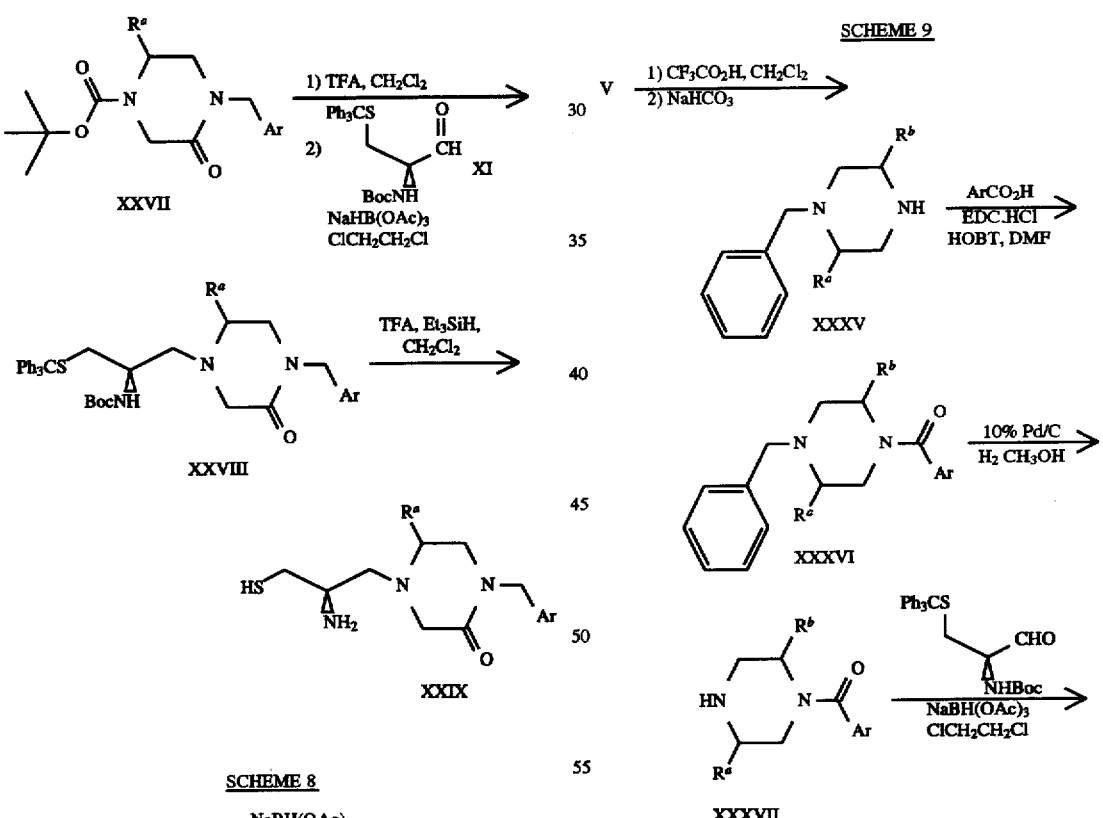

-continued
SCHEME 9

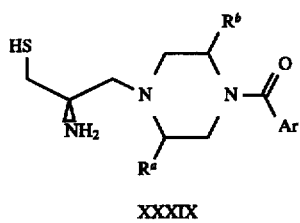

XXXIX

The compounds of this invention inhibit farnesyl-protein transferase and the farnesylation of the oncogene protein Ras. These compounds am useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

EXAMPLES

Examples provided are intended to assist in a further understanding of the invention. Particular materials employed, species and conditions are intended to be further illustrative of the invention and not limitative of the reasonable scope thereof. Purification by HPLC was accomplished with a 40×100 mm Waters PrepPak® reverse phase HPLC column (Delta-Pak™ $C_{18}$ 15 µm, 100 Å). Gradient elution employed 0.1% trifluoroacetic acid in water (Solvent A) and 0.1% trifluoroacetic acid in acetonitrile (Solvent B). Chloride salts were obtained by passing an aqueous solution of the trifluoroacetic acid salt through a Biorad AG® 3×4 ion exchange resin column (100–200 mesh, Cl-form). Purification by HPLC was utilized for each of the Examples 1–22 as set forth below.

Example 1

1-(2(R)-Amino-3-mercaptopropyl)-4-(2,3-dimethylbenzoyl)piperazine dihydrochloride Step A tert-Butyl 4-(2,3-dimethylbenzoyl)piperazine-1-carboxylate tert-Butyl piperazine-1-carboxylate(0.50 g, 2.6 mmol), 2,3-dimethylbenzoic acid (0.44 g, 2.9 mmol), 1-hydroxybenzotriazole (HOBT) (0.45 g, 2.9 mmol) and 1-ethyl-3-(3-dimethylamino- propyl)carbodiimide hydrochloride (EDC.HCl) (0.56 g, 2.9 mmol) were added to dry, degassed dimethylformamide (7 mL). The pH of the reaction was adjusted to 7 with triethylamine, and the reaction stirred for 2 h. The dimethylformamide (DMF) was distilled in vacuo, and the residue partitioned between ethyl acetate and water. The organic phase was washed with 2% aqueous potassium hydrogen sulfate, saturated sodium bicarbonate solution, saturated sodium chloride solution, and dried over magnesium sulfate. The crude product was chromatographed on silica gel using 30% ethyl acetate in hexane as eluant. The title compound was obtained as a white solid, NMR (CDCl$_3$, 300 MHz) δ 7.17 (1H, d, J=7 Hz), 7.13 (1H, t, J=7 Hz), 6.98 (1H, d, J=7 Hz), 3.77 (2H, m), 3.51 (2H, m), 3.32 (2H, t, J=5 Hz), 3.19 (2H, m), 2.28 (3H, s), 2.18 (3H, s), 1.45 (9H, s).

Step B

N-Methoxy-N-methyl 2(R)-tert-butoxycarbonylamino-3-triphenylmethylthiopropionamide The title compound was synthesized essentially according to the procedure described by O. P. Goel, U. Krolls, M. Stier, and S. Kesten in Organic Syntheses, 1988, 67, 69–75. Thus N,O-dimethyl-hydroxylamine hydrochloride (1.05 g, 10.82 mmol) and N-methyl-morpholine (1.22 mL, 11.14 mmol) were stirred in dichloromethane (6 mL) under nitrogen at 0° C. for 30 min. In a separate flask, 2(R)-tert-butoxycarbonylamino-3-triphenylmethyl-thiopropionic acid (5.02 g, 10.82 mmol) in tetrahydrofuran (11.5 mL, dry) and methylene chloride (45 mL) were cooled to −20° C., and N-methylmorpholine (1.22 mL, 11.14 mmol) and isopropylchloroformate (10.82 mL of 1M solution in toluene) were added via syringe, maintaining the temperature less than −15° C. The reaction was stirred at −30° C., and the suspension of N,O-dimethylhydroxylamine hydrochloride and N-methylmorpholine in methylene chloride added all at once. The cooling bath was removed and the reaction allowed to warm to room temperature over 4 h. The reaction was cooled to 0° C. and quickly washed with two portions of 0.2N hydrochloric acid, two portions of 0.5N sodium hydroxide, and saturated sodium chloride solution. The organic phase was dried over magnesium sulfate, filtered and reduced in vacuo to obtain the title compound as a clear gum, 5.50 g. NMR (300 MHz, DMSO-$d_6$) δ 7.30 (15H, m), 4.43 (1H, br s), 3.56 (3H, s), 2.99 (3H, s), 2.30 (2H, m), 1.36 (9H, s).

Step C

2(R)-tert-Butoxycarbonylamino-3-triphenylmethylthiopropanal

The title compound was synthesized essentially according to the procedure described by O. P. Goel, U. Krolls, M. Stier, and S. Kesten in Organic Syntheses, 1988, 67, 69–75. Thus lithium aluminum hydride (0.451 g, 11.90 mmol) and diethyl ether (40 mL) were stirred at 20° C. under nitrogen for 1 h, then cooled to −45° C. N-Methoxy-N-methyl 2(R)-tert-butoxycarbonylamino-3triphenylmethylthiopropionamide (5.50 g, 10.82 mmol) in diethyl ether (20 mL) was added in a steady stream, maintaining the temperature less than −35° C. The cooling bath was removed and the reaction warmed to 5° C., then cooled to −35° C. A solution of potassium hydrogen sulfate (2.94 g, 21.64 mmol) in water (50 mL) was added slowly, maintaining the temperature less than 0° C. The reaction was warmed to 20° C. over 1 h, and filtered through Celite. The filtrate was washed with 10% citric acid, saturated sodium chloride solution, and dried over magnesium sulfate. After filtration, the solvents were removed in vacuo and the title compound obtained as a foam (4.80 g).

Step D 1-(2(R)-tert-Butoxycarbonylamino-3-triphenylmethylthiopropyl)-4-(2,3-dimethylbenzoyl)piperazine The product from step A (0.480 g, 0.860 mmol) was dissolved in methylene chloride (4 mL) and trifluoroacetic acid was added (2 mL). The reaction was stirred for 30 min. at 20° C., then evaporated to dryness. The crude trifluoroacetate salt was taken up in dimethylformamide and the pH adjusted to 6 by the addition of triethylamine. To this solution was added sodium triacetoxyborohydride (0.331 g, 1.56 mmol), and crushed molecular sieves (0.5 g), and the reaction cooled to 0° C. under nitrogen. 2(R)-N-tert-butoxycarbonylamino-3-triphenylmethylthiopropanal (0.350 g, 0.782 mmol) in dimethylformamide was added slowly dropwise. The reaction was stirred at 20° C. under nitrogen for 2 h. The dimethylformamide was removed in vacuo and the residue partitioned between saturated sodium bicarbonate and ethyl acetate. The organic phase was washed with saturated sodium chloride and dried over magnesium sulfate. Filtration and evaporation gave the title compound as a white foam. NMR (CDCl$_3$, 300 MHz) δ 7.0–7.6 (18H, m), 5.60 (1H, br s), 4.4–4.9 (1H, m), 2.1–3.9 (12H, m), 2.25 (3H, s), 2.15 (3H, br s), 1.40 (9H, s).

Step E 1-(2(R)-Amino-3-mercaptopropyl)-4-(2,3-dimethylbenzoyl)piperazine dihydrochloride The product from step D and triethylsilane (0.54 mL, 3.4 mmol) were dissolved in methylene chloride (6 mL). To this solution was added trifluoroacetic acid (3 mL) and the reaction stirred at 20° C. for 30 min. The reaction was evaporated to dryness and partitioned between hexane and water. The aqueous phase was injected onto a 40×100 mm Waters PrepPak® reverse phase HPLC column (Delta-Pak™ C$_{18}$15 μm, 100 Å), and pure product isolated by gradient elution using 100% Solvent A (0.1% trifluoroacetic acid in water) to 50% Solvent A/50% Solvent B (0.1% trifluoroacetic acid in acetonitrile) over 50 min at a flow rate of 40 mL/min. Combined fractions were evaporated, dissolved in water and passed through a Biorad AG® 3×4 ion exchange resin column (100–200 mesh, Cl-form). The column eluant was lyophilized to give the title compound as a white powder.

Analysis calculated for C$_{16}$H$_{25}$N$_3$OS.2.4 HCl.1.4 H$_2$O: C, 45.76; H, 7.25; N; 10.01. Found: C, 45.73, H; 7.25; N, 10.01.

Example 2

1-[2(R)-Amino-3-mercaptopropyl]-4(S)-(2,3-dimethylbenzoyl)-2methylpiperazine dihydrochloride Step A 1-Benzyl-3(S)-methylpiperazine-2,5-dione The title compound was prepared according to the procedure described by John S. Kiely and Stephen R. Priebe in Organic Preparations and Procedures Int., 22 (6), 761–768 (1990). Thus 100 mL of a stock solution of dicyclohexylcarbodiimide in methylene chloride (0.5M) was added to methylene chloride (250 mL). This solution was cooled to 0° C. under nitrogen and Boc-L-alanine (9.46 g, 50.00 mmol) was added. The resulting slurry was stirred for 5 min, and then ethyl N-benzylglycinate (9.37 mL, 50.00 mmol) was added. The reaction was stirred for 2 h at 0° C., then at 20° C. overnight. The precipitate was removed by filtration, and hydrogen chloride gas bubbled through the methylene chloride solution for 2–4 h, until the reaction was shown to be complete by tlc. The solvent was removed in vacuo, and the residue partitioned between ethyl acetate (150 mL) and saturated sodium bicarbonate solution (42 mL). The organic phase was washed with saturated sodium chloride, dryed over magnesium sulfate, filtered and evaporated. The crude product was recrystallized from toluene to give the title compound as white crystals (5.88 g). NMR (300 MHz, CDCl$_3$) δ 7.30–7.38 (3H, m), 7.22–7.30 (2H, m), 6.94 (1H, br s), 4.59 (2H, s), 4.14 (1H, q, J=7 Hz), 3.84 (2H, s), 1.52 (3H, d, J=7 Hz).

Step B

4-Benzyl-1-tert-butoxycarbonyl-2(S)-methylpiperazine

The product from Step A (5.88 g, 27.00 mmol) was dissolved in THF (200 mL) and cooled under nitrogen to 0° C. with mechanical stirring. Lithium aluminum hydride (3.69 g, 0.097 mol) was added slowly. The reaction was refluxed for 18 h, cooled to 0° C., and quenched by the sequential slow addition of 5 mL H$_2$O, 5 mL 10% sodium hydroxide solution and 5 mL H$_2$O. The reaction was stirred for 30 min and filtered. The solvent was removed in vacuo, the crude product taken up in methylene chloride and dried over magnesium sulfate. The drying agent was removed by filtration, and the filtrate treated with di-tert-butyl dicarbonate (6.03 g, 27.6 mmol). After 2 h at 20° C., saturated sodium bicarbonate was added. The layers were separated, and the organic phase washed with saturated sodium chloride solution, then dried over magnesium sulfate. Filtration and evaporation gave the crude product which was purified by column chromatography on silica gel, eluting with 5% ethyl acetate in hexane. The title compound was obtained as a foam (5.28 g). NMR (300 MHz, CDCl$_3$) δ 7.25 (5H, m), 4.18 (1H, br s,), 3.80 (1H, d, J=12 Hz), 3.46 (2H, AB q, J=14 Hz), 3.11 (1H, dt, J=4, 12 Hz), 2.75 (1H, d, J=10 Hz), 2.58 (1H, d, J=10 Hz), 2.12 (1H, dd, J=4, 12 Hz), 2.00 (1H, dt, J=4, 12 Hz), 1.45 (9H, s), 1.23 (3H, d, J=7 Hz).

Step C 1-tert-Butoxycarbonyl-2(S)-methylpiperazine

The product from Step B (5.28 g, 18.2 mmol) was dissolved in methanol (75 mL) in a Parr bottle, and the vessel purged with argon. To this was added 10 % palladium on carbon (1.0 g) and the reaction hydrogenated under 60 psi hydrogen for 24 h. The catalyst was removed by filtration through Celite, and the filtrate evaporated in vacuo to give the title compound as an oil (3.33 g). NMR (300 MHz, CDCl$_3$) δ 4.15 (1H, m), 3.77 (1H, d, J=12 Hz), 2.85–3.06 (3H, m), 2.75 (1H, d, J=12 Hz), 2.64 (1H, dt, J=4, 12 Hz), 2.13 (1H, s), 1.45 (9H, s), 1.40 (3H, d, J=7 Hz).

Step D 1-tert-Butoxycarbonyl-4-(2,3-dimethylbenzoyl)-2(S)-methylpiperazine

The product from Step C (1.00 g, 5.00 mmol) was converted to the title compound according to the procedure described in Example 1, Step A using 2,3-dimethylbenzoic acid (0.750 g, 5.00 mmol), HOBT (0.765 g, 5.00 mmol), EDC.HCl (0.958 g, 5.00 mmol) and triethylamine to adjust the pH to 7. The title compound was obtained as a pale yellow solid (1.64 g).

Step E

1-[2(R)-N-tert-Butoxycarbonylamino-3-triphenylmethylthiopropyl]-4-(2,3-dimethylbenzoyl)-2(S)-methylpiperazine The title compound was obtained from the product of Step D (0.390 g, 1.17 mmol) according to the procedure described in Example 1, Step D. Thus, 1-tert-butoxycarbonyl-4-(2,3-dimethylbenzoyl)-2(S)-methylpiperazine (0.390 g, 1.17 mmol) was first treated with trifluoroacetic acid (3 mL) in methylene chloride (6 mL) for 30 min. The reaction was evaporated to dryness, and the crude product reacted with sodium triacetoxyborohydride (0.331 g, 1.56 mmol) and 2(R)-N-tert-butoxycarbonylamino-3-triphenylmethylthiopropanal (0.350 g, 0.782 mmol) in the presence of crushed molecular sieves (0.5 g) in DMF at pH 6 and 0°–20° C. overnight. The title compound was obtained as a foam (0.370 g).

Step F

1-[2(R)-Amino-3-mercaptopropyl]-4-(2,3-dimethylbenzoyl)-2(S)-methylpiperazine dihydrochloride The product from Step E (0.370 g, 0.55 mmol) was converted to the title compound according to the procedure described for Step E, Example 1 using triethylsilane (0.350 mL, 2.20 mmol) and trifluoroacetic acid (4.5 mL) in methylene chloride (9 mL). Purification by preparative HPLC (gradient elution: 100% Solvent A to 50% Solvent A/50% Solvent B, 50 min) and ion exchange provided the title compound as a white powder (0.140 g).

Analysis calculated for $C_{17}H_{27}N_3OS.2.7\ HCl.1.1\ H_2O$: C, 46.47; H, 7.32; N; 9.56. Found: C, 46.40, H, 7.31, N, 9.39.

Example 3

1-[2(R)-Amino-3-mercaptopropyl]-2(S)-n-butyl-4-(2,3-dimethylbenzoyl)piperazine dihydrochloride and 1-[2(S)-amino-3-mercaptopropyl]-2(S)-n-butyl-4-(2,3-dimethylbenzoyl)piperazine dihydrochloride Step A 1-Benzyl-3(S)-n-butylpiperazine-2,5-dione The title compound was prepared according to the procedure described in Example 2, Step A, except using Boc-L-norleucine (10.5 g, 45.2 mmol), ethyl N-benzylglycinate (8.72 g, 45.2 mmol) and dicyclohexylcarbodiimide (9.33 g, 45.2 mmol). The crude diketopiperazine was triturated with hexane to give the title compound as a white powder (12.0 g). NMR (300 MHz, CDCl$_3$) δ 7.24–7.40 (5H, m), 6.22 (1H, br s), 4.07 (1H, dt, J=3, 6 Hz), 3.87 (1H, d, J=17 Hz), 3.80 (1H, d, J=17 Hz), 1.88 (2H, m), 1.35 (4H, m), 0.91 (3H, t, J=7 Hz).

Step B

4-Benzyl-1-tert-butoxycarbonyl-2(S)-n-butylpiperazine

The title compound was prepared according to the procedure described in Example 2, Step B, except using 1-benzyl-3(S)-n-butylpiperazine-2,5-dione (4.95 g, 0.019 mol) and lithium aluminum hydride (2.60 g, 0.0685 mol), followed by di-tert-butyl dicarbonate (4.35 g, 0.020 mol). The crude product was purified by column chromatography on silica gel, eluting with 5% ethyl acetate in hexane. The title compound was obtained as a foam (5.63 g). NMR (300 MHz, DMSO-d$_6$) δ 7.25 (5H, m), 3.90 (1H, br s,), 3.73 (1H, d, J=13 Hz), 3.51 (1H, d, J=13 Hz), 3.34 (1H, d, J=13 Hz), 2.93 (1H, m), 2.75 (1H, d, J=11 Hz), 2.62 (1H, d, J=11 Hz), 1.90 (2H, m), 1.60 (2H, m), 1.38 (9H,s), 1.26 (2H, m), 1.04 (2H, m), 0.84 (3H, t, J=7 Hz).

Step C 1-tert-Butoxycarbonyl-2(S)-n-butylpiperazine

The title compound was prepared according to the procedure described in Example 2, Step C, except using 4-benzyl-1-tert-butoxycarbonyl-2(S)-n-butylpiperazine (3.75 g, 11.3 mmol) and 10% palladium on carbon (0.80 g). The title compound was obtained as an oil (2.68 g). NMR (300 MHz, CDCl$_3$) δ 4.08 (1H, br s), 3.90 (1H, d, J=12 Hz), 2.5–3.8 (6H, m), 1.80 (1H, m), 1.60 (1H, m), 1.46 (9H, s), 1.30 (4H, m),0.90 (3H, t, J=7 Hz).

Step D 1-tert-Butoxycarbonyl-2(S)-n-butyl-4-(2,3-dimethylbenzoyl)piperazine

The title compound was prepared according to the procedure described for Example 1, Step A except using 1-tert-butoxycarbonyl-2(S)-n-butylpiperazine (1.26 g, 5.20 mmol), 2,3-dimethylbenzoic acid (0.820 g, 5.46 mmol), HOBT (0.70 g, 5.20 mmol), EDC.HCl (1.09 g, 5.72 mmol) and triethylamine to adjust the pH to 7. The crude product was chromatographed on silica gel with 20% ethyl acetate in hexane. The title compound was obtained as a thick oil (1.76 g). NMR (300 MHz, DMSO-d$_6$) δ 7.15 (2H, m), 6.06 (1H,m), 4.42 (1H,m), 3.6–4.2 (2H, m), 2.7–3.24 (4H, m), 2.24 (3H, s), 2.03–2.20 (3H, 4s), 1.10–1.6 (15H, m), 0.72–1.00 (3H, m).

Step E

1-[2(R)-N-tert-Butoxycarbonylamino-3-triphenylmethylthiopropyl]-2(S)-n-butyl-4-(2,3dimethylbenzoyl)piperazine and 1-[(S)-2-N-tert-butoxycarbonylamino-3-triphenylmethylthiopropyl]-2(S)-n-butyl-4-(2,3-dimethylbenzoyl)piperazine The title compounds were prepared according to the procedure described in Example 1, Step D, except using 1-tert-butoxycarbonyl-2(S)-n-butyl-4-(2,3-dimethylbenzoyl)piperazine (1.76 g, 4.70 mmol) and trifluoroacetic acid (11 mL) in methylene chloride (25 mL). The crude deblocked product was converted to the free base. The free base (0.845 g, 3.08 mmol) was reacted with 2(R)-N-tert-butoxycarbonylamino-3-triphenylmethylthiopropanal (1.37 g, 3.08 mmol), sodium triacetoxyborohydride (2.95 g, 13.8 mmol) in the presence of crushed molecular sieves (0.5 g) in dichloroethane. Acetic acid was added to adjust the pH to 6. The crude product was chromatographed on silica gel with 30% ethyl acetate in hexane, and the title compounds isolated as a foam (1.47 g).

Step F

1-[(R)-2-Amino-3-mercaptopropyl]-2(S)-n-butyl-4-(2,3-dimethylbenzoyl)piperazine dihydrochloride and 1-[(S)-2-Amino-3-mercaptopropyl]-2(S)-n-butyl-4-(2,3-dimethylbenzoyl)piperazine dihydrochloride The title compound was obtained according to the procedure described for Step E, Example 1 except using approximately a 9:1 mixture of 1-[2(R)-N-tert-butoxycarbonylamino-3-triphenylmethylthiopropyl]-2(S)-n-butyl-4-(2,3-dimethylbenzoyl)piperazine and 1-[2(S)-N-tert-butoxycarbonylamino-3-triphenylmethylthiopropyl]-2(S)-n-butyl-4-(2,3-dimethylbenzoyl)piperazine (0.392, 0.55 mmol), triethylsilane (0.354 mL, 2.22 mmol) and trifluoroacetic acid (6 mL) in methylene chloride (12 mL). Purification by preparative HPLC (gradient elution: 85% Solvent A to 55% Solvent A/45% Solvent B, 70 min) and ion exchange provided the major product, 1-[2(R)-amino-3-mercaptopropyl]-2(S)-n-butyl-4-(2,3-dimethylbenzoyl) piperazine dihydrochloride as a white powder (133 mg) (HPLC retention time 8.90 min, 15 cm Vydac C18 column, 85% Solvent A to 55% Solvent A/45% Solvent B, 15 min, flow rate 1.5 mL/min).

Analysis calculated for $C_{20}H_{33}N_3OS \cdot 2$ HCl$\cdot 1.1$ H$_2$O: C, 52.65; H, 8.22; N; 9.21. Found: C, 53.42; H, 7.82; N, 9.06.

The minor product, 1-[2(S)-amino-3-mercaptopropyl]-2(S)-n-butyl-4-(2,3-dimethylbenzoyl)piperazine dihydrochloride was isolated from later HPLC fractions (HPLC retention time 9.42 min, 15 cm Vydac C18 column, 85% Solvent A to 55% Solvent A/45% Solvent B, 15 min, flow rate 1.5 mL/min).

Analysis calculated for $C_{20}H_{33}N_3OS \cdot 2.70$ HCl$\cdot 0.65$ H$_2$O: C, 50.71; H, 7.87; N, 8.87. Found: C, 50.73; H, 7.86; N, 8.83.

Example 4 bis-1,1'-[(R)-2-Amino-3-((S)-2-n-butyl-4-(2,3-dimethylbenzoyl)-1-piperazinyl)]propyl disulfide tetrahydrochloride A solution of iodine in methanol was added to a solution of 1[2(R)-amino-3-mercaptopropyl]-2(S)-n-butyl-4-(2,3-dimethylbenzoyl)piperazine dihydrochloride (40 mg, 0.091 mmol) in methanol (15 mL) until a slight yellow color persisted. The solvent was evaporated and the crude product dissolved in methanol-water and purified by preparative HPLC using a gradient elution of 85% Solvent A to 35% Solvent A/65% Solvent B over 60 min. After ion exchange with Biorad AG® 3×4 ion exchange resin column (100–200 mesh, Cl-form) and lyophilization, the title compound was obtained as a white powder (23 mg).

Analysis calculated for $C_{40}H_{64}N_6O_2S_2 \cdot 5.0$ HCl$\cdot 2.7$ H$_2$O: C, 50.25; H, 7.84; N; Found: C, 50.26; H, 7.70; N, 8.76.

Example 5

1-[2(R)-Methylamino-3-mercaptopropyl]-2(S)-n-butyl-4-(2,3-dimethylbenzoyl)piperazine dihydrochloride Step A

1-[2(R)-N-tert-Butoxycarbonyl-N-methylamino-3-triphenylmethylthiopropyl]-2(S)-n-butyl-4-(2,3-dimethylbenzoyl)piperazine 1-[2(R)-N-tert-Butoxycarbonylamino-3-triphenylmethylthiopropyl]-2(S)-n-butyl-4-(2,3-dimethylbenzoyl)piperazine (0.238 g, 0.337 mmol) was dissolved in dimethylformamide (7 mL) and cooled to 0° C. under nitrogen. Sodium hydride (40 mg, 60% dispersion in oil, 1.00 mmol) and methyl iodide (0.050 mL, 0.74 mmol) were added and the reaction stirred for 2.25 h. The reaction was quenched with water and partitioned between ethyl acetate and water. The organic phase was washed with three portions of water, saturated sodium chloride solution and dried over magnesium sulfate. The crude product was chromatographed on silica gel with 30% ethyl acetate in hexane. The title compound was obtained as a clear oil (177 mg).

Step B

1-[2(R)-Methylamino-3-mercaptopropyl)-2(S)-n-butyl-4-(2,3-dimethylbenzoyl)piperazine dihydrochloride The title compound was obtained according to the procedure described for Step E, Example 1 except using 1-[2(R)-N-tert-butoxycarbonyl-N-methylamino-3-triphenylmethylthiopropyl]-2(S)-n-butyl-4-(2,3-dimethylbenzoyl)piperazine (0.170 g, 0.236 mmol), triethylsilane (0.150 mL, 0.944 mmol) and trifluoroacetic acid (3 mL) in methylene chloride (6 mL). Purification by preparative HPLC (gradient elution: 85% Solvent A to 55% Solvent A/45% Solvent B, 70 min) and ion exchange provided the title compound as a white powder (47 mg).

Analysis calculated for $C_{21}H_{35}N_3OS \cdot 2.8$ HCl: C, 52.58; H, 7.94; N; 8.76. Found: C, 52.64; H, 7.93; N, 8.67.

Example 6

1-[2(R)-Amino-3-mercaptopropyl]-2(S)-benzyl-4-(2,3-dimethylbenzoyl)piperazine dihydrochloride Step A

1,3(S)-Dibenzylpiperazine-2,5-dione

The title compound was prepared according to the procedure described in Example 2, Step A, except using Boc-L-phenylalanine (12.8 g, 48.2 mmol), ethyl N-benzylglycinate (9.32 g, 48.2 mmol) and dicyclohexylcarbodiimide (96.5 mL 0.5M in dichloromethane, 48.2 mmol). The crude diketopiperazine was triturated with hexane to give the title compound as a white powder (12.5 g). NMR (300 MHz, CD$_3$OD) δ 7.0–7.4 (10H, m), 4.61 (1H, d, J=16 Hz), 4.37 (1H, t, J=5 Hz), 4.24 (1H, d, J=16 Hz), 3.42 (1H, d, J=18 Hz), 3.28 (1H, dd, J=4, 16 Hz), 2.96 (1H, dd, J=6, 16 Hz), 2.55 (1H, d, J=18 Hz).

Step B

1-tert-Butoxycarbonyl-2(S),4-dibenzylpiperazine

The title compound was prepared according to the procedure described in Example 2, Step B, except using 1,3(S)-dibenzylpiperazine-2,5-dione (5.01 g, 17.1 mmol) and lithium aluminum hydride (2.33 g, 61.4 mmol), followed by di-tert-butyl dicarbonate (4.02 g, 18.4 mmol). The crude product was purified by column chromatography on silica gel, eluting with 7.5% ethyl acetate in hexane. The title compound was obtained as a white solid (4.78 g). NMR (300 MHz, $CD_3OD$) δ 7.2–7.4 (5H, m), 7.0–7.2 (5H, m), 4.15 (1H, m), 3.90 (1H, d, J=15 Hz), 3.60 (1H, d, J=15 Hz), 3.15 (1H, m), 2.95 (3H, m), 2.7 (1H, d, J=13 Hz), 2.02 (1H, dt, J=6, 13 Hz), 1.95 (1H, br d), 1.35 (9H, s).

Step C

2(S)-Benzyl-1-tert-butoxycarbonylpiperazine

The title compound was prepared according to the procedure described in Example 2, Step C, except using 1-tert-butoxycarbonyl-2(S),4-dibenzylpiperazine (4.78 g, 11.3 mmol) and 10% palladium on carbon (1.04 g). The title compound was obtained as an oil. NMR (300 MHz, $CD_3OD$) δ 7.25 (5H, m), 4.35 (1H, m), 4.00 (1H, d, J=12 Hz), 2.7–3.3 (7H, m), 1.25 (9H, s).

Step D

2(S)-Benzyl-1-tert-butoxycarbonyl-4-(2,3-dimethylbenzoyl)piperazine

The title compound was prepared according to the procedure described for Example 1, Step A except using 2(S)-benzyl-1-tert-butoxycarbonylpiperazine (0.292 g, 1.06 mmol), 2,3-dimethyl-benzoic acid (0.159 g, 1.06 mmol), HOBT (0.157 g, 1.02 mmol), EDC.HCl (0.213 g, 1.11 mmol) and triethylamine to adjust the pH to 7. The title compound was obtained as a thick oil (0.416 g). NMR (DMSO-$d_6$, 300 MHz) δ 7.15 (2H, m), 6.06 (1H,m), 4.42 (1H,m), 3.6– 4.2 (2H, m), 2.7–3.24 (4H, m), 2.24 (3H, s), 2.03–2.20 (3H, 4s), 1.10–1.6 (15H, m), 0.72–1.00 (3H, m).

Step E

2(S)-Benzyl-1-[2(R)-N-tert-butoxycarbonylamino-3-triphenylmethylthiopropyl]-4-(2,3-dimethylbenzoyl)-piperazine The title compound was prepared according to the procedure described in Example 1, Step D, except using (2S)-benzyl-1-tert-butoxycarbonyl-4-(2,3-dimethylbenzoyl) piperazine (0.416 g, 1.01 mmol) and trifluoroacetic acid (3.5 mL) in methylene chloride (10 mL). The trifluoroacetate salt was reacted with (R)-2-N-tert-butoxycarbonylamino-3-triphenylmethylthiopropanal (0.547 g, 1.22 mmol), sodium triacetoxyborohydride (0.969 g, 4.58 mmol) in the presence of crushed molecular sieves in dichloroethane. The title compound was isolated after chromatography on silica gel with 30% ethyl acetate in hexane (0.415 g).

Step F

1-[2(R)-Amino-3-mercaptopropyl]-2(S)-benzyl-4-(2,3-dimethylbenzoyl)piperazine dihydrochloride The title compound was obtained according to the procedure described for Step E, Example 1 except using 2(S)-benzyl-1-[2(R)-N-tert-butoxycarbonylamino-3-triphenylmethylthiopropyl]-4-(2,3-dimethylbenzoyl)-piperazine (0.415 g, 0.562 mmol), triethylsilane (0.359 mL, 2.25 mmol) and trifluoroacetic acid (4.5 mL) in methylene chloride (9 mL). Purification by preparative HPLC (gradient elution: 90% Solvent A to 30% Solvent A/70% Solvent B, 55 min) and ion exchange provided the title compound as a white powder (78 mg).

Analysis calculated for $C_{23}H_{31}N_3OS \cdot 2.85$ HCl: C, 55.13; H, 6.81; N, 8.39. Found: C, 55.15; H, 6.73; N, 8.30.

Example 7

1-[2(R)-Amino-3-mercaptopropyl]-4-(2,3-dimethylbenzoyl)-2(S)-(2-methoxyethyl)piperazine dihydrochloride Step A 1-Benzyl-3(S)-cyclohexoxycarbonylmethylpiperazine-2,5-dione The title compound was prepared according to the procedure described in Example 2, Step A, except using Boc-L-aspartic acid, β-cyclohexyl ester (6.15 g, 19.5 mmol), ethyl N-benzylglycinate (3.76 g, 19.5 mmol) and dicyclohexylcarbodiimide (39 mL, 0.5M in dichloromethane, 19.5 mmol). The title compound was obtained as a white powder (6.8 g). NMR ($CD_3OD$, 300 MHz) δ 7.3 (5H, m), 4.77 (1H, d, J=15 Hz), 4.73 (1H, m), 4.48 (1H, d, J=15 Hz), 4.35 (1H, t, J=5 Hz), 3.96 (1H, dd, J=1, 17 Hz), 3.87 (1H, dd, J=1, 17 Hz), 3.06 (1H, dd, J=4, 17 Hz), 2.81 (1H, dd, J=5, 17 Hz), 1.78 (4H, m), 1.54 (1H, m), 1.35 (5H, m).

Step B

4-Benzyl-1-tert-butoxycarbonyl-2(S)-(2-hydroxyethyl)piperazine

The title compound was prepared according to the procedure described in Example 2, Step B, except using 1-benzyl-3(S)-cyclohexoxycarbonylmethylpiperazine-2,5-dione (1.5 g, 4.36 mmol) and lithium aluminum hydride (0.76 g, 20.1 mmol), followed by di-tert-butyl dicarbonate (1.04 g, 4.77 mmol). The crude product was purified by column chromatography on silica gel, eluting with 30% ethyl acetate in hexane. The title compound was obtained as a clear oil, 1.27 g. NMR ($CD_3OD$, 300 MHz) δ 7.3 (5H, m), 4.20 (1H, m), 3.86 (1H, dm, J=13 Hz), 3.55 (1H, d, J=13 Hz), 3.46 (2H, m), 3.39 (1H, d, J=13 Hz), 3.08 (1H, t, J=12 Hz), 2.80 (1H, d, J=12 Hz), 2.73 (1H, d, J=12 Hz), 2.04 (3H, m), 1.84 (1H, sextet, J=7 Hz), 1.45 (9H, s).

Step C

4-Benzyl-1-tert-butoxycarbonyl-2(S)-(2-methoxyethyl)piperazine

A solution of 4-benzyl-1-tert-butoxycarbonyl-2(S)-(2-hydroxyethyl)piperazine (0.322 g, 1.00 mmol) in dry, degassed dimethylformamide (4 mL) was cooled under nitrogen to 0° C. Sodium hydride was added (0.052 g, 60% dispersion in oil, 1.30 mmol) followed by methyl iodide (0.88 mL, 1.41 mmol). After 3 h, the reaction was quenched with saturated ammonium chloride. The solvent was removed in vacuo and the residue partitioned between ethyl acetate and saturated sodium bicarbonate. The ethyl acetate was washed with water, saturated sodium chloride solution, and dried over magnesium sulfate. The crude product was chromatographed on silica gel with 40% ethyl acetate in hexane to obtain the title compound as a clear oil (280 mg). NMR ($CD_3OD$, 300 MHz) δ 7.3 (5H, m), 4.19 (1H, m), 3.85 (1H, dm, J=13 Hz), 3.56 (1H, d, J=13 Hz), 3.16 (1H, d, J=13 Hz), 3.28 (2H, m, partially obscured by solvent), 3.23 (3H, s), 3.08 (1H, t, J=13 Hz), 2.80 (1H, d, J=11 Hz), 2.70 (1H, d, J=11 Hz), 2.03 (3H, m), 1.86, (1H, sextet, J=6 Hz), 1.45 (9H, s).

Step D 1-tert-Butoxycarbonyl-2(S)-(2-methoxyethyl)piperazine

The title compound was prepared according to the procedure described in Example 2, Step C, except using 4-benzyl-1-tert-butoxycarbonyl-2(S)-(2-methoxyethyl) piperazine (0.280 g, 0.83 mmol) and 10% palladium on carbon (80 mg). The title compound was obtained as an oil (179 mg). NMR (CD$_3$OD, 300 MHz) δ 4.17 (1H, m), 3.81 (1H, dd, J=3, 13 Hz), 3.38 (2H, t, J=6 Hz), 2.82–3.02 (2H, m), 2.77 (2H, ABq, J=4, 13 Hz), 2.59 (1H, dt, J=4, 7 Hz), 2.04 (1H, m), 1.84 (1H, m), 1.46 (9H, s).

Step E 1-tert-Butoxycarbonyl-4-(2,3-dimethylbenzoyl)-2(S)
-(2-methoxyethyl)piperazine The title compound was prepared according to the procedure described for Example 1, Step A except using 1-tert-butoxycarbonyl-2(S)-(2-methoxyethyl)piperazine (0.179 g, 0.73 mmol), 2,3-dimethylbenzoic acid (0.115 g, 0.75 mmol), HOBT (0.098 g, 0.73 mmol), EDC.HCl (0.153 g, 0.80 mmol) in methylene chloride (5 mL). Triethylamine was added to adjust the pH to 7. Chromatography on silica gel with 40% ethyl acetate in hexane afforded the title compound as a clear oil (0.222 g). NMR (CDCl$_3$, 300 MHz) δ 6.9–7.2 (5H, m), 4.70 (1H, m), 3.8–4.5 (9H, mm), 2.0–2.3 (6H, mm), 1.9 (2H, m), 1.59 (9H, s).

Step F

1-[2(R)-N-tert-Butoxycarbonylamino-3-
triphenylmethylthiopropyl]-4-(2,3-dimethylbenzoyl)
-2(S)-(2-methoxyethyl)piperazine The title compound was prepared according to the procedure described in Example 1, Step D, except using 1-tert-butoxycarbonyl-4-(2,3-dimethylbenzoyl)-2(S)-(2-methoxyethyl)piperazine (0.222 g, 0.590 mmol) and trifluoroacetic acid (3 mL) in methylene chloride (7 mL). The trifluoroacetate salt was reacted with 2(R)-N-tert-butoxycarbonylamino-3-triphenylmethylthiopropanal (0.316 g, 0.710 mmol), sodium triacetoxyborohydride (0.565 g, 2.65 mmol) in the presence of crushed molecular sieves in dichloroethane. The title compound was isolated after chromatography on silica gel with 50% ethyl acetate in hexane (0.247 g).

Step G

1-[2(R)-Amino-3-mercaptopropyl]-4-(2,3-
dimethylbenzoyl)-2(S)-(2-methoxyethyl)piperazine
dihydrochloride The title compound was obtained according to the procedure described for Step E, Example 1 except using 1-[2(R)-N-tert-butoxycarbonylamino-3-triphenylmethylthiopropyl]-4-(2,3-dimethylbenzoyl)-2(S)-(2-methoxyethyl)piperazine (0.247 g, 0.349 mmol), triethylsilane (0.22 mL, 1.39 mmol) and trifluoroacetic acid (3.5 mL) in methylene chloride (7 mL). Purification by preparative HPLC (gradient elution: 95% Solvent A to 30% Solvent A/70% Solvent B, 60 min) and ion exchange provided the title compound as a white powder (0.088 g).

Analysis calculated for C$_{19}$H$_{31}$N$_3$OS.3.80 HCl.0.6 H$_2$O: C, 44.39; H, 7.06; N, 8.17. Found: C, 44.46; H, 7.07; N, 8.00.

Example 8

1-[2(R)-Amino-3-mercaptopropyl]-4-(2,3-
dimethylbenzoyl)-2(S)-(2-methylthioethyl)
piperazine dihydrochloride Step A 1-Benzyl-3(S)-(2-methylthioethyl)piperazine-2,5-
dione The title compound was prepared according to the procedure described in Example 2, Step A, except using Boc-L-methionine (10.0 g, 40.0 mmol), ethyl N-benzylglycinate (7.75 g, 40.0 mmol), HOBT (5.41 g, 40.0 mmol) and EDC.HCl (7.68 g, 40.00 mmol) in dimethylformamide. Upon completion of the reaction, the dimethylformamide was removed in vacuo and the crude product partitioned between ethyl acetate and water. The organic phase was washed with water and saturated sodium chloride solution, then dried over sodium sulfate. The solvent was removed in vacuo and the residue taken up in methylene chloride (200 mL). Trifluoroacetic acid (100 mL) was added and the reaction stirred at 20° C. for 2 h. The volatiles were removed in vacuo and the residue partitioned between ethyl acetate and saturated sodium bicarbonate solution. The organic phase was washed with saturated sodium chloride solution and dried over magnesium sulfate. The title compound was obtained as a white solid (9.08 g). NMR (CHCl$_3$, 300 MHz) δ 7.4–7.2 (6H, m); 4.60 (2H, AB q, J=13 Hz); 4.24 (1H, m); 3.85 (2H, AB q, J=18 Hz); 2.63 (2H, t, J=7Hz); 2.3–2.1 (2H, m); 2.1 (3H, s).

Step B

4-Benzyl-1-tert-butoxycarbonyl-2(S)-(2-
methylthioethyl)piperazine

The title compound was prepared according to the procedure described in Example 2, Step B, except using 1-benzyl-3(S)-(2-methylthioethyl)piperazine-2,5-dione (9.08 g, 32.6 mmol) and lithium aluminum hydride (4.40 g, 0.115 mmol), followed by di-tert-butyl dicarbonate (7.64 g, 35.0 mmol). The crude product was purified by column chromatography on silica gel, eluting with 5% ethyl acetate in hexane. The title compound was obtained as a clear oil (6.73 g). NMR (CHCl$_3$, 300 MHz) δ 7.35–7.25 (5H, m); 4.18 (1H, br s); 3.90 (1H, br d); 3.55 (1H, d, J=13Hz); 3.40 (1H, d, J=13Hz); 3.07 (1H, t, J=12 Hz); 2.72 (2H, m); 2.40 (2H, m); 2.10 (3H, s); 1.48 (9H, s).

Step C 1-tert-Butoxycarbonyl-2(S)-(2-methylthioxethyl)
piperazine

To a solution of the product from Step B (6.63 g, 18.9 mmol) in 20 mL methylene chloride was added 2.15 mL (20 mmol) of 1-chloroethyl chloroformate (ACE-Cl) dropwise with stirring. The temperature rose from 25° C. to 32° C. After 90 min was added another 0.20 mL of ACE-Cl and 2.4 g of solid potassium carbonate. After 90 min the mixture was diluted with ethyl acetate and washed successively with 10% sodium bicarbonate and brine. The solution was dried (sodium sulfate) and evaporated to afford 8.4 g of an oil. The oil was dissolved in 500 mL methanol. The mixture was stirred at room temperature for 3 h and placed in the refrigerator overnight. The solution was treated with 100 mL of water and the methanol was evaporated. The solution was washed with ethyl acetate to remove nonbasic impurities. The aqueous phase was neutralized with 10% sodium bicarbonate and extracted with methylene chloride. The extract was dried (potassium carbonate) and evaporated to give 4.0 g of 1-tert-butoxycarbonyl-2(S)-(2-methylthioethyl) piperazine. NMR (CHCl$_3$, 300 MHz) δ 4.17 (1H, br s); 3.89 (1H, br d); 2.92 (4H, m); 2.70 (1H, dt, J=4,12 Hz); 2.6–2.4 (2H, m); 2.10 (3H, s); 1.88 (1H, m); 1.48 (9H,s).

Step D 1-tert-Butoxycarbonyl-4-(2,3-dimethylbenzoyl)-2(S)
-(2-methylthioethyl)piperazine The title compound was prepared according to the procedure described for Example 1, Step A except using 1-tertbutoxycarbonyl-2(S)-(2-methylthioethyl)piperazine (1.87 g, 7.19 mmol), 2,3-dimethylbenzoic acid (1.08 g, 7.19 mmol), HOBT (0.970 g, 7.19 mmol), EDC.HCl (1.64 g, 8.62 mmol) in methylene chloride (50 mL). Triethylamine was added to adjust the pH to 7. Chromatography on silica gel with 30% ethyl acetate in hexane afforded the title compound as a clear oil (2.51 g). NMR (DMSO-$d_6$, 300 MHz) δ 6.9–7.3 (3H, m), 4.22–4.50 (2H, mm), 3.62–4.06 (2H, mm), 2.66–3.24 (4H, mm), 2.4 (1H, m), 2.24 (3H, s), 1.92–2.18 (6H, ms),1.4–1.8 (2H, m), 1.39 (9H, s).

Step E

1-[2(R)-N-tert-Butoxycarbonylamino-3-triphenylmethylthiopropyl]-4-(2,3-dimethylbenzoyl)-2(S)-(2-methylthioethyl)piperazine The title compound was prepared according to the procedure described in Example 1, Step D, except using 1-tert-butoxycarbonyl-4-(2,3-dimethylbenzoyl)-2(S)-(2-methylthioethyl)piperazine (0.465 g, 1.18 mmol) and trifluoroacetic acid (3 mL) in methylene chloride (7 mL). The trifluoroacetate salt was reacted with 2(R)-N-tert-butoxycarbonylamino-3-triphenylmethylthiopropanal (0.400 g, 0.890 mmol), sodium triacetoxyborohydride (0.302 g, 1.42 mmol) in the presence of crushed molecular sieves in dichloroethane. The title compound (0.465 g) was isolated as a foam after chromatography on silica gel with 50% ethyl acetate in hexane.

Step F

4-[2(R)-Amino-3-mercaptopropyl]-1-(2,3-dimethylbenzoyl)-2(S)-(2-methylthioethyl)piperazine dihydrochloride The title compound was obtained according to the procedure described for Step E, Example 1 except using 1-[2(R)-N-tert-butoxycarbonylamino-3-triphenylmethylthiopropyl]-4-(2,3-dimethylbenzoyl)-2(S)-(2-methylthioethyl)piperazine (0.465 g, 0.656 mmol), triethylsilane (0.420 mL, 2.63 mmol) and trifluoroacetic acid (3.5 mL) in methylene chloride (7 mL). Purification by preparative HPLC (gradient elution: 95% Solvent A to 20% Solvent A/80% Solvent B, 60 min) and ion exchange provided the title compound as a white powder (0.213 g).

Analysis calculated for $C_{19}H_{31}N_3OS_2$.2.80 HCl.0.8 $H_2O$: C, 45.85; H, 7.17; N, 8.44. Found: C, 45.85; H, 7.14; N, 8.32.

Example 9

1-[2(R)-Amino-3-mercaptopropyl]-4-(2,3-dimethylbenzoyl)-2(S)-(2-methylsulfonylethyl)piperazine dihydrochloride Step A 1-tert-Butoxycarbonyl-4-(2,3-dimethylbenzoyl)-2(S)-(2-methylsulfonylethyl)piperazine m-Chloroperoxybenzoic acid (2.0 g, 5.77 mmol) and potassium acetate (1.00 g, 10.2 mmol) in chloroform (30 mL) was cooled to 0° C. A solution of 1-tert-butoxycarbonyl-4-(2,3-dimethylbenzoyl)-2(S)-(2-methylthioethyl)piperazine from Step D, Example 8 (0.906 g, 2.31 mmol) in methanol (20 mL) was added dropwise. The solution was stirred for 6 h at 20° C. The reaction was extracted with 10% sodium thiosulfate, 5% sodium hydroxide and saturated sodium chloride solution. The crude product was chromatographed on silica gel with 60% ethyl acetate in hexane. The title compound was obtained as a foam (0.799 g). NMR (CD$_3$OD, 300 MHz) δ 6.9–7.3 (3H, m), 4.4–4.7 (2H, mm), 3.8–4.2 (2H, mm), 2.8–3.4 (9H, mm), 2.04–2.35 (7H, mm), 1.47 (9H, s).

Step B

1-[2(R)-N-tert-butoxycarbonylamino-3-triphenylmethylthiopropyl]-4-(2,3-dimethylbenzoyl)-2(S)-(2-methylsulfonylethyl)piperazine The title compound was prepared according to the procedure described in Example 1, Step D, except using 1-tert-butoxycarbonyl-4-(2,3-dimethylbenzoyl)-2(S)-(2-methylsulfonylethyl)piperazine (0.400 g, 0.94 mmol) and trifluoroacetic acid (3 mL) in methylene chloride (7 mL). The trifluoroacetate salt was reacted with 2(R)-N-tert-butoxycarbonylamino-3-triphenylmethylthiopropanal (0.420 g, 0.940 mmol), sodium triacetoxyborohydride (0.240 g, 1.12 mmol) in the presence of crushed molecular sieves in dichloroethane. The title compound (0.305 g) was isolated as a foam after chromatography on silica gel with 60% ethyl acetate in hexane.

Step C

1-[2(R)-Amino-3-mercaptopropyl]-4-(2,3-dimethylbenzoyl)-2(S)-(2-methylsulfonylethyl)piperazine dihydrochloride The title compound was obtained according to the procedure described for Step E, Example 1 except using 1-[2(R)-N-tert-butoxycarbonylamino-3-triphenylmethylthiopropyl]-4-(2,3-dimethylbenzoyl)-2(S)-(2-methylsulfonylethyl)piperazine (0.300 g, 0.397 mmol), triethylsilane (0.253 mL, 1.59 mmol) and trifluoroacetic acid (3.5 mL) in methylene chloride (7 mL). Purification by preparative HPLC (gradient elution: 100% Solvent A to 40% Solvent A/60% Solvent B, 60 min) and ion exchange provided the title compound as a white powder (0.150 g).

Analysis calculated for $C_{19}H_{31}N_3O_3S_2$.3.10 HCl.1.1 $H_2O$: C, 41.80; H, 6.70; N, 7.70. Found: C, 41.79; H, 6.84; N, 7.56.

Example 10

1-[2(R)-Amino-3-mercaptopropionyl]-2(S)-n-butyl-4-(2,3-dimethyl-benzoyl)piperazine hydrochloride Step A 1-[2(R)-tert-Butoxycarbonylamino-3-triphenylmethylthiopropionyl]-2(S)-n-butyl-4-(2,3-dimethylbenzoyl)piperazine 3(S)-n-Butyl-1-(2,3-dimethylbenzoyl)piperazine (0.240 g, 0.874 mmol) and 2(R)-tert-butoxycarbonylamino-3-triphenylmethylthiopropionic acid (0.405 g, 0.874 mmol) were dissolved in dimethylformamide. To this solution was added HOBT (0.114 g, 0.874 mmol), and EDC.HCl (0.184 g, 0.962 mmol). The reaction was stirred under nitrogen overnight. The dimethylformamide was removed in vacuo and the residue partitioned between ethyl acetate and water. The organic phase was washed with several portions of water, saturated sodium chloride solution, and dried over magnesium sulfate. Filtration and evaporation of solvent gave the crude product, which was chromatographed on silica gel with 50% ethyl acetate in hexane. The title compound as a white foam (0.620 g).

Step B

1-[2(R)-Amino-3-mercaptopropionyl]-2(S)-n-butyl-4-(2,3-dimethylbenzoyl)piperazine hydrochloride The product from Step A (0.620 g, 0.86 mmol) was dissoved in methylene chloride (12 mL) and triethylsilane (0.550 mL, 3.44 mmol) was added followed by trifluoroacetic acid (6 mL). After 2 h at 20° C. the volatiles were removed in vacuo and the residue partitioned between hexane and water. The aqueous phase was injected onto a 40×100 mm Waters PrepPak® reverse phase HPLC column (Delta-Pak™ $C_{18}$ 15 μm, 100 Å), and pure product isolated by gradient elution using 85% Solvent A (0.1% trifluoroacetic acid in water) to 50% Solvent A/50% Solvent B (0.1% trifluoroacetic acid in acetonitrile). Combined fractions were evaporated, dissolved in water and passed through a Biorad AG® 3×4 ion exchange resin column (100–200 mesh, Cl-form). The column eluant was lyophilized to give the title compound as a white powder (0.146 g).

Analysis calculated for $C_{20}H_{31}N_3O_2S.HCl.1.2H_2O$: C, 55.14; H, 7.96; N; 9.65. Found: C, 55.09; H, 8.17; N, 9.56.

Example 11

4-[2(R)-Amino-3-mercaptopropyl]-2(S)-n-butyl-1-(2,3-dimethyl-benzoyl)piperazine dihydrochloride Step A 4-Benzyl-2(S)-n-butyl-1-(2,3-dimethylbenzoyl)piperazine Trifluoroacetic acid (4.5 mL) was added to a solution of 4-benzyl-1-tert-butoxycarbonyl-2(S)-n-butylpiperazine (0.507 g, 1.52 mmol) in methylene chloride (9 mL), and the reaction stirred for 2 h at 20° C. The volatiles were removed in vacuo and the residue partitioned between ethyl acetate and saturated sodium bicarbonate solution. The organic phase was washed with saturated sodium chloride solution and dried over magnesium sulfate. The crude product was dissolved in dry, degassed dimethylformamide (18 mL) and 2,3-dimethylbenzoic acid (0.229 g, 1.53 mmol), HOBT (0.222 g, 1.45 mmol), and EDC.HCl (0.307 g, 1.60 mmol) added. The pH was adjusted to 8 by the addition of triethylamine. The reaction was stirred at 20° C. overnight, and the dimethylformamide removed in vacuo. The residue was partitioned between ethyl acetate and saturated sodium bicarbonate solution. The organic phase was washed with saturated sodium chloride solution and dried over magnesium sulfate. The solvent was removed in vacuo to give the title compound.

Step B

2(S)-n-Butyl-1-(2,3-dimethylbenzoyl)piperazine

4-Benzyl-2(S)-n-butyl-1-(2,3-dimethylbenzoyl)piperazine (0.93 g, 2.55 mmol) was dissolved in methanol and hydrogenated in a Parr apparatus under 60 psi hydrogen in the presence of 10% Pd/C (0.186 g) for 24 h. The catalyst was removed by filtration through Celite, and the solvent removed in vacuo to obtain the title compound (0.818 g).

Step C

4-[2(R)-tert-Butoxycarbonylamino-3-triphenylmethylthiopropyl]-2(S)-n-butyl-1-(2,3-dimethylbenzoyl)piperazine The title compound was prepared according to the procedure described in Example 1, Step D, except using 2(S)-n-butyl-1-(2,3-dimethylbenzoyl)piperazine (0.818 g, 1.53 mmol), sodium triacetoxyborohydride (1.46 g, 6.88 mmol), crushed molecular sieves (1 g), and (R)-2-N-tert-butoxycarbonylamino-3-triphenylmethylthiopropanal (0.822 g, 1.84 mmol) in dichloroethane. The title compound was obtained as an oil (1.28 g).

Step D

4-[2(R)-Amino-3-mercaptopropyl]-2(S)-n-butyl-1-(2,3-dimethylbenzoyl)piperazine dihydrochloride The title compound was prepared according to the procedure described in Example 1, Step E except using 4-[2(R)-tert-butoxycarbonylamino-3-triphenylmethylthiopropyl]-2-(S)n-butyl-1-(2,3-dimethylbenzoyl)piperazine (1.28 g, 1.81 mmol), triethylsilane (1.16 mL, 7.24 mmol), and trifluoroacetic acid (8 mL) in dichloromethane (16 mL). The crude product was purified by preparative HPLC (gradient: 100% Solvent A to 50% Solvent A/50% Solvent B). After ion exchange and lyophilization, the title compound was obtained as a white powder (0.127 g).

Analysis calculated for $C_{20}H_{33}N_3OS.2.9$ HCl.0.95 $H_2O$: C, 49.43; H, 7.84; N, 8.65. Found: C, 49.38; H, 7.88; N, 8.51.

Example 12

1-[2(R)-Amino-3-mercaptopropyl]-4-(1-naphthoyl)-2(S)-(2-methoxyethyl)piperazine dihydrochloride Step A 4-Benzyl-1-[2(R)-tert-butoxycarbonylamino-3-triphenylmethylthiopropyl]-2(S)-(2-methoxyethyl)piperazine 4-Benzyl-1-tert-butoxycarbonyl-2(S)-(2-methoxyethyl)piperazine from Example 7, step C (1.17 g, 3.50 mmol) was dissolved in methylene chloride (20 mL). To this solution was added trifluoroacetic acid (10 mL) and the reaction stirred at 20° C. for 1 h. The volatiles were removed in vacuo and the residue taken up in dichloroethane (40 mL). Triethylamine was added to attain pH 7. To this solution was added crushed molecular seives (1 g), sodium triacetoxyborohydride (1.2 g, 5.3 mmol) and the reaction cooled to −15° C. with ice-methanol. A solution of 2(R)-tert-butoxycarbonylamino-3-triphenylmethylthiopropanal (1.72 g, 3.85 mmol) in dichloroethane (15 mL) was added slowly dropwise. The reaction was stirred at 20° C. overnight then quenched with saturated sodium bicarbonate. The organic phase was washed with saturated sodium chloride solution, and dried over magnesium sulfate. The crude product (2.52 g) was chromatographed on silica gel with 30% ethyl acetate in hexane using medium pressure liquid chromatography (MPLC). The title compound ($R_f$ 0.21) was isolated as a gum (0.906 g). NMR (CHCl$_3$, 300 MHz) δ 7.2–7.4 (20H, m), 4.70 (1H, d, J=8 Hz), 3.63 (1H, br s), 3.50 (1H, d, J=13 Hz), 3.36 (1H, d, J=13 Hz), 3.2–3.35 (5H, m), 2.75 (1H, m), 2.0–2.6 (10H, m), 1.75 (2H, m), 1.42 (9H, s). A diastereomeric minor product ($R_f$ 0.14) was also isolated (0.065 g).

Step B

1-[2(R)-tert-Butoxycarbonylamino-3-triphenylmethylthiopropyl]-2(S)-(2-methoxyethyl)piperazine The title compound was obtained by treating the product of step A (0.884 g, 1.33 mmol) with 1-chloroethyl chloroformate (0.151 mL, 1.39 mL) and potassium carbonate (0.200 g, 1.45 mmol) in dichloromethane (15 mL) according to the procedure described in Example 8, step C. The crude product was chromatographed on silica gel with 5–10% methanol in chloroform. The title compound was isolated as a foam (0.705 g). NMR (CHCl$_3$, 300 MHz) δ 5 7.2–7.45 (15H, m), 4.66 (1H, d, J=8 Hz), 3.65 (1H, m), 3.35 (2H, m), 3.28 (3H, s), 2.94 (1H, dd, J=12, 3 Hz), 1.7–2.9 (13H, m), 1.42 (9H, s).

Step C

1-[2(R)-tert-Butoxycarbonylamino-3-triphenylmethylthiopropyl]-2(S)-(2-methoxyethyl)-4-(1-naphthoyl)-piperazine The title compound was prepared from the product of Step B (0.422 g, 0.733 mmol), 1-naphthoic acid (0.120 mg, 0.698 mmol), EDC.HCl (0.154 mg, 0.806 mmol), HOBT (0.099 g, 0.733 mmol) in DMF at pH 7 according to the procedure described in Example 1, Step A. The crude product was chromatographed on silica gel with 30–40% ethyl acetate in hexane ($R_f$ 0.50, 40% ethyl acetate/hexane). The title compound (0.50 g) was isolated as a gum.

Step D

1-[2(R)-Ammo-3-mercaptopropyl]-2(S)-(2-methoxyethyl)-4-(1-naphthoyl)piperazine dihydrochloride The title compound was prepared from the product of Step C (0.438 g, 0.600 mmol), triethylsilane (0.383 mL, 2.4 mmol), trifluoroacetic acid (10 mL) in dichloromethane (20 mL) according to the procedure described in Example 1, Step E. The crude product was purified by preparative HPLC (gradient: 85% Solvent A/15% Solvent B to 65% Solvent A/35% Solvent B). After ion exchange and lyophilization, the title compound was obtained as a white powder (0.214 g).

Analysis calculated for $C_{21}H_{29}N_3O_2S \cdot 2.95$ HCl $\cdot 0.05$ $H_2O$: C, 50.85; H, 6.51; N, 8.47. Found: C, 50.86; H, 6.12; N, 8.31.

Example 13

1-[2(R)-Amino-3-mercaptopropyl]-2(S)-(2-(1-propoxy)ethyl)-4-(1-naphthoyl)piperazine dihydrochloride

Step A

1-tert-butoxycarbonyl-2(S)-(2-hydroxyethyl) piperazine

4-Benzyl-1-tert-butoxycarbonyl-2(S)-(2-hydroxyethyl) piperazine (7.0 g, 21.8 mmol) was hydrogenated at 60 psi in methanol (80 mL) in the presence of 10% Pd/C (1.56 g) according to the procedure described in Example 2, Step C. The title compound was obtained as an oil (4.43 g). NMR ($CD_3OD$, 300 MHz) δ 4.17 (1H, m), 3.80 (1H, d, J=4 Hz), 3.54 (2H, t, J=7Hz), 2.75–3.05 (4H, m), 2.58 (1H, dt, J=4, 13 Hz), 2.0 (1H, m), 1.8 (1H, m), 1.45 (9H, s).

Step B

1-tert-butoxycarbonyl-2(S)-(2-hydroxyethyl)-4-(1-naphthoyl)piperazine

1-Naphthoic acid (0.374 g, 2.17 mmol), EDC.HCl (0.416 g, 2.17 mmol), HOBT (0.333 g, 2.17 mmol) in DMF at pH 7 (adjusted with triethylamine) was stirred at 20° C. for 10 min. The product from Step A (0.500 g, 2.17 mmol) was added and the reaction stirred overnight. DMF was removed in vacuo, and the residue partitioned between ethyl acetate and saturated sodium bicarbonate solution. The organic phase was washed with saturated sodium chloride solution, then dried over magnesium sulfate. The crude product was chromatographed on silica gel with 5% methanol in chloroform. The title compound was obtained as a foam, (0.760 g).

Step C

1-tert-butoxycarbonyl-2(S)-(2-(1-propoxy)ethyl)-4-(1-naphthoyl)piperazine

The product from Step B was reacted with sodium hydride (0.220 g, 60% dispersion in oil, 5.4 mmol) and n-propyl iodide (0.375 mL, 3.85 mmol) according to the procedure described in Example 7, Step C. The crude product was chromatographed on silica gel with 30% ethyl acetate in hexane. The title compound was obtained as a foam, (0.400 g).

Step D

1-[2(R)-tert-Butoxycarbonylamino-3-triphenylmethyl-thiopropyl]-2(S)-(2-(1-propoxy)ethyl)-4-(1-naphthoyl)piperazine The product of Step C was first treated with trifluoroacetic acid (10 mL) in dichloromethane (10 mL); the crude trifluoroacetate salt was then reacted with sodium triacetoxyborohydride (0.795 g, 3.76 mmol), 2(R)-tert-butoxycarbonylamino-3-triphenylmethylthiopropanal (0.504 g, 1.13 mmol) in dichloroethane (15 mL) in the presence of crushed molecular sieves following the procedure described in Example 1, Step D. The title compound was obtained as a gum (0.715 g).

Step E

1-[2(R)-Amino-3-mercaptopropyl]-2(S)-(2-(1-propoxy)ethyl)-4-(1-naphthoyl)piperazine dihydrochloride The title compound was prepared from the product of Step D (0.715 g, 0.94 mmol), triethylsilane (0.600 mL, 3.7 mmol), trifluoroacetic acid (10 mL) in dichloromethane (20 mL) according to the procedure described in Example 1, Step E. The crude product was purified by preparative HPLC (gradient: 85% Solvent A/15% Solvent B to 60% Solvent A/40% Solvent B). After ion exchange and lyophilization, the title compound was obtained as a white powder (0.115 g), FAB mass spectrum m/e 416 (m+1).

Analysis calculated for $C_{23}H_{35}N_3O_2S \cdot 2.7$ HCl $\cdot 0.6H_2O$: C, 52.67; H, 7.09; N, 8.01. Found: C, 52.65; H, 7.07; N, 8.01.

Example 14

1-[2(R)-Amino-3-mercaptopropyl]-2(S)-(2-(3-pyridylmethoxy)ethyl)-4-(1-naphthoyl)piperazine trihydrochloride

Step A

1-tert-Butoxycarbonyl-2(S)-(2-(3-pyridylmethoxy)ethyl)-4-(1-naphthoyl)piperazine 1-tert-Butoxycarbonyl-2(S)-(2-hydroxyethyl)-4-(1-naphthoyl)piperazine (0.300 g, 0.780 mmol) was reacted with sodium hydride (0.312 g, 60% dispersion in oil, 7.8 mmol) and 3-chloromethylpyridine (0.497 g, 3.9 mmol) according to the procedure described in Example 7, Step C. The crude product was chromatographed on silica gel with 3% methanol in chloroform. The title compound was obtained as an oil, (0.180 g).

Step B

1-[2(R)-tert-Butoxycarbonylamino-3-triphenylmethylthiopropyl]-2(S)-(2-(3-pyridylmethoxy)ethyl)-4-(1-naphthoyl)piperazine The product of Step A (0.180 g, 0.39 mmol) was first treated with trifluoroacetic acid (10 mL) in dichloromethane (10 mL); the crude trifluoroacetate salt was then reacted with sodium triacetoxyborohydride (0.330 g, 1.56 mmol), 2(R)-tert-butoxycarbonylamino-3-triphenylmethylthiopropanal (0.227 g, 0.507 mmol) in dichloroethane (15 mL) in the presence of crushed molecular sieves following the procedure described in Example 1, Step D. The title compound was obtained as a gum (0.330 g).

Step C

1-[2(R)-Amino-3-mercaptopropyl]-2(S)-(2-(3-pyridylmethoxy)ethyl)-4-(1-naphthoyl)piperazine trihydrochloride The title compound was prepared from the product of Step B (0.330 g, 0.4 mmol), triethylsilane (0.254 mL, 1.6 mmol), trifluoroacetic acid (10 mL) in dichloromethane (20 mL) according to the procedure described in Example 1, Step E. The crude product was purified by preparative HPLC (gradient: 95% Solvent A/5% Solvent B to 70% Solvent A/30% Solvent B). After ion exchange and lyophilization, the title compound was obtained as a hydroscopic white powder, FAB mass spectrum m/e 465 (m+1).

Analysis calculated for $C_{26}H_{35}N_4O_2S.4.6$ HCl.1.8 $H_2O$: C, 47.03; H, 6.10; N, 8.44. Found: C, 47.00; H, 6.10; N, 8.62.

Example 15

1-[2(R)-Amino-3-mercaptopropyl]-2(S)-(2-(1-propoxy)ethyl)-4-(8-quinolinylcarbonyl)piperazine trihydrochloride Step A 1-tert-butoxycarbonyl-2(S)-(2-hydroxyethyl)-4-(8-quinolinylcarbonyl)piperazine 8-Quinoline carboxylic acid (1.00 g, 5.78 mmol), EDC.HCl (1.22 g, 6.38 mmol), HOBT (1.77 g, 13.1 mmol) in DMF at pH 7 (adjusted with triethylamine) was stirred at 20° C. for 15 min. 1-tert-Butoxycarbonyl-2(S)-(2-hydroxyethyl)piperazine (1.33 g, 6.71 mmol) was added and the reaction stirred overnight. DMF was removed in vacuo, and the residue taken up in 1:1:1 THF, methanol, and 5% aqueous sodium hydroxide. This was stirred at 20° C. for 72 h. The volatiles were removed in vacuo, and the residue partitioned between ethyl acetate and saturated sodium bicarbonate solution. The organic phase was washed with saturated sodium chloride solution, then dried over magnesium sulfate. The title compound was obtained as a foam (1.2 g).

Step B 1-tert-butoxycarbonyl-2(S)-(2-(1-propoxy)ethyl)-4-(8-quinolinylcarbonyl)piperazine The product from Step A (0.300 g, 0.779 mmol) was reacted with sodium hydride (0.125 g, 60% dispersion in oil, 3.1 mmol) and n-propyl iodide (0.456 mL, 4.67 mmol) according to the procedure described in Example 7, Step C. The crude product was chromatographed on silica gel with 3% methanol in chloroform. The title compound was obtained as an oil, (0.320 g).

Step C

1-[2(R)-tert-Butoxycarbonylamino-3-triphenylmethylthiopropyl]-2(S)-(2-(1-propoxy)ethyl)-4-(8-quinolinylcarbonyl)piperazine The product of Step B (0.330 g, 0.772 mmol) was first treated with trifluoroacetic acid (10 mL) in dichloromethane (10 mL); the crude trifluoroacetate salt was then reacted with sodium triacetoxyborohydride (0.653 g, 3.09 mmol), 2(R)-tert-butoxycarbonylamino-3-triphenylmethylthiopropanal (0.415 g, 0.927 mmol) in dichloroethane (15 mL) in the presence of crashed molecular sieves following the procedure described in Example 1, Step D. The title compound was obtained as a gum (0.572 g).

Step D

1-[2(R)-Amino-3-mercaptopropyl]-2(S)-(2-(1-propoxy)ethyl)-4-(8-quinolinylcarbonyl)piperazine trihydrochloride The title compound was prepared from the product of Step C (0.572 g, 0.75 mmol), triethylsilane (0.480 mL, 3.0 mmol), trifluoroacetic acid (10 mL) in dichloromethane (20 mL) according to the procedure described in Example 1, Step E. The crude product was purified by preparative HPLC (gradient: 95% Solvent A/5% Solvent B to 65% Solvent A/35% Solvent B). After ion exchange and lyophilization, the title compound was obtained as a white powder (0.132 g), FAB mass spectrum m/e 417 (m+1).

Analysis calculated for $C_{22}H_{35}N_4O_2S.3.6HCl.0.6H_2O$: C, 47.32; H, 6.54; N, 10.03. Found: C, 47.26; H, 6.63; N, 10.09.

Example 16

1-[2(R)-Amino-3-mercaptopropyl]-2(S)-n-butyl-4-(1-naphthoyl)piperazine dihydrochloride Step A 1-tert-butoxycarbonyl-2(S)-n-butyl-4-(1-naphthoyl) piperazine The title compound was prepared according to the procedure described in Example 1, Step A except using 1-tert-butoxycarbonyl-2(S)-n-butylpiperazine (0.325 g, 1.34 mmol), 1-naphthalene carboxylic acid (0.230 g, 1.34 mmol), HOBT (0.203 g, 1.34 mmol), EDC.HCl (0.254 g, 1.34 mmol) and triethylamine to adjust the pH to 7. The title compound was obtained as a thick oil (0.490 g).

Step B

1-[2(R)-N-tert-Butoxycarbonylamino-3-triphenylmethylthiopropyl]-2(S)-n-butyl-4-(1-naphthoyl)piperazine The title compound was prepared according to the procedure described in Example 1, Step D, except using 1-tert-butoxycarbonyl-2(S)-n-butyl-4-(1-naphthoyl)piperazine (0.336 g, 0.861 mmol) and trifluoroacetic acid (10 mL) in methylene chloride (10 mL). The crude trifluoroacetate salt was reacted with 2(R)-tert-butoxycarbonylamino-3-triphenylmethylthiopropanal (0.350 g, 0.763 mmol), sodium triacetoxyborohydride (0.546 g, 2.58 mmol) in the presence of crushed molecular sieves in dichloroethane (20 mL). Triethylamine was added to adjust the pH to 6. The crude product was chromatographed on silica gel with 30% ethyl acetate in hexane, and the title compounds isolated as a foam (0.230 g).

Step C

1-[2(R)-Amino-3-mercaptopropyl]-2(S)-n-butyl-4-(1-naphthoyl)piperazine dihydrochloride The title compound was obtained according to the procedure described in Example 1, Step E except using 1-[2(R)-N-tert-butoxycarbonylamino-3-triphenylmethylthiopropyl]-2(S)-n-butyl-4-(1-naphthoyl)

piperazine. (0.230 g, 0.32 mmol), triethylsilane (0.200 mL, 1.27 mmol) and trifluoroacetic acid (10 mL) in methylene chloride (10 mL). Purification by preparative HPLC (gradient elution: 85% Solvent A to 50% Solvent A/50% Solvent B) and ion exchange provided the major product as a white powder (0.052 g), FAB mass spectrum m/e 386 (m+1).

Analysis calculated for $C_{22}H_{33}N_3OS.2.7$ HCl.0.1 $H_2O$: C, 54.43; H, 7.04; N; 8.66. Found: C, 54.40; H, 7.01, N; 8.75.

Example 17

1-[2(R)-Amino-3-mercaptopropyl]-2(S)-n-butyl-4-[7-(2,3-dihydrobenzofuranoyl)]piperazine dihydrochloride Step A 2,3-Dihydrobenzofuran-7-carboxylic acid A solution of dihydrocoumarin (0.338 mL, 3.00 mmol) in dry diethyl ether (10 mL) was cooled to −78° C. and a solution of n-butyllithium in hexane (2.38M, 1.30 mL, 3.00 mmol) was slowly added. The reaction was stirred at 20° C. overnight. The reaction was cooled to −78° C. and carbon dioxide was bubbled through for 10 min. The reaction was warmed to 20° C. and partitioned between water and ether. A solution of 10% aqueous HCl was added to the aqueous phase until the pH was less than 1. The aqueous phase was washed with ether, and the ether washed with saturated sodium chloride solution. The title compound was obtained as a white solid (0.175 g). NMR (CDCl$_3$, 300 MHz) δ 7.83 (1H, d, J=8 Hz), 7.42 (1H, d, J=8 Hz), 6.96 (1H, t, J=8 Hz), 4.80 (2H, t, J=8 Hz), 3.30 (2H, t, J=8 Hz).

Step B 1-tert-Butoxycarbonyl-2(S)-n-butyl-4-[7-(2,3-dihydrobenzofuranoyl)]piperazine The title compound was prepared according to the procedure described in Example 1, Step A except using 1-tert-butoxycarbonyl-2(S)-n-butylpiperazine (0.146 g, 0.60 mmol), 2,3-dihydrobenzofuran-7-carboxylic acid (0.085 g, 0.518 mmol), HOBT (0.092 g, 0.60 mmol), EDC.HCl (0.115 g, 0.60 mmol) and triethylamine to adjust the pH to 7. The title compound was obtained as a thick oil (0.230 g).

Step C

1-[2(R)-N-tert-Butoxycarbonylamino-3-triphenylmethylthiopropyl]-2(S)-n-butyl-4-[7-(2,3-dihydrobenzofuranoyl)]piperazine The title compound was prepared according to the procedure described in Example 1, Step D, except using 1-tert-butoxycarbonyl-2(S)-n-butyl-4-[7-(2,3dihydrobenzofuranoyl)]piperazine (0.230 g, 0.591 mmol) and trifluoroacetic acid (10 mL) in methylene chloride (10 mL). The crude trifluoroacetate salt was reacted with 2(R)-N-tert-butoxycarbonylamino-3-triphenylmethylthiopropanal (0.300 g, 0.670 mmol), sodium triacetoxyborohydride (0.500 g, 2.36 mmol) in the presence of crushed molecular sieves in dichloroethane (20 mL). Triethylamine was added to adjust the pH to 6. The title compound was isolated as a foam (0.375 g).

Step D

1-[2(R)-Amino-3-mercaptopropyl]-2(S)-n-butyl-4-[7-(2,3-dihydrobenzofuranoyl)]piperazine dihydrochloride The title compound was obtained according to the procedure described in Example 1, Step E except using 1-[2 (R)-N-tert-butoxycarbonylamino-3-triphenylmethylthiopropyl]-2(S)-n-butyl-4-[7-(2,3-dihydrobenzofuranoyl)]piperazine. (0.375 g, 0.54 mmol), triethylsilane (0.344 mL, 2.16 mmol) and trifluoroacetic acid (10 mL) in methylene chloride (10 mL). Purification by preparative HPLC (gradient elution: 85% Solvent A to 65% Solvent A/35% Solvent B) and ion exchange provided the major product as a white powder (0.023 g), FAB mass spectrum m/e 378 (m+1).

Analysis calculated for $C_{20}H_{33}N_3OS.2.9$ HCl.0.1$H_2O$: C, 49.56; H, 7.09; N; 8.67. Found: C, 49.63; H, 7.05, N; 9.03.

Example 18

1-[2(R)-Amino-3-mercaptopropyl]-4-(1-naphthoyl)-2(S)-(3-methoxy-1-propyl)piperazine dihydrochloride Step A 1-Benzyl-3(S)-cyclohexoxycarbonylethylpiperazine-2,5-dione The title compound was prepared according to the procedure described in Step A, Example 2, except using Boc-L-glutamic acid, γ-cyclohexyl ester (15.0 g, 44.4 mmol), ethyl N-benzylglycinate (8.58 g, 44.6 mmol) and dicyclohexylcarbodiimide (89 mL, 0.5M in dichloromethane, 44.6 mmol). The crude product was deprotected and cyclized as described in Example 2, Step A and the crude product was obtained as a white solid (18.0 g). This was recrystallized from hexane/ethyl acetate to obtain the title compound as a white solid (13.9 g). NMR (CDCl$_3$, 300 MHz) δ 7.3 (5H, m), 6.79 (1H, bs), 5.10 (2H, s), 4.65 (1H, d, J=15 Hz), 4.53 (1H, d, J=15 Hz), 4.12 (1H, m), 3.82 (2H, AB q, J=20 Hz, D n=24 Hz), 2.55 (2H, m), 2.23 (2H, m), 1.7 (1H, d, J=12 Hz).

Step B

4-Benzyl-1-tert-butoxycarbonyl-2(S)-(3-hydroxy-1-propyl)piperazine

The title compound was prepared according to the procedure described in Example 2, Step B, except using 1-benzyl-3(S)-cyclohexoxycarbonylethylpiperazine-2,5-dione (13.9g, 38.8 mmol) and lithium aluminum hydride (7.8 g, 0.205 mol); the crude product was treated with di-tert-butyl dicarbonate (10.4 g, 47.7 mmol). The crude product was purified by column chromatography on silica gel, eluting with 50% ethyl acetate in hexane. The title compound was obtained as a clear oil, 3.5 g. NMR (CDCl$_3$, 300 MHz) a 7.3 (5H, m), 4.10 (1H, bs), 3.85 (1H, bs), 3.65 (2H, dd, J=3, 6 Hz), 3.52 (1H, d, J=13 Hz), 3.38 (1H, d, J=13 Hz), 3.05 (1H, t, J=12 Hz), 2.75 (1H, d, J=12 Hz), 2.68 (1H, dd, J=10 Hz) 2.00 (5H, m), 1.70 (2H, m), 1.44 (9H, s).

Step C

4-Benzyl-1-tert-butoxycarbonyl-2(S)-(3-methoxy-1-propyl)piperazine

The title compound was prepared according to the procedure described in Example 7, Step C, except using 4-benzyl-1-tert-butoxycarbonyl-2(S)-(3-hydroxy-1-propyl) piperazine (1.02 g, 3.05 mmol), sodium hydride (0.183 g, 60% dispersion in oil, 4.58 mmol), and methyl iodide (0.247 mL, 3.97 mmol) in DMF (6 mL). The crude product was chromatographed on silica gel with 30% ethyl acetate in hexane to obtain the title compound as a clear oil (0.870 g). NMR (CDCl$_3$, 300 MHz) δ 7.3 (5H, m), 4.05 (1H, m), 3.85 (1H, m), 3.46 (2H, AB q, J=12 Hz, D n=42 Hz), 3.39 (1H, m), 3.22 (3H, s), 3.04 (1H, t, J=13 Hz), 2.74 (1H, d, J=12 Hz), 2.66 (1H, d, J=12 Hz), 1.45–2.12 (7H, m), 1.44 (9H, s).

Step D

1-tert-Butoxycarbonyl-2(S)-(3-methoxy-1-propyl) piperazine

The title compound was prepared according to the procedure described in Example 2, Step C, except using 4-benzyl-1-tert-butoxycarbonyl-2(S)-(3-methoxy-1-propyl) piperazine (0.870 g, 2.50 mmol) and 10% palladium on carbon (200 mg). The title compound was obtained as an oil (0.450 g). NMR (CDCl$_3$, 300 MHz) δ 4.05 (1H, m), 3.85 (1H, m), 3.40 (2H, m), 3.35 (3H, s), 2.90 (5H, m), 2.70 (1H, dt, J=4, 7 Hz), 1.50–2.0 (4H, m), 1.45 (9H, s).

Step E

1-tert-Butoxycarbonyl-2(S)-(3-methoxy-1-propyl)-4-(1-naphthoyl)-piperazine

The title compound was prepared according to the procedure described for Example 1, Step A except using 1-tert-butoxycarbonyl-2(S)-(3-methoxypropyl)piperazine (0.215 g, 0.832 mmol), naphthalene-1-carboxylic acid (0.143 g, 0.83 mmol), HOBT (0.128 g, 0.83 mmol), EDC.HCl (0.160 g, 0.83 mmol) in DMF (5 mL). The title compound was obtained as an oil (0.310 g).

Step F

1-[2(R)-N-tert-Butoxycarbonylamino-3-triphenylmethyl-thiopropyl]-2(S)-(3-methoxy-1-propyl)-4-(1-naphthoyl)piperazine The title compound was prepared according to the procedure described in Example 1, Step D, except using 1-tert-butoxycarbonyl-2(S)-(3-methoxy-1-propyl)-4-(1-naphthoyl)piperazine (0.260 g, 0.652 mmol) and trifluoroacetic acid (10 mL) in methylene chloride (10 mL). The trifluoroacetate salt was reacted with 2(R)-N-tert-butoxycarbonylamino-3-triphenylmethylthiopropanal (0.350 g, 0.782 mmol), sodium triacetoxyborohydride (0.552 g, 2.62 mmol) in the presence of crushed molecular sieves in dichloroethane. The title compound was obtained as an oil (0.331 g).

Step G

1-[2(R)-Amino-3-mercaptopropyl]-2(S)-(3-methoxy-1-propyl)-4-(1-naphthoyl)piperazine dihydrochloride The title compound was obtained according to the procedure described for Step E, Example 1 except using 1-[2(R)-N-tert-butoxycarbonylamino-3-triphenylmethylthiopropyl]-2(S)-(3-methoxy-1-propyl)-4-(1-naphthoyl)piperazine. (0.331 g, 0.454 mmol), triethylsilane (0.29 mL, 1.81 mmol) and trifluoroacetic acid (10 mL) in methylene chloride (10 mL). Purification by preparative HPLC (gradient elution: 85% Solvent A to 60% Solvent A/40% Solvent B) and ion exchange provided the title compound as a white powder (0.108 g). FAB mass spectrum m/e 388 (m+1).

Analysis calculated for C$_{21}$H$_{31}$N$_3$O$_2$S.3.0 HCl.0.1 H$_2$O: C, 50.62; H, 6.51; N, 8.43. Found: C, 50.64; H, 6.41; N, 8.32.

Example 19

1-(2(R)-Amino-3-mercaptopropyl)-2(S)-n-butyl-4-(8-quinolinylcarbonyl)piperazine trihydrochloride

Step A

1-tert-butoxycarbonyl-2(S)-n-butyl-4-(8-quinolinylcarbonyl)piperazine

The title compound was prepared according to the procedure described in Example 1, Step A, except using 1-tert-butoxycarbonyl-2(S)-n-butyl-piperazine (0.261 g, 1.078 mmol), 8-quinoline carboxylic acid (0.187 g, 1.078 mmol), EDC.HCl (0.217 g, 1.13 mmol), HOBT (0.157g, 1.02 mmol) in DMF at pH 7 (adjusted with triethylamine). The crude product was chromatographed on silica gel with 5% methanol in chloroform. The title compound was obtained as an oil (0.253 g).

Step B

1-[2(R)-tert-Butoxycarbonylamino-3-triphenylmethyl-thiopropyl]-2(S)-n-butyl-4-(8-quinolinylcarbonyl)piperazine The product of Step A (0.253 g, 0.637 mmol) was first treated with trifluoroacetic acid (5 mL) in dichloromethane (10 mL); the crude trifluoroacetate salt was then reacted with sodium triacetoxyborohydride (0.608 g, 2.87 mmol), (R)-2-N-tert-butoxycarbonylamino-3-triphenylmethylthiopropanal (0.342 g, 0.766 mmol) in dichloroethane in the presence of crushed molecular sieves following the procedure described in Example 1, Step D. The title compound was obtained as a gum (0.54 g).

Step C

1-[2(R)-Amino-3-mercaptopropyl]-2(S)-n-butyl-4-(8-quinolinylcarbonyl)piperazine trihydrochloride The title compound was prepared from the product of Step B (0.54 g), triethylsilane (0.473 mL, 2.9 mmol), trifluoroacetic acid (5 mL) in dichloromethane (10 mL) according to the procedure described in Example 1, Step E. The crude product was purified by preparative HPLC (gradient: 85% Solvent A/15% Solvent B to 65% Solvent A/35% Solvent B). After ion exchange and lyophilization, the title compound was obtained as a white powder (0.080 g). FAB mass spectrum m/e 387 (m+1).

Analysis calculated for C$_{21}$H$_{30}$N$_4$OS.3 HCl: C, 50.86; H, 6.71; N, 11.30. Found: C, 50.77; H, 6.81; N, 11.26.

Example 20

1-[2(R)-Amino-3-mercaptopropyl]-4-naphthoyl-2(S)-(2-phenylsulfonylethyl)piperazine dihydrochloride

Step A

1-tert-Butoxycarbonyl-2(S)-(2-hydroxy-ethyl)-4-naphthoylpiperazine

To a solution of 1-tert-butoxycarbonyl-2(S)-(2-hydroxyethyl)piperazine (0.479 g, 2.08 mmol) in DMF was added EDC.HCl (0.432 g, 2.25 mmol), HOBT (0.314 g, 2.05 mmol) and naphthalene-2-carboxylic acid (0.353 g, 2.05 mmol). Triethylamine was added to pH 7. The reaction was stirred overnight at room temperature. The DMF was removed in vacuo and the residue dissolved in 1:1 methanol-tetrahydrofuran and 5% sodium hydroxide added. The reaction was stirred several hours, the solvent evaporated and the residue partitioned between ethyl acetate and 5% sodium hydroxide. The organic phase was dried over magnesium sulfate and the crude product thus obtained chromatoraphed on silica gel with 50% ethyl acetate in hexane. The title compound was obtained as a white foam.

Step B

1-tert-Butoxycarbonyl-2(S)-(2-phenylthioethyl)-4-naphthoylpiperazine

The product from Step A (0.806 g, 2.09 mmol) was dissolved in tetrahydrofuran (dry) under nitrogen. Diphenyl disulfide (0.915 g, 4.19 mmol) and tributylphosphine (0.848 g, 4.19 mmol) were added and the reaction stirred at room temperature until complete. The solvent was removed in vacuo and the residue partitioned between ethyl acetate and 5% sodium hydroxide. The organic phase was washed with brine and dried over magnesium sulfate. The crude product was chromatographed on silica gel with 25–30% ethyl acetate in hexane and the title compound was isolated (0.77 g).

Step C

1-tert-Butoxycarbonyl-4-naphthoyl-2(S)-(2-phenylsufonylethyl)piperazine

The product from Step B (0.77 g, 1.61 mmol) was dissolved in methanol and the solution cooled to 0° C. A solution of monoperoxyphthalic acid, magnesium salt hexahydrate (2.39 g, 4.85 mmol) in methanol was added dropwise. The ice bath was removed and the reaction stirred for several hours until complete. A 10% aqueous solution of sodium thiosulfate (5 mL) was added and the reaction stirred at 0° C. until starch-KI paper tests negative. The solvent was evaporated and the residue partitioned between ethyl acetate and saturated sodium bicarbonate solution. The organic phase was washed with brine and dried over magnesium sulfate. Filtration and evaporation gave the title compound (1.13 g). m/e 509 (m+1).

Step D

1-[2(R)-N-tert-Butoxycarbonylamino-3-triphenylmethylthiopropyl]-4-naphthoyl-2(S)-(2-phenylsulfonylethyl)piperazine The title compound was prepared according to the procedure described in Example 1, Step D, except using 1-tert-butoxycarbonyl-4-naphthoyl-2(S)-(2-phenylsufonylethyl)piperazine (0.312 g, 0.614 mmol) and trifluoroacetic acid (3.5 mL) in methylene chloride (10 mL). The trifluoroacetate salt was reacted with (R)-2-N-tert-butoxycarbonylamino-3-triphenylmethyl-thiopropanal (0.330 g, 0.737 mmol), sodium triacetoxyborohydride (0.585 g, 2.77 mmol) in the presence of crushed molecular sieves in dichloroethane. The title compound was isolated after chromatography on silica gel with 50% ethyl acetate in hexane.

Step E

1-[2(R)-Amino-3-mercaptopropyl]-4-naphthoyl-2(S)-(2-phenylsulfonylethyl)piperazine dihydrochloride The title compound was obtained according to the procedure described for Step E, Example 1 except using 1-[2(R)-N-tert-butoxycarbonylamino-3-triphenylmethylthiopropyl]-4-naphthoyl-2(S)-(2-phenylsulfonylethyl)piperazine (0.200 g, 0.238 mmol), triethylsilane (0.146 mL, 0.953 mmol) and trifluoroacetic acid (4.5 mL) in methylene chloride (9 mL). Purification by preparative HPLC (gradient elution: 85% Solvent A to 45% Solvent A/55% Solvent B, 55 min) and ion exchange provided the title compound as a white powder (70 mg).

Analysis calculated for $C_{26}H_{31}N_3O_3S_2$.2.20 HCl: C, 52.81; H, 5.92; N, 7.11. Found: C, 52.84; H, 5.92; N, 7.04.

Example 21 bis-1, 1'-[2(R)-Amino-3-(2(S)-(2-methoxyethyl)-4-naphthoyl-1-piperazinyl)]propyl disulfide tetrahydrochloride A solution of iodine in methanol was added to a solution of 1-[2(R)-amino-3-mercaptopropyl]-2(S)-(2-methoxyethyl)-4-naphthoylpiperazine dihydrochloride (68 mg, 0.139 mmol) in methanol (15 mL) until a slight yellow color persisted. The solvent was evaporated and the crude product dissolved in methanol-water and purified by preparative HPLC using a gradient elution of 85% Solvent A to 25% Solvent A/75% Solvent B over 60 min. After ion exchange with Biorad AG® 3×4 ion exchange resin column (100–200 mesh, Cl-form) and lyophilization, the title compound was obtained as a white powder (38 mg).

Analysis calculated for $C_{42}H_{56}N_6O_4S_2$.5.1 HCl.1.8 $H_2O$: C, 50.91; H, 6.58; N; 8.48. Found: C, 50.90; H, 6.57; N, 8.53.

Example 22 bis-1,1'-[2(R)-Amino-3-(-4-naphthoyl-2(S)-(2-phenylsulfonylethyl)-1-piperazinyl)]propyl disulfide tetrahydrochloride A solution of iodine in methanol is added to a solution of 1-[2(R)-Amino-3-mercaptopropyl]-4-naphthoyl-2(S)-(2-phenylsulfonyl-ethyl)piperazine dihydrochloride in methanol (15 mL) until a slight yellow color persists. The solvent is evaporated and the crude product is dissolved in methanol-water and purified by preparative HPLC using a gradient elution of 85% Solvent A to 25% Solvent A/75% Solvent B over 60 min. After ion exchange with Biorad AG® 3×4 ion exchange resin column (100–200 mesh, Cl-form) and lyophilization, the title compound is obtained as a white powder.

Analysis calculated for $C_{52}H_{60}N_6O_6S_4$.4 HCl: C, 54.83; H, 5.66; N; 7.38.

Example 23

1-(2(R)-Amino-3-mercaptopropyl)-4-(5,6,7,8-tetrahydronaphth-1-yl)piperazine trihydrochloride Step A

1-(5,6,7,8-Tetrahydronaphth-1-yl)piperazine dihydrochloride

A mixture of 1-amino-5,6,7,8-tetrahydronaphthalene (2.44 g, 16.60 mmol) and bis-(2-chloroethyl)amine hydrochloride (2.69 g, 15.09 mmol) in n-butanol (15 mL) was heated at reflux under nitrogen for 3 d. The reaction was cooled to 20° C. The white precipitate was collected by filtration and washed with n-butanol, then dried under vacuum. The title compound was obtained as a white solid (1.64 g). NMR (300 MHz, $CD_3OD$) δ 7.1 (1H, t, J=8 Hz), 6.9 (1H, d, J=8 Hz), 6.15 (1H, d, J=8 Hz), 3.35 (4H, m), 3.1 (4H, m), 2.75 (4H, m), 1.8 (4m).

Step B

1-(2(R)-tert-Butoxycarbonylamino-3-triphenylmethyl-thiopropyl)-4-(5,6,7,8-tetrahydronaphth-1-yl)piperazine The title compound was prepared according to the procedure described in Example 1, Step D, except using 1-(5,6,7,8-tetrahydronaphth-1-yl)piperazine dihydrochloride (0.484 g, 1.67 mmol), 2(R)-N-tert-butoxycarbonylamino-3-triphenylmethylthiopropanal (0.500 g, 1.12 mmol), sodium triacetoxyborohydride (0.473 g, 2.24 mmol), dimethylformamide (8 mL) and crushed molecular sieves (1 g). The title compound was obtained as a gum.

Step C

1-(2(R)-Amino-3-mercaptopropyl)-4-(5,6,7,8-tetrahydronaphth-1-yl)piperazine trihydrochloride The title compound was prepared according to the procedure described in Example 1, Step E, except using 1-(2

(R)- tert-butoxycarbonylamino-3-triphenylmethyl-thiopropyl)-4-(5,6,7,8-tetrahydronaphth-1-yl)piperazine obtained in Step B above, triethylsilane (0.71 mL, 4.48 mmol), trifluoroacetic acid (6 mL) and dichloromethane (12 mL). Purification by preparative HPLC using gradient elution (100% Solvent A to 40% Solvent A/60% Solvent B over 60 min), ion exchange and lyophilization afforded the title compound as a white powder (89 mg).

Analysis calculated for $C_{17}H_{27}N_3S.3$ HCl: C, 49.22; H, 7.29; N, 10.13. Found: C, 49.28; H, 7.26; N, 10.09.

Example 24

1-(2(R)-Amino-3-mercaptopropyl)-4-benzyl-2(S)-n-butylpiperazin-5-one dihydrochloride Step A N-Methoxy-N-methyl 2(R)-tert-butoxycarbonylaminohexanamide The title compound was prepared according to the procedure described in Example 1, Step A except using 2(S)-t-butoxycarbonylaminohexanoic acid (10.6 g, 0.045 mol), N, O-dimethylhydroxylamine hydrochloride (4.69 g, 0.048 mol), EDC.HCl (9.45 g, 0.049 mol), HOBT (6.18 g, 0.045 mol), DMF (200 mL) and triethylamine at pH 7. The crude product was chromatographed on silica gel with 15–20% ethyl acetate in hexane. The title compound was obtained as an oil. NMR (DMSO-$d_6$, 300 MHz) δ 7.01 (1H, d, J=8 Hz), 4.34 (1H, q, J=5 Hz), 7.72 (3H, s), 3.09 (3H, s), 1.50 (2H, m), 1.36 (9H, s), 1.17 (3H, m), 0.85 (3H, t, J=6 Hz).

Step B

2(R)-tert-Butoxycarbonylaminohexanal

The title compound was prepareded according to the procedure described in Example 1, Step C, except using N-methoxy-N-methyl 2(R)-tert-butoxycarbonylaminohexanamide (4.08 g, 14.89 mmol), lithium aluminum hydride (0.621 g, 16.37 mmol), in ether (200 mL), followed by potassium hydrogen sulfate (4.05 g, 29.78 mmol) workup. The title compound was obtained as a clear oil, 3.28 g. NMR (CDCl$_3$, 300 MHz) δ 9.6 (1H, s), 5.04 (1H, bs), 4.23 (1H, m), 1.15–2.0 (15H, m), 0.9 (3H, m).

Step C

N-Benzyl 2(R)-tert-butoxycarbonylaminohexyl-1-amine

The title compound was obtained according to the procedure described in Example 1, Step D, except using 2(R)-tert-butoxycarbonylaminohexanal (0.555 g, 2.58 mmol), benzylamine (0.422 mL, 3.87 mmol), sodium triacetoxyborohydride (0.824 g, 3.87 mmol) in dichlorethane (10 mL). Acetic acid was added to pH 6. The crude product was chromatographed on silica gel with 3% methanol in chloroform. The title compound was obtained as a clear oil (0.625 g). NMR (CDCl$_3$, 300 MHz) δ 7.31 (5H, m), 4.60 (1H, m), 3.79 (2H, AB q, J=24 Hz, Δv=24 Hz), 3.65 (1H, m), 2.68 (1H, AB q, J=12, 5 Hz), 2.62 (1H, AB q, J=13, 8 Hz), 1.2–1.5 (16H, m), 0.89 (3H, t, J=7 Hz).

Step D

4-Benzyl-1-tert-butoxycarbonyl-2(S)-n-butylpiperazin-5-one

A solution of N-benzyl 2(R)-tert-butoxycarbonylaminohexyl-1-amine (0.615 g, 2.00 mmol) in ethyl acetate (10 mL) was cooled to 0° C. Saturated sodium bicarbonate (10 mL) was added, and the well-stirred solution kept at 0° C. while bromoacetyl bromide (0.175 mL, 2.00 mmol) was added dropwise. The reaction was stirred for 15 min following the addition. The reaction was diluted with ethyl acetate and extracted with water, then saturated sodium chloride solution. The organic phase was dried over magnesium sulfate. Filtration and evaporation gave a clear, colorless foam, 0.816 g, which was dissolved in dry, degassed DMF (2 mL). This DMF solution was added to a suspension of sodium hydride (0.092 g, 60% dispersion in oil, 2.29 mmol) in DMF (10 mL), at 0° C. under an atmosphere of nitrogen. The reaction was stirred for 30 min, then water (5 mL) was added. The DMF was removed under high vacuum, and the residue partitioned between ethyl acetate and water. The ethyl acetate was washed with saturated sodium chloride solution, then dried over magnesium sulfate. The crude product was chromatographed on silica gel with 20–30% ethyl acetate in hexane. The title compound was obtained as a clear gum (0.498 g). NMR (CDCl$_3$, 300 MHz) δ 7.3 (5H, m), 4.95 (1H, m), 4.05 (1H, d, J=18 Hz), 4.22 (2H, br s), 3.78 (1H, d, J=18 Hz), 3.82 (1H, dd, J=12, 4 Hz), 3.00 (1H, d, J=12 Hz), 0.85–1.6 (15H, m), 0.80 (3H, t, J=7 Hz).

Step E

1-[2(R)-N-tert-Butoxycarbonylamino-3-triphenylmethylthiopropyl]-4-benzyl-2(S)-n butylpiperazin-5-one The title compound was prepared according to the procedure described in Example 1, Step D, except using 4benzyl-1 -tert-butoxycarbonyl-2(S)-n-butylpiperazin-5-one (0.281 g, 0.846 mmol) and trifluoroacetic acid (3 mL) in methylene chloride (6 mL). The trifluoroacetate salt was reacted with (R)-2-N-tert-butoxycarbonyl-amino-3-triphenylmethylthiopropanal (0.416 g, 0.931 mmol), sodium triacetoxyborohydride (0.270 g, 1.26 mmol) in the presence of crushed molecular sieves in dichloroethane. The crude product was chromatographed on silica gel with 30% ethyl acetate in hexane. The title compound was obtained as an oil (0.382 g).

Step F

1-[2(R)-Amino-3-mercaptopropyl]-4-benzyl-2(S)-n-butylpiperazin-5-one dihydrochloride The title compound was obtained according to the procedure described for Step E, Example 1 except using 1-[2(R)-N-tert-butoxycarbonylamino-3-triphenylmethylthiopropyl]-4-benzyl-2(S)-n butylpiperazin-5-one (0.382 g, 0.564 mmol), triethylsilane (0.36 mL, 2.25 mmol) and trifluoroacetic acid (5 mL) in methylene chloride (10 mL). Purification by preparative HPLC (gradient elution: 70% Solvent A to 30% Solvent A/70% Solvent B) and ion exchange provided the title compound as a white powder (0.074 g).

Analysis calculated for $C_{18}H_{29}N_3OS.2.0$ HCl.0.8 $H_2O$: C, 51.13; H, 7.77; N, 9.94. Found: C, 51.19; H, 7.61; N, 9.81.

Example 25

1-(2(R)-Amino-3-mercaptopropyl)-4-benzyl-2(S)-n-butylpiperazin-3-one dihydrochloride Step A N-Benzyl 2-aminoacetaldehyde diethyl acetal A solution of benzaldehyde (3.0 mL, 0.0295 mol) and 2-aminoacetaldehyde diethyl acetal (4.3 mL, 0.0295 mol) in dichloroethane (60 mL) was brought to pH 7 by the addition of acetic acid. Sodium triacetoxyborohydride (8.1 g, 0.038 mol) was added and the reaction stirred until complete. Saturated sodium bicarbonate was added and the reaction stirred for 30 min. Ethyl acetate was added and the organic phase washed with saturated sodium chloride, then dried over magnesium sulfate. The crude product was chromatographed on silica gel with 30% ethyl acetate in hexane. The title compound was obtained as a pale yellow oil (2.93 g). NMR (CDCl$_3$, 300 MHz) δ 7.31 (5H, m), 4.62 (1H, t, J=5 Hz), 3.81 (2H, s), 3.68 (2H, m), 3.54 (2H, m), 2.75 (2H d, J=5 Hz), 1.20 (6H, t, J=7 Hz).

Step B

N-Benzyl 2(R)-tert-butoxycarbonylaminohexanamide

The title compound was prepared according to the procedure described in Example 1, Step A except using 2(S)-t-butoxycarbonylaminohexanoic acid (1.98 g, 8.57 mmol), EDC.HCl (1.96 g, 10.28 mmol), N-benzyl 2-aminoacetaldehyde diethyl acetal (1.91 g, 8.57 mmol), HOBT (1.15 g, 8.57 mmol) in DMF. The title compound was obtained as a yellow oil.

Step C

1, 2, 3, 4-Tetrahydro-4-benzyl-1-tert-butoxycarbonyl-2(S)-n-butyl-3-oxopyrazine A solution of N-benzyl 2(R)-tert-butoxycarbonylaminohexanamide (1.0 g, 2.29 mmol) in THF (10 mL) was vigorously stirred with 6N HCl(10 mL) for 24h. Ethyl acetate was added, and the layers separated. The organic phase was washed with water, then saturated sodium chloride solution. The crude product was chromatographed on silica gel with 30% ethyl acetate in hexane. The title compound was obtained as an oil (0.140 g). NMR (CDCl$_3$, 300 MHz) δ 7.3 (5H, m), 6.31, 6.14 (1H, 2 ds, J=7, 7 Hz), 5.55, 5.42 (1H, 2 ds, J=7, 7 Hz), 4.68 (2H, AB q, J=15 Hz, D n=36 Hz), 4.78 (1H, m), 1.66 (2H, m), 1.47 (9H, d), 1.33 (4H, m), 0.89 (3H, brt, J=7 Hz).

Step D

4-Benzyl-1-tert-butoxycarbonyl-2(S)-n-butylpiperazin-3-one

A solution of 1, 2, 3, 4-tetrahydro-4-benzyl-1-tert-butoxycarbonyl-2(S)-n-butyl-3-oxopyrazine (0.140 g, 0.406 mmol) in methanol was stirred under 1 atmosphere of hydrogen in the presence of 10% palladium on carbon for 72 h. The catalyst was filtered and the crude product isolated as an oil (0.130 g). NMR (CDCl$_3$, 300 MHz) ⊖ 7.3 (5H, m), 4.88 (1H, br d, J=12 Hz), 4.62 (1H, br s), 4.30 (1H, br d, J=12 Hz), 4.10 (1H, br s), 3.35 (1H, m), 3.10 (2H, m), 2.01 (1H, m), 1.72 (1H, m), 1.45 (9H, s), 1.35 (4H, m), 0.82 (3H, t, J=7 Hz).

Step E

1-[2(R)-N-tert-Butoxycarbonylamino-3-triphenylmethyl-thiopropyl]-4-benzyl-2(S)-n butylpiperazin-5-one The title compound was prepared according to the procedure described in Example 1, Step D, except using 4-benzyl-1-tert-butoxycarbonyl-2(S)-n-butylpiperazin-3-one (0.130 g, 0.375 mmol) and trifluoroacetic acid (5 mL) in methylene chloride (10 mL). The trifluoroacetate salt was reacted with 2(R)-N-tert-butoxycarbonylamino-3-triphenylmethylthiopropanal (0.185 g, 0.413 mmol), sodium triacetoxyborohydride (0.317 g, 1.5 mmol) in the presence of crushed molecular sieves in dichloroethane. The crude product was obtained as a glass (0.310 g).

Step F

1-[2(R)-Amino-3-mercaptopropyl]-4-benzyl-2(S)-n-butylpiperazin-5-one dihydrochloride The title compound was obtained according to the procedure described for Step E, Example 1 except using 1-[2(R)-N-tert-butoxycarbonylamino-3-triphenylmethylthiopropyl]4-benzyl-2(S)-n butylpiperazin-5-one (0.375 mmol), triethylsilane (0.24 mL, 1.50 mmol) and trifluoroacetic acid (5 mL) in methylene chloride (10 mL). Purification by preparative HPLC (gradient elution: 85% Solvent A to 60% Solvent A/40% Solvent B) and ion exchange provided the title compound as a white powder (0.049 g). FAB mass spectrum m/e 336 (m+1).

Analysis calculated for C$_{18}$H$_{29}$N$_3$OS.2.2 HCl.0.1 H$_2$O: C, 51.79; H, 7.58; N, 10.07. Found: C, 51.84; H, 7.54; N, 10.08.

Example 26

1-[2(R)-Amino-3-mercaptopropyl]-4-naphthoyl-2(S)-(2-cyclopropyloxyethyl)piperazine dihydrochloride Step A

1-tert-Butoxycarbonyl-2(S)-(2-vinyloxyethyl)-4-(1-naphthoyl)piperazine 1-tert-Butoxycarbonyl-2(S)-(2-hydroxyethyl)-4-naphthoylpiperazine (0.50 g, 1.3 mmol) was dissolved in freshly distilled ethyl vinyl ether (20 mL) under argon. To this solution was added mercuric acetate (0.436 g, 1.37 mmol) and the reaction refluxed overnight. The reaction was cooled to room temperature, acetic acid added (0.035 mL, 0.58 mmol) and stirred 2 h. The reaction mixture was extracted with ethyl acetate and 5% aqueous sodium hydroxide, and the organic phase further extracted with saturated sodium chloride solution and dried over magnesium sulfate. The crude product was chromatographed on silica gel with 30% ethyl acetate in hexane. The title compound was obtained as a white solid.

Step B

1-tert-Butoxycarbonyl-2(S)-(2-cyclopropyloxyethyl)-4-(1-naphthoyl)piperazine 1-tert-Butoxycarbonyl-2(S)-(2-vinyloxyethyl)-4-naphthoylpiperazine (0.107 g, 0.261 mmol) was dissolved in ether (5 mL) under an argon atmosphere. To this solution was added diiodomethane (0.042 mL, 0.522 mmol) and diethylzinc (0.39 mL, 1M in hexane, 0.39 mmol). The reaction was refluxed for 1 h. The reaction was quenched with water, and extracted with ethyl acetate. The organic extracts were washed with water, saturated sodium chloride, and dried over magnesium sulfate. The title compound was obtained as an oil.

Step C

1-[2(R)-N-tert-Butoxycarbonylamino-3-triphenyl-methylthiopropyl]-2(S)-(2-cyclopropyloxyethyl)-4-(1-naphthoyl)piperazine The title compound was prepared according to the procedure described in Example 1, Step D. Thus, 1-tert-butoxycarbonyl-2(S)-(2-cyclopropyloxyethyl)-4-naphthoyl-piperazine was treated with 50% trifluoroacetic acid in methylene chloride for 1 h. The solvents were removed in vacuo, and the crude trifluoroacetate salt dissolved in dichloroethane (10 mL). To this solution was added sufficient triethylamine to attain pH 5, sodium triacetoxyborohydride (0.101 g, 0.227 mmol), crashed molecular sieves, and tert-butoxycarbonylamino-3-triphenyl-methylthiopropanal (0.160 g, 0.756 mmol), at 0° C. The title compound was obtained as a white foam.

Step D

1-[2(R)-Amino-3-mercaptopropyl]-4-(1-naphthoyl)-2 (S)-(2-cyclopropyloxyethyl)piperazine dihydrochloride The title compound was obtained according to the procedure described in Example 1, Step E, except using 1-[2(R)-N-tert-butoxycarbonylamino-3-triphenyl-methylthiopropyl]-2(S)-(2-cyclopropyl-oxyethyl)-4-naphthoylpiperazine (0.189 mmol), triethylsilane (0.116 mL, 0.756 mmol) and trifluoroacetic acid (10 mL) in methylene chloride (10 mL). Purification by preparative HPLC (gradient elution: 85% Solvent A to 60% Solvent A/40% Solvent B, 55 min) and ion exchange provided the title compound as a white powder. FAB MS m/e 414 (m+1).

Analysis calculated for $C_{23}H_{31}$ $N_3O_2S.3.20$ HCl: C, 52.15; H, 6.51; N, 7.93. Found: C, 52.08; H, 6.46; N, 8.13.

Example 27

1-[2(R)-Amino-3-mercaptopropyl]-4-(1-naphthoyl)-2(S)-(4-acetamidobutyl)piperazine dihydrochloride Step A 1-Benzyl-3(S)-(4-tert-butoxycarbonylaminobutyl)piperazine-2,5-dione The title compound was prepared according to the procedure described for 1-benzyl-3(S)-methylpiperazine-2,5-dione. Thus N,N' bis-tert-butoxycarbonyl lysine (8.71 g, 0.025 mol), dicyclohexylcarbodiimide in methylene chloride (0.5M) (0.025 mol, 0.050 mL) and ethyl N-benzylglycinate (4.70 mL, 0.025 mol) gave the N-benzylglycinate as a clear gum. This product was taken up in methylene chloride (60 mL) and trifluoroacetic acid (30 mL) added. After 1 h the solvents were evaporated and the residue dissolved in saturated sodium bicarbonate. This was evaporated and the residue dissolved in dimethylformamide (100 mL). Di-tert-butyl dicarbonate (6.23 g, 0.027 mol) was added and the reaction stirred at 20° C. for 12 h. The dimethylformamide was distilled in vacuo and the residue chromatographed on silica gel with 2.5% methanol in chloroform. The title compound was obtained as a gum (5.37 g). NMR (300 MHz, CDCl$_3$) d 7.30 (5H, m), 6.92 (1H, br s), 4.68 (1H, br s,), 4.60 (2H, q, J=7 Hz), 4.07 (1H, br s), 3.84 (2H, AB q, J=20 Hz, Δu 25 Hz), 3.10 (2H, m), 1.91 (2H, m), 1.5 (4H,m) 1.43 (9H, s).

Step B

4-Benzyl-2(S)-(4-aminobutyl)piperazine-2,5-dione hydrochloride

The product from Step A (5.37 g, 14.32 mmol) was dissolved in methylene chloride (150 mL). Hydrogen chloride was passed through the solution for 2 h at 20° C. The solution was degassed with nitrogen, and the solvent removed in vacuo. The title compound was obtained as a white solid (4.24 g). NMR (300 MHz, DMSO-d$_6$) d 8.37 (1H, s), 7.90 (3H, br s), 7.30 (5H, m), 4.52 (2H, AB q), 3.94 (1H, br s), 3.90 (1H, d, J=22 Hz), 3.74 (1H, d, J=22 Hz), 2.75 (2H, br s), 1.73 (2H, m), 1.55 (2H, m), 1.35 (2H, m).

Step C

4-Benzyl-1-tert-butoxycarbonyl-2(S)-(4-tert-butoxycarbonyl-aminobutyl)piperazine The title compound was prepared according to the procedure described in Example 1, Step B except using 4-benzyl-2(S)-(4-aminobutyl)piperazine-2,5-dione hydrochloride (3.41 g, 10.94 mmol) was added slowly portionwise to a slurry of lithium aluminum hydride (2.3 g, 61.30 mmol) in tetrahydrofuran (80 mL). After refluxing, the product was isolated as described and treated with di-tert-butyl dicarbonate (5.72 g, 26.0 mmol). The crude product was purified by column chromatography on silica gel, eluting with 30% ethyl acetate in hexane. The title compound was obtained as a gum (3.74 g). NMR (300 MHz, CDCl$_3$) d 7.30 (5H, m), 4.52 (1H, br s,), 4.02 (1H, br s), 3.84 (1H, br s), 3.53 (1H, d, J=14 Hz), 3.36 (1H, d, J=14 Hz), 3.35 (3H, m), 2.74 (1H, br d, J=12 Hz), 2.64 (1H, d, J=12 Hz), 2.04 (2H, m), 1.82 (1H, m), 1.62 (1H, m), 1.49 (2H, m) 1.44 (18H, s), 1.19 (2H, m).

Step D 1-tert-Butoxycarbonyl-2(S)-(4-tert-butoxycarbonyl-aminobutyl)piperazine

The title compound was prepared according to the procedure described in Example 2, Step C except using 4-benzyl-1-tert-butoxycarbonyl-2(S)-(4-tert-butoxycarbonylaminobutyl)-piperazine (3.74 g, 8.36 mmol), 10% palladium on carbon (0.50 g) in methanol (50 mL) for 48 h at 60 psi hydrogen. The title compound ($R_f$ 0.3 in 5% methanol in chloroform) was obtained as an oil (3.14 g). NMR (300 MHz, CDCl$_3$) d 4.59 (1H, m), 4.00 (1H, m), 3.83 (1H, br d J=12 Hz), 3.12 (2H, m), 2.90 (4H, m), 2.70 (1H, dt, J=4, 13 Hz), 1.0–1.9 (25H, m).

Step E 1-tert-Butoxycarbonyl-2(S)-(4-tert-butoxycarbonylaminobutyl-4-naphthoyl)piperazine The product from Step D (3.1 g, 8.3 mmol) was converted to the title compound according to the procedure described in Example 1, Step A using naphthalene-1-carboxylic acid (2.15 g, 12.5 mmol), HOBT (1.12 g, 8.36 mmol), EDC.HCl (1.91 g, 10.0 mmol) and triethylamine to adjust the pH to 7. The title compound was obtained as a foam (3.1 g).

Step F

3(S)-(4-Aminobutyl)-1-naphthoyl)piperazine

The product of Step E (2.64 g, 5.16 mmol) was dissolved in methanol at 0° C., and hydrogen chloride bubbled through this solution. After 2 h, the solution was purged with nitrogen, and the methanol was evaporated. The residue was twice more treated with methanol, which was evaporated. The title compound was obtained as a yellow foam (2.01 g).

Step G

3(S)-(4-Acetamidobutyl)-1(-1-naphthoyl)piperazine

The product of Step F (0.300 g, 0.78 mmol) was dissolved in pyridine (10 mL) and acetic anhydride (0.074 mL, 0.78 mmol) and triethylamine (0.327 mL, 2.34 mmol) added. After 3 h, additional acetic anhydride was added (0.025 mL) and the reaction stirred overnight. The solvents were removed in vacuo and the residue chromatographed on silica gel with 1.5% methanol in chloroform. The title compound was isolated as an oil (0.185 g).

Step H

1-(2(R)-tert-Butoxycarbonylamino-3-triphenylmethylthiopropyl)-2(S)-(4-acetamidobutyl)-4-(1-naphthoylpiperazine dihydrochloride The title compound was obtained from the product of Step G essentially according to the procedure described in Example 1, Step D except using dichloroethane as solvent. 2(S)-(4-Acetamidobutyl)-4-naphthoylpiperazine (0.180 g, 0.51 mmol), sodium triacetoxyborohydride (0.430 g, 2.04 mmol), crushed molecular sieves (0.5 g), and 2(R)-N-tert-butoxy-carbonylamino-3-triphenylmethylthiopropanal (0.250 g, 0.560 mmol) in dichloroethane (7 mL) at pH 5.5 gave the title compound (0.410 g).

Step I

1-(2(R)-Amino-3-mercaptopropyl)-2(S)-(4-acetamidobutyl)-4-(1-naphthoyl)piperazine dihydrochloride The product of Step H (0.410 g, 0.52 mmol) was converted to the title compound according to the procedure described for Step E, Example 1 using triethylsilane (0.310 mL, 2.04 mmol) and trifluoroacetic acid (5 mL) in methylene chloride (5 mL). Purification by preparative HPLC (gradient elution: 85% Solvent A to 60% Solvent A/40% Solvent B, 40 min) and ion exchange provided the title compound as a white powder (0.042 g). FAB ms m/e 443 (m+1).

Analysis calculated for $C_{24}H_{34}N_4O_2S.3.9$ HCl.1.3 $H_2O$: C, 47.46; H, 6.72; N; 9.22. Found: C, 47.51, H, 6.72, N, 9.21.

Example 28

1-(2(R)-Amino-3-mercaptopropyl)-4-(1-naphthoyl)-homopiperazine dihyhdrochloride

Step A

4-(1-Naphthoyl)homopiperazine

Homopiperazine (0.60 g, 6.0 mmol), naphthalene carboxylic acid (0.51 g, 3.0 mmol), 1-hydroxybenzotriazole (0.45 g, 3 mmol) and 1-ethyl-3-(3-dimethylaminopropyl)carbodiimide hydrochloride (EDC.HCl) (0.63 g, 3.3 mmol) were added to dry, degassed dimethylformamide (7 mL). The pH of the reaction was adjusted to 7 with triethylamine, and the reaction stirred overnight. The dimethylformamide was distilled in vacuo, and the residue partitioned between ethyl acetate and water. The organic phase was washed with water and saturated sodium chloride solution, and dried over magnesium sulfate. The crude product was chromatographed on silica gel using chloroform/methanol as eluant and the title compound was isolated (0.100 g). NMR (CDCl$_3$, 300 MHz) d 7.88 (2H, m), 7.50 (3H, m), 7.27 (1H, m), 4.08 (1H, m), 3.81 (1H, m), 3.28 (2H, m), 3.18 (1H, m), 3.00 (1H, m), 2.92 (1H, t, J=7 Hz), 2.72 (1H, t, J=7 Hz), 2.20 (1H, m), 1.58 (1H, m).

Step B

1-(2(R)-tert-Butoxycarbonylamino-3-triphenylmethylthiopropyl)-4-(1-naphthoyl)-homopiperazine The title compound was obtained from the product of Step A essentially according to the procedure described in Example 1, Step D except using dichloroethane as solvent. 4-Naphthoylhomopiperazine (0.100 g, 0.39 mmol), sodium triacetoxyborohydride (0.33 g, 1.6 mmol), crushed molecular sieves (0.5 g), and 2(R)-N-tert-butoxycarbonylamino-3-triphenylmethylthiopropanal (0.194 g, 0.433 mmol) in dichloroethane (15 mL) at pH 5.5 gave the title compound (0.260 g).

Step C

1-(2(R)-Amino-3-mercaptopropyl)-4-(1-naphthoyl) homopiperazine dihydrochloride The product of Step B (0.260 g, 0.379 mmol) was converted to the title compound according to the procedure described for Step E, Example 1 using triethylsilane (0.236 mL, 1.51 mmol) and trifluoroacetic acid (5 mL) in methylene chloride (5 mL). Purification by preparative HPLC (gradient elution: 95% Solvent A to 50% Solvent A/50% Solvent B, 40 min) and ion exchange provided the title compound as a white powder (0.074 g). FAB ms m/e 344 (m+1).

Analysis calculated for $C_{19}H_{25}N_3OS.2.3$ HCl.2.6 $H_2O$: C, 48.14; H, 6.91; N; 8.86. Found: C, 48.10, H, 6.88, N, 8.90.

Example 29

1-[2(R)-Amino-3-mercaptopropyl]-4-naphthoyl-2(S)-(2-cyclopropylmethylsulfonylethyl)piperazine dihydrochloride

Step A

1-tert-Butoxycarbonyl-2(S)-(2-thioacetylethyl)-4-(1-naphthoyl)piperazine

Triphenylphosphine (0.65 g, 2.5 mmol), in tetrahydrofuran (7 mL) was cooled to 0° C. and diethylazodicarboxylate (0.41 mL, 2.5 mmol) added. The reaction was stirred for 30 min, and 1-tert-butoxycarbonyl-2(S)-(2-hydroxyethyl)-4-naphthoylpiperazine (0.50 g, 1.3 mmol) and thiolacetic acid (0.18 mL, 2.5 mmol) were added in tetrahydrofuran (8 mL). After stirring at 20° C. for 16 h, the solvent was removed in vacuo and the residue chromatographed on silica with 30% ethyl acetate in hexane to give the title compound.

Step B

1-tert-Butoxycarbonyl-2(S)-(2-cyclopropylmethylthioethyl-4-1-naphthoyl) piperazine The product from Step A was dissolved in methanol (13 mL) and the solution saturated with ammonia at 0° C. When the reaction was complete, the solvent was removed in vacuo and replaced with dry degassed dimethylformamide. The solution was cooled to 0° C. and cyclopropylmethyl bromide (0.118 mL, 1.22 mmol) and sodium hydride (0.54 g, 2.2 mmol) added. When the reaction was complete by tlc, water was added to the reaction and dimethylformamide removed in vacuo. The residue was partitioned between ethyl acetate and 2% potassium hydrogen sulfate; the ethyl acetate was washed with brine and dried over magnesium sulfate. The crude product was chromatographed on silica gel with 5% methanol in chloroform to give the title compound.

Step C

1-tert-Butoxycarbonyl-2(S)-(2-cyclopropylmethylsulfonylethyl)-4-(1-naphthoyl) piperazine The product from Step B (0.25 g, 0.55 mmol) was dissolved in methanol (15 mL) and a solution of magnesium monoperoxyphthalic acid (0.816 g, 1.65 mmol) in methanol added at 0° C. When the reaction was complete by tlc, 10% aqueous sodium thiosulfate was added and stirred for 30 min. The methanol was removed in vacuo and the residue partitioned between ethyl acetate and saturated sodium bicarbonate. The organic phase was washed with brine and dried over magnesium sulfate. Filtration and evaporation gave the title compound.

Step D 1-(2(R)-tert-Butoxycarbonylamino-3-triphenylmethylthiopropyl)-4-(1-naphthoyl)-2(S)-(2-cyclopropylmethylsulfonylethyl)-4-piperazine The product of Step C (0.240 g, 0.490 mmol) was converted to the title compound according to the procedure described in Example 1, Step D. Thus 1-tert-butoxycarbonyl-2(S)-(2-cyclopropylmethylsulfonyl-ethyl)-4-(1-naphthoyl)piperazine was stirred with trifluoroacetic acid (5 mL) and methylene chloride (10 mL) for 1 h. The free base (0.060 g, 0.155 mmol) was reacted with 2(R)-N-tert-butoxy-carbonylamino-3-triphenyl-methylthiopropanal (0.263 g, 0.588 mmol), sodium triacetoxyborohydride (0.155 g, 0.727 mmol), crushed molecular sieves (0.120 g) in dichloroethane (10 mL) at pH 5.5. The crude product was chromatographed on silica gel with 30–60% ethyl acetate in hexane to give the title compound.

Step E 1-(2(R)-Amino-3-mercaptopropyl)-4-(1-naphthoyl)-2(S)-(2-cyclopropylmethylsulfonylethyl)carboxy-4-piperazine dihydrochloride The product of Step D (0.132 g, 0.161 mmol) was converted to the title compound according to the procedure described for Step E, Example 1 using triethylsilane (0.50 mL, 3.1 mmol) and trifluoroacetic acid (4 mL) in methylene chloride (8 mL). Purification by preparative HPLC (gradient elution: 80% Solvent A to 30% Solvent A/70% Solvent B, 30 min) and ion exchange provided the title compound as a white powder (0.020 g). FAB ms m/e 476 (m+1).

Analysis calculated for $C_{24}H_{33}N_3O_3S_3 \cdot 2.0$ TFA·0.4 $H_2O$: C, 47.31; H, 5.08; N; 5.91. Found: C, 47.28; H, 5.05, N, 6.15.

Example 30

1-(2(R)-Amino-3-mercaptopropyl)-4-(1-naphthoyl)-2(S)-piperidylcarboxyl-4-piperazine dihydrochloride Step A 1-Benzyl-3(S)-benzyloxymethylpiperazine-2,5-dione The title compound was prepared according to the procedure described in Example 2, Step A, except using O-benzyl Boc-L-serine (10 g, 33.8 mmol), dicyclohexylcarbodiimide in methylene chloride (0.5M) (68 mL, 34.0 mmol) and ethyl N-benzylglycinate (6.34 mL, 34.0 mmol). After deprotection with hydrogen chloride in dichloromethane (200 mL), neutralization, and recrystallization of the crude product from ethyl acetate, the title compound was obtained as a white solid (10.3 g). NMR (300 MHz, $CDCl_3$) δ 7.58 (10H, m), 6.41 (1H, br s), 4.74 (1H, d, J=15 Hz), 4.53 (2H, AB q, J=12 Hz, Δv=20 Hz), 4.45 (1H, d, J=15 Hz), 4.22 (1H, m), 3.92 (1H, d, J=17 Hz), 3.88 (1H, dd, J=8, 10 Hz), 3.81 (1H, dd, J=6, 10 Hz), 3.75 (1H, d, J=17 Hz).

Step B

4-Benzyl-1-tert-butoxycarbonyl-2(S)-benzyloxymethylpiperazine

The title compound was prepared according to the procedure described in Example 2, Step B, except using 1-benzyl-3(S)-benzyloxy-methylpiperazine-2,5-dione (19.3 g, 59.5 mmol), lithium aluminum hydride (8.82 g, 0.232 mol), in THF (400 mL). The reduction product was treated with di-tert-butyl dicarbonate (16.0 g, 73.3 mmol). After column chromatography on silica gel, eluting with 10% ethyl acetate in hexane, the title compound was obtained as an oil (17.1 g). NMR (300 MHz, $CDCl_3$) δ 7.25 (10H, m), 4.50 (2H, AB q, J=12 Hz, Δv=20 Hz), 4.25 (1H, br s), 3.85 (1H, br s), 3.78 (1H, t, J=9 Hz), 3.60 (1H, br s), 3.48 (2H, AB q, J=13 Hz, Δv=25 Hz), 3.01 (1H, m), 3.96 (1H, d, J=9 Hz), 2.72 (1H, d, J=9 Hz), 2.09 (1H, dd, J=4, 9 Hz), 2.02 (1H, dt, J=3, 12 Hz), 1.44 (9H, s).

Step C 1-tert-Butoxycarbonyl-2(S)-hydroxymethylpiperazine

The product from Step B (17.1 g, 43.1 mmol) in methanol (100 mL) was hydrogenated at 60 psi in the presence of 10% Pd/C (6 g) for 2d. The catalyst was filtered and 3.0 g of product further hydrogenated at 60 psi in MeOH and in the presence of 10% Pd/C (2.4 g) and acetic acid (1.8 mL) for 4d. The catalyst was filtered and the product dissolved in ethyl acetate. Solid sodium bicarbonate was added and then filtered from the mixture. The title compound was obtained (1.8 g). NMR (300 MHz, $CDCl_3$) δ 3.95 (4H, m), 3.28 (1H, dd, J=2, 15 Hz), 3.19 (1H, d, J=15 Hz), 2.98 (1H, d, J=15 Hz), 2.90 (1H, dd J=4, 15 Hz), 2.72 (1H, td, J=4, 15 Hz), 2.52 (1H, br s), 1.45 (9H, s).

Step D 1-tert-Butoxycarbonyl-2(S)-hydroxymethyl-4-(1-naphthoyl)-piperazine

The title compound was obtained from the product of Step C (1.81 g, 8.40 mmol) and 1-hydroxybenzotriazole (1.29 g, 3 mmol), 1-ethyl-3-(3-dimethylaminopropyl)carbodiimide hydrochloride (EDC.HCl) (1.76 g, 9.21 mmol) in dimethylformamide (7 mL). The pH of the reaction was adjusted to 7 with triethylamine, and the reaction stirred 3h. The dimethylformamide was distilled in vacuo, and the residue partitioned between ethyl acetate and water. The organic phase was washed with water and saturated sodium chloride solution, and dried over magnesium sulfate. The crude product was chromatographed on silica gel using 40% ethyl acetate in hexane as eluant, and the title compound was isolated as a white solid (1.64 g).

Step E 1-tert-Butoxycarbonyl-4-(1-naphthoyl)-piperazine-2(S)-carboxylic acid

The product of Step B (1.64 g, 4.43 mmol) was dissolved in dimethylformamide (10 mL) and pyridinium dichromate added (5.83 g, 15.5 mmol). The reaction was stirred at 20° C. overnight. The solvent was removed in vacuo and the residue partitioned between ethyl acetate and 1% aqueous potassium hydrogen sulfate. The organic phase was washed with water and saturated sodium chloride solution, then dried over magnesium sulfate. The title compound was obtained as a white foam (1.12 g).

Step F 1-tert-Butoxycarbonyl-4-(1-naphthoyl)-2(S)-piperidylcarboxypiperazine

The product of Step E (0.150 g, 0.39 mmol) was reacted with piperidine (0.046 L, 0.468 mmol), 1-ethyl-3-(3-dimethylaminopropyl)-carbodiimide hydrochloride (0.082 g, 0.429), 1-hydroxybenzotriazole (0.060 g, 0.390 mmol) in dimethylformamide (5 mL) at pH 7 overnight. The dimethylformamide was removed in vacuo and the residue partitioned between ethyl acetate and 2% potassium hydrogen sulfate. The organic phase was washed with water and saturated brine, and dried over magnesium sulfate. The title compound was obtained as an oil (0.130 g).

Step G

1-(2(R)-tert-Butoxycarbonylamino-3-triphenylmethylthiopropyl)-4-(1-naphthoyl)-2(S)-piperidylcarboxyl-4-piperazine The product of Step F (0.190 g, 0.421 mmol) was converted to the title compound according to the procedure described in Example 1, Step D, using trifluoroacetic acid (5 mL) and methylene chloride (5 mL), followed by sodium triacetoxyborohydride (0.356 g, 1.68 mmol), crushed molecular sieves (0.5 g), and 2(R)-N-tert-butoxycarbonylamino-3-triphenylmethylthiopropanal (0.226 g, 0.505 mmol) in dichloroethane (10 mL) at pH 5.5. The crude product was chromatographed on silica gel with 2% methanol in chloroform, and gave the title compound as a foam (0.195 g).

Step H

1-(2(R)-Amino-3-mercaptopropyl)-4-(1-naphthoyl)-2(S)-piperidylcarboxy-4-piperazine dihydrochloride The product of Step G (0.195 g, 0.487 mmol) was converted to the title compound according to the procedure described for Step E, Example 1 using triethylsilane (0.259 mL, 1.68 mmol) and trifluoroacetic acid (10 mL) in methylene chloride (10 mL). Purification by preparative HPLC (gradient elution: 85% Solvent A to 65% Solvent A/35% Solvent B, 40 min) and ion exchange provided the title compound as a white powder (0.063 g). FAB ms m/e 441 (m+1).

Analysis calculated for $C_{24}H_{32}N_4O_2S.3.4$ HCl.0.5 $H_2O$: C, 50.31; H, 6.40; N; 9.78. Found: C, 50.35; H, 6.56, N, 9.63.

Example 31

Methyl 4-(2(R)-amino-3-mercaptopropyl)-1-(1-naphthylmethyl)piperazine-2-carboxylate hydrochloride Step A

Methyl 1-Benzyloxycarbonyl-4-tert-butoxycarbonyl-piperazine-2-carboxylate

1-Benzyloxycarbonyl-4-tert-butoxycarbonyl-piperazine-2-carboxylic acid (4.76 g, 13.0 mmol) (prepared as described by C. F. Bigge, S. J. Hays, P. M. Novak, J. T. Drummond, G. Johnson, T. P. Bobovski in Tetrahedron Letters, Vol. 30, 5193–5196, 1989) was dissolved in 10% methanol in benzene. A solution of trimethylsilyldiazomethane in hexane (8 mL, 2M) was added dropwise. After 10 min, glacial acetic acid (1 mL) was added. When gas evolution ceased, the solvents were removed in vacuo, and the residue partitioned between ethyl acetate and saturated sodium bicarbonate. The organic phase was washed with saturated brine and dried over magnesium sulfate. The crude product was chromatographed on silica gel with 15% ethyl acetate in hexane, then recrystallized from ethyl acetate/hexane to obtain the title compound as a white powder (1.8 g).

Step B

Methyl 4-tert-butoxycarbonylpiperazine-2-carboxylate

A solution of the product from step A in methanol was hydrogenated at 60 psi in the presence of 10% Pd/C (0.250 g) for 24h. The catalyst was filtered and the methanol evaporated to yield the title compound as an oil (0.91 g).

Step C

Methyl 4-tert-butoxycarbonyl-1-(1-naphthylmethyl)-piperazine-2-carboxylate

The product from Step B was dissolved in methanol (20 mL) with naphthalene-1-carboxaldehyde (0.67 mL, 4.7 mmol), sodium cyanoborohydride (0.350 g, 5.6 mmol) at pH 6 (adjusted with acetic acid) and the reaction stirred overnight. The solvent was evaporated and the residue partitioned between ethyl acetate and saturated sodium bicarbonate. The organic phase was washed with saturated sodium chloride solution and dried over magnesium sulfate. The crude product was chromatographed on silica gel with ethyl acetate in hexane, and the title compound isolated as an oil. NMR ($CDCl_3$, 300 MHz) d 8.34 (1H, d, J=7 Hz), 7.85 (1H, dm, J=7 Hz), 7.79 (1H, m), 7.51 (2H, m), 7.39 (2H, m), 4.34 (1H, d, J=12 Hz), 3.98 (1H, br s), 3.91 (1H, dd, J=12, 6 Hz), 3.75 (3H, s), 3.60 (1H, br s), 3.44 (1H, d, J=12 Hz), 3.27 (1H, t, J=3 Hz), 3.19 (1H, d, J=12 Hz), 3.09 (1H, td, J=10, 3 Hz), 2.42 (1H, br s), 1.44 (9H, s).

Step D

Methyl 1-(2(R)-tert-butoxycarbonylamino-3-triphenylmethyl-thiopropyl)-4-(1-naphthyl-methyl) piperazine-2-carboxylate The product from Step C was converted to the title compound using the procedure described in Example 1, Step D. Thus methyl 4-tert-butoxycarbonyl-1-(1-naphthylmethyl) piperazine-2-carboxylate (0.536 g, 1.39 mmol) was deprotected with trifluoroacetic acid (3 mL) in dichloromethane (6 mL). The crude trifluoroacetate salt was reacted with sodium triacetoxyborohydride (0.356 g, 1.68 mmol), crushed molecular sieves (0.5 g), and 2(R)-N-tert-butoxycarbonylamino-3-triphenylmethylthiopropanal (0.226 g, 0.505 mmol) in dichloroethane (10 mL) at pH 5.5. The crude product was chromatographed on silica gel with 15% ethyl acetate in hexane. The title compound was obtained as a foam (0.977 g). FAB ms m/e 716 (m+1).

Step E

Methyl 1-(2(R)-Amino-3-mercaptopropyl)-4-(1-naphthylmethyl)piperazine-2-carboxylate hydrochloride The title compound was obtained according to the procedure described in Example 1, Step E except using methyl 1-(2(R)-tert-butoxycarbonylamino-3-triphenylmethylthiopropyl)-4-(1-naphthylmethyl)-piperazine-2-carboxylate (0.274 g, 0.383 mmol), triethylsilane (0.24 mL, 1.53 mmol) trifluoroacetic acid (5 mL) in dichloromethane (10 mL). The crude product was purified by HPLC by gradient elution (100% Solvent A to 50% Solvent A/50Solvent B over 60 min. After ion exchange, the title compound was obtained as a white solid. FAB ms m/e 374 (m+1).

Analysis calculated for $C_{20}H_{27}N_3O_2S.HCl.0.7$ $H_2O$: C, 56.85; H, 7.01; N; 9.94. Found: C, 56.80; H, 6.75, N, 9.98.

Example 32

In vitro inhibition of ras farnesyl transferase

Farnesyl-protein transferase (FPTase) from bovine brain was chromatographed on DEAE-Sephacel (Pharmacia, 0–0.8M NaCl gradient elution), N-octyl agarose (Sigma, 0–0.6M NaCl gradient elution), and a mono Q HPLC column (Pharmacia, 0–0.3M NaCl gradient). Ras-CVLS at 3.5 µM, 0.25 µM [$^3$H]FPP, and the indicated compounds were incubated with either a partially purified bovine enzyme preparation or a recombinant human enzyme preparation. The FPTase data presented below in Table 1 reflects the ability of the test compound to inhibit RAS farnesylation in vitro, as described in Pompliano, et al., Biochemistry 31, 3800 (1992).

TABLE 1

Inhibition of RAS farnesylation by compounds of this invention*

| Compound | IC$_{50}$ (nM)* |
| --- | --- |
| Example 3‡ | 6 nM |
| Example 6 | 4 nM |
| Example 7 | 11 nM |
| Example 8 | 11 nM |
| Example 12 | 5 nM |
| Example 13 | 3 nM |
| Example 14 | 1 nM |
| Example 15 | 6 nM |
| Example 16 | 2 nM |
| Example 17 | 6 nM |
| Example 18 | 1 nM |
| Example 19 | 5 nM |
| Example 20 | 1.6 nM |
| Example 21 | 1 nM |
| Example 27 | 3.5 nM |
| Example 28 | 21 nM |
| Example 30 | 3 nM |
| Example 31 | 2.9 nM |

*(IC$_{50}$ is the concentration of the test compound which gives 50% inhibition of FPTase under the described assay conditions)
‡(R,S) Diastereomer Example 33

In vivo ras farnesylation assay

The cell line used in this assay was the v-ras line, which expressed viral Ha-ras p21. The assay was performed essentially as described in DeClue, J. E. et. al., Cancer Research 51,712–717, (1991). Cells in 10 cm dishes at 50–75% confluency were treated with the test compound (final concentration of solvent, methanol or dimethyl sulfoxide, was 0.1%). After 4 hours at 37° C., the cells were labelled in 3 ml methionine-free DMEM supplemeted with 10% regular DMEM, 2% fetal bovine serum and 400 µCi[$^{35}$S]methionine (1000 Ci/mmol). After an additional 20 hours, the cells were lysed in 1 ml lysis buffer (1% NP40/20 mM HEPES, pH 7.5/5 mM MgCl$_2$/1 mM DTT/10 µg/ml aprotinen/2 µg/ml leupeptin/2 µg/ml antipain/0.5 mM PMSF) and the lysates cleared by centrifugation at 100.000×g for 45 min. Aliquots of lysates containing equal numbers of acid-precipitable counts were bought to 1 ml with IP buffer (lysis buffer lacking DTT) and immunoprecipitated with the ras-specific monoclonal antibody Y13-259 (Furth, M. E. et. al., J. Virol. 43, 294–304, (1982)). Following a 2 hour antibody incubation at 4° C., 200 µl of a 25% suspension of protein A-Sepharose coated with rabbit anti rat IgG was added for 45 min. The immunoprecipitates were washed four times with IP buffer (20 nM HEPES, pH 7.5/1 mM EDTA/1% Triton X-100.0.5% deoxycholate/0.1%/SDS/0.1M NaCl) boiled in SDS-PAGE sample buffer and loaded on 13% acrylamide gels. When the dye front reached the bottom, the gel was fixed, soaked in Enlightening, dried and autoradiographed. The intensities of the bands corresponding to farnesylated and nonfarnesylated ras proteins were compared to determine the percent inhibition of farnesyl transfer to protein. Data for representative test compounds are tabulated in Table 2.

TABLE 2

Inhibition of Ras Farnesylation by the compounds of this invention in the v-ras cell line

| Compound | IC$_{50}$ (µM) |
| --- | --- |
| Example 3‡ | 5 µM |
| Example 6 | 0.5–1 µM |
| Example 7 | 0.5–1 µM |
| Example 8 | 0.5–1 µM |
| Example 12 | 0.5 µM |
| Example 13 | 0.5 µM |
| Example 16 | 0.5 µM |
| Example 17 | 0.5 µM |
| Example 19 | 1 µM |
| Example 27 | 0.5 µM |
| Example 28 | 10 µM |
| Example 30 | 0.5 µM |
| Example 31 | 10 µM |

‡(R,S) Diastereomer

Example 34

Tables 3 and 4 show other compounds of the instant invention that were prepared by the procedures described in Examples 1–31. These compounds are meant to be illustrative and are not meant to be limiting.

TABLE 3

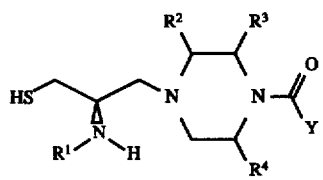

| Y | R$^1$ | R$^2$ | R$^3$ | R$^4$ | Formula | C, H, N |
| --- | --- | --- | --- | --- | --- | --- |
| 2,6-(CH$_3$)$_2$-phenyl | H | (S) C$_2$H$_5$ | H | H | C$_{18}$H$_{29}$N$_3$OS.2.95HCl | C, 48.82; H, 7.29; N, 9.35 |

TABLE 3-continued

| Y | R¹ | R² | R³ | R⁴ | Formula | C, H, N |
|---|----|----|----|----|---------|---------|
| 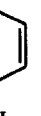 | H | (S) n-C₃H₇ | H | H | $C_{19}H_{31}N_3OS \cdot 2.9\,HCl \cdot 1H_2O$ | C, 48.24; H, 7.66; N, 8.89 |
|  | H | (S) i-C₃H₇ | H | H | $C_{19}H_{31}N_3OS \cdot 2.4HCl \cdot 0.4H_2O$ | C, 51.43; H, 7.73; N, 9.48 |
|  | H | (S) i-C₄H₉ | H | H | $C_{20}H_{33}N_3OS \cdot 2HCl \cdot 1.0H_2O$ | C, 52.85; H, 8.15; N, 9.48 |
|  | H | (R) n-C₄H₉ | H | H | $C_{20}H_{33}N_3OS \cdot 2HCl \cdot 1.0H_2O$ | C, 50.22; H, 8.79; N, 8.83 |
|  | H | (S) n-C₄H₉ | H | H | $C_{19}H_{35}N_3OS \cdot 2.7HCl$ | C, 47.34; H, 6.76; N, 8.65 |
|  | H | (S) 2(S)-C₄H₉ | H | H | $C_{20}H_{33}N_3OS \cdot 2.1HCl$ | C, 54.73; H, 8.02; N, 9.23 |
| 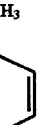 | H | (S) n-C₄H₉ | H | (S) CH₃ | $C_{21}H_{35}N_3OS \cdot 2HCl \cdot 1.8H_2O$ | C, 51.98; H, 7.89; N, 8.72 |
|  | PhCH₂ | (S) n-C₄H₉ | H | H | $C_{27}H_{39}N_3OS \cdot 2.65HCl \cdot 0.2H_2O$ | C, 58.58; H, 7.66; N, 7.45 |
|  | H | (S) n-C₄H₉ | H | H | $C_{20}H_{30}N_4O_2S \cdot 2.4HCl \cdot 1.8H_2O$ | C, 48.77; H, 6.99; N, 11.22 |

TABLE 3-continued

| Y | R¹ | R² | R³ | R⁴ | Formula | C, H, N |
|---|---|---|---|---|---|---|
| 1-methylindol-3-yl | H | (S) n-$C_4H_9$ | H | H | $C_{20}H_{32}N_4O_2S \cdot 2.25HCl \cdot 0.1H_2O$ | C, 52.21; H, 7.56; N, 12.34 |
| naphthalen-1-yl | H | (S) $PhCH_2OCH_2$ | H | H | $C_{26}H_{31}N_3O_2S \cdot 2.2HCl \cdot 0.3H_2O$ | C, 58.32; H, 6.35; N, 8.04 |
| 2,3-dimethylphenyl | H | (S) $CON(C_2H_5)_2$ | H | H | $C_{21}H_{34}N_4O_2S \cdot 0.95H_2O \cdot 2.65CF_3CO_2H$ | C, 43.52; H, 5.32; N, 8.06 |
| phenyl | H | H | H | H | $C_{14}H_{21}N_3OS \cdot 2.8HCl \cdot 1.8H_2O$ | C, 40.65; H, 6.67; N, 9.91 |
| furan-2-yl | H | H | H | H | $C_{12}H_{19}N_3O_2S \cdot 2.9HCl \cdot 2.8H_2O$ | C, 33.840; H, 6.50; N, 9.86 |
| 2,3-dichlorophenyl | H | (S) n-$C_4H_9$ | H | H | $C_{14}H_{19}N_3S \cdot 2.8HCl \cdot 2.03H_2O$ | C, 36.06; H, 5.13; N, 8.81 |
| furan-3-yl | H | H | H | H | $C_{12}H_{19}N_3O_2S \cdot 2.9HCl \cdot 1.9H_2O$ | C, 35.19; H, 6.33; N, 10.29 |
| 3-chloro-4-methylthien-2-yl | H | H | H | H | $C_{13}H_{20}ClN_3OS_2 \cdot 2.4HCl \cdot 1.1H_2O$ | C, 35.38; H, 5.60; N, 9.59 |
| thien-2-yl | H | H | H | H | $C_{12}H_{19}N_3OS_2 \cdot 2.9HCl \cdot 1.2H_2O$ | C, 34.95; H, 5.94; N, 9.99 |
| 1-methyl-2,3-dihydroindol-? | H | H | H | H | $C_{16}H_{24}N_4OS \cdot 3.5HCl \cdot 0.8H_2O$ | C, 41.67; H, 6.37; N, 11.97 |

TABLE 3-continued

| Y | R¹ | R² | R³ | R⁴ | Formula | C, H, N |
|---|---|---|---|---|---|---|
| indole (N-linked) | H | H | H | H | $C_{16}H_{22}N_4OS \cdot 2.7HCl \cdot 1.5H_2O$ | C, 45.11; H, 6.10; N, 13.02 |
| 2,3-dimethylphenyl | H | (S) $CH_2CH_2N(CH_3)_2$ | H | H | $C_{20}H_{34}N_4OS \cdot 3.9HCl \cdot 0.1H_2O$ | C, 46.00; H, 7.36; N, 10.42 |
| 2,3-dimethylphenyl | H | (S) $C_2H_5OCH_2CH_2$ | H | H | $C_{20}H_{33}N_3O_2S \cdot 2.7HCl \cdot 0.4H_2O$ | C, 49.57; H, 7.58; N, 8.93 |
| 2,3-dimethylphenyl | H | (S) $PhCH_2OCH_2$ | H | H | $C_{24}H_{33}N_3O_2S \cdot 2.0HCl$ | C, 58.50; H, 7.17; N, 8.44 |
| 2,3-dimethylphenyl | H | (S) $C_2H_5OCH_2$ | H | H | $C_{19}H_{31}N_3O_2S \cdot 2.4HCl \cdot 0.6H_2O$ | C, 49.28; H, 7.52; N, 9.24 |
| 2,3-dimethylphenyl | H | (S) $n-C_3H_7OCH_2CH_2$ | H | H | $C_{21}H_{35}N_3O_2S \cdot 3.1HCl \cdot 1.0H_2O$ | C, 48.13; H, 7.41; N, 8.04 |
| 4-quinolyl | H | (S) $n-C_4H_9$ | H | H | $C_{21}H_{30}N_4OS \cdot 3.7HCl$ | C, 48.44; H, 6.22; N, 10.28 |
| 7-methyl-2,3-dihydrobenzofuranyl | H | (S) $PhCH_2OCH_2$ | H | H | $C_{24}H_{31}N_3O_3S \cdot 2.4HCl \cdot 0.4H_2O$ | C, 53.76; H, 6.32; N, 7.92 |
| 7-methyl-2,3-dihydrobenzofuranyl | H | (S) $CH_3OCH_2CH_2$ | H | H | $C_{19}H_{29}N_3O_3S \cdot 3.2HCl \cdot 0.9H_2O$ | C, 44.50; H, 6.47; N, 8.48 |

TABLE 3-continued

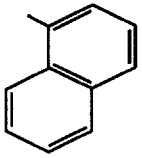

| Y | R¹ | R² | R³ | R⁴ | Formula | C, H, N |
|---|---|---|---|---|---|---|
| 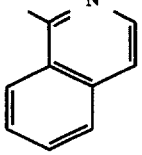 | H | (S) HOCH₂CH₂ | H | H | $C_{20}H_{27}N_3O_2S \cdot 3.3HCl \cdot 1.3H_2O$ | C, 46.56; H, 6.41; N, 8.43 |
| 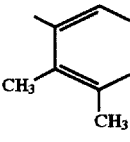 | H | (S) n-C₄H₉ | H | H | $C_{21}H_{30}N_4OS \cdot 4.0HCl \cdot 2.4H_2O$ | C, 43.93; H, 6.80; N, 9.62 |
| 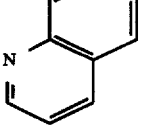 | H | (S) n-C₃H₇OCH₂ | H | H | $C_{20}H_{33}N_3O_2S \cdot 3.6HCl$ | C, 47.16; H, 7.25; N, 8.22 |
| 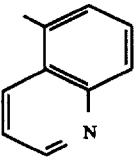 | H | (S) CH₃OCH₂CH₂ | H | H | $C_{22}H_{35}N_4O_2S \cdot 4.2HCl \cdot 1.3H_2O$ | C, 43.60; H, 6.41; N, 9.74 |
| 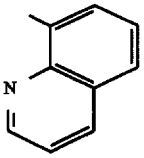 | H | (S) n-C₄H₉ | H | H | $C_{21}H_{30}N_4OS \cdot 3.5HCl \cdot 0.9H_2O$ | C, 47.59; H, 6.99; N, 10.25 |
| 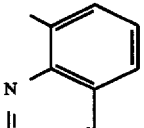 | H | (S) CH₃OCH₂CH₂ | H | H | $C_{20}H_{28}N_4O_2S \cdot 3.6HCl \cdot 0.8H_2O$ | C, 45.01; H, 6.29; N, 10.36 |
| 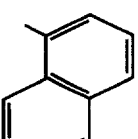 | H | (S) C₂H₅OCH₂CH₂CH₂ | H | H | $C_{22}H_{32}N_4O_2S \cdot 3.6HCl \cdot 0.2H_2O$ | C, 48.00; H, 6.57; N, 10.00 |
|  | H | (S) C₂H₅OCH₂CH₂CH₂ | H | H | $C_{22}H_{33}N_3O_2S \cdot 2.6HCl$ | C, 54.09; H, 6.86; N, 8.10 |

TABLE 3-continued

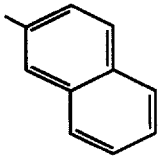

| Y | R¹ | R² | R³ | R⁴ | Formula | C, H, N |
|---|----|----|----|----|---------|---------|
| 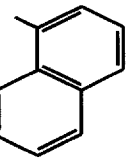 | H | (S) n-$C_4H_9$ | H | H | $C_{22}H_{31}N_3OS \cdot 2.65 \cdot 0.8H_2O$ HCl | C, 53.28; H, 7.16; N, 8.56 |
| 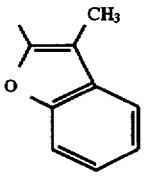 | H | (R) CONH-t-$C_4H_9$ | H | H | $C_{23}H_{32}N_4O_2S \cdot 2.6HCl \cdot 0.4H_2O$ | C, 52.03; H, 6.75; N, 10.66 |
| 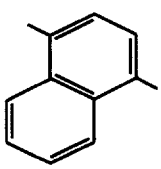 | H | (S) n-$C_4H_9$ | H | H | $C_{21}H_{31}N_3O_2S \cdot 2.7HCl \cdot 0.25H_2O$ | C, 51.29; H, 7.01; N, 8.57 |
| 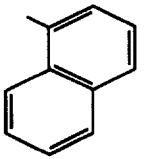 | H | (S) $CH_3OCH_2CH_2$ | H | H | $C_{21}H_{28}FN_3O_2S \cdot 2.75CF_3CO_2H$ | C, 44.28; H, 4.30; N, 5.86 |
|  | H | (S) 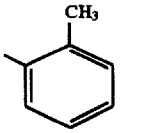—$CH_2OCH_2CH_2$ | H | H | $C_{24}H_{35}N_3O_2S \cdot 3.5HCl \cdot 0.7H_2O$ | C, 50.77; H, 6.76; N, 7.42 |
| 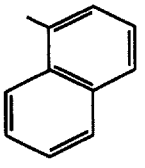 | H | (S) $CH_3CH_2CH_2CH_2$ | H | H | $C_{19}H_{31}N_3OS \cdot 2.25CF_3CO_2H$ | C, 46.59; H, 5.56; N, 6.90 |
|  | H | (S) —$CH_2NH$—C(O)$CH_3$ | H | H | $C_{23}H_{30}N_4O_2S \cdot 3.3HCl \cdot 1.3H_2O$ | C, 52.15; H, 6.59; N, 10.35 |
| 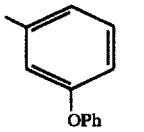 | H | (S) $CH_3OCH_2CH_2$ | H | H | $C_{23}H_{31}N_3O_3S \cdot 2.8HCl \cdot 0.9H_2O$ | C, 50.50; H, 6.55; N, 7.86 |

TABLE 3-continued

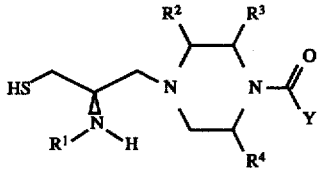

| Y | R¹ | R² | R³ | R⁴ | Formula | C, H, N |
|---|----|----|----|----|---------|---------|
| 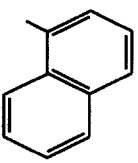 | H | (S) —CH₂SO₂CH₂CH₂ | H | H | $C_{24}H_{33}N_3O_3S_2 \cdot 2CF_3CO_2H \cdot 0.3H_2O$ | C, 47.28; H, 5.05; H, 6.15 |
| 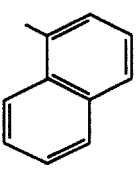 | H | (S) (n-C₃H₇)₂N—C(=O)— | H | H | $C_{25}H_{36}N_4O_2S \cdot 2.0HCl$ | C, 57.43; H, 7.53; N, 10.57 |
|  | H | (S) CH₃OCH₂CH₂ | H | H | $C_{20}H_{30}N_4O_2S \cdot 2.7CF_3CO_2H \cdot 0.2H_2O$ | C, 43.43; H, 4.74; N, 8.03 |
| 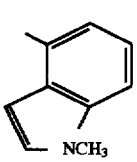 | H | (S) CH₃CH₂CH₂CH₂ | H | H | $C_{19}H_{31}N_3OS \cdot 2.3CF_3CO_2H \cdot 0.1H_2O$ | C, 46.20; H, 5.52; N, 6.88 |
| 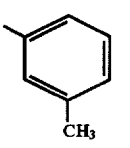 | H | (S) CH₃CH₂CH₂CH₃ | H | H | $C_{18}H_{29}N_3O_2S \cdot 2.25CF_3CO_2H \cdot 0.85H_2O$ | C, 44.46; H, 5.47; N, 7.31 |
| 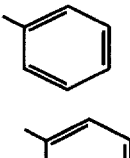 | H | (S) CH₃CH₂OCH₂CH₂ | H | H | $C_{22}H_{31}N_3O_2S \cdot 2.9HCl \cdot 0.4H_2O$ | C, 51.40; H, 6.81; N, 8.12 |
| 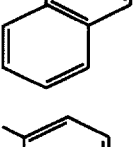 | H | (S) CH₃OCH₂CH₂ | H | H | $C_{19}H_{33}N_4O_2S \cdot 4.9HCl \cdot 1.3H_2O$ | C, 39.20; H, 6.84; N, 10.36 |
| 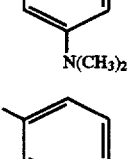 | H | (S) CH₃OCH₂CH₂ | H | H | $C_{18}H_{29}N_3O_3S \cdot 3.4HCl \cdot 1.7H_2O$ | C, 41.38; H, 6.92; N, 9.36 |
| 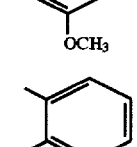 | H | (S) HO——CH₂ | H | H | $C_{25}H_{29}FN_3O_2S \cdot 1.35HCl \cdot 0.3H_2O$ | C, 61.29; H, 6.37; N, 8.52 |

TABLE 3-continued

| Y | R¹ | R² | R³ | R⁴ | Formula | C, H, N |
|---|---|---|---|---|---|---|
| 1-methyl-tetrahydronaphthalene | H | (S) CH₃OCH₂CH₂ | H | H | $C_{21}H_{33}N_3O_2S \cdot 2.9CF_3CO_2H \cdot 1.1H_2O$ | C, 43.34; H, 5.19; N, 5.83 |
| 1-methyl-naphthalene | H | (S) NH₂CH₂CH₂CH₂CH₂ | H | H | $C_{22}H_{32}N_4OS \cdot 3.5HCl \cdot 1.7H_2O$ | C, 47.25; H, 7.01; N, 10.06 |
| 3-methyl-benzothiophene | H | (S) CH₃OCH₂CH₂ | H | H | $C_{19}H_{27}N_3O_2S_2 \cdot 1.4HCl \cdot 0.2H_2O$ | C, 43.91; H, 5.98; N, 8.18 |
| 1-methyl-naphthalene | H | (S) dansyl-NH(CH₂)₃CH₂ (5-(CH₃)₂N-naphthalene-1-SO₂NH(CH₂)₃CH₂) | H | H | $C_{34}H_{43}N_5O_3S \cdot 4.9HCl \cdot 0.1H_2O$ | C, 52.25; H, 7.34; N, 8.81 |
| 1-methyl-tetrahydronaphthalene | H | (S) CH₃OCH₂CH₂ | H | H | $C_{21}H_{33}N_3O_2S \cdot 2.8HCl \cdot 0.2H_2O$ | C, 50.67; H, 7.34; N, 8.81 |
| 3-methyl-indole | H | (S) CH₃OCH₂CH₂ | H | H | $C_{19}H_{28}N_4O_2S \cdot 2.6HCl \cdot 0.7H_2O$ | C, 47.11; H, 6.64; N, 11.71 |
| 2-OC₂H₅-1-methyl-naphthalene | H | (S) CH₃OCH₂CH₂ | H | H | $C_{23}H_{33}N_3O_3S \cdot 2.6CF_3CO_2H \cdot 0.6H_2O$ | C, 46.48; H, 4.94; N, 5.79 |
| 1-methyl-naphthalene | H | (S) PhCH₂NHC(O)CH₂ | H | H | $C_{25}H_{36}N_4O_2S \cdot 2.0HCl$ | C, 59.05; H, 6.09; N, 10.46 |

TABLE 3-continued
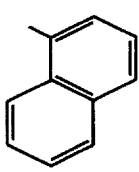
| Y | R¹ | R² | R³ | R⁴ | Formula | C, H, N |
|---|---|---|---|---|---|---|
| 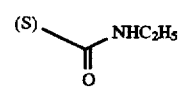 | H | (S) 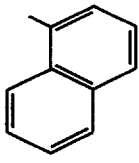 NHC₂H₅ | H | H | $C_{21}H_{28}N_4O_2S \cdot 2.4HCl \cdot 1.7H_2O$ | C, 48.62; H, 6.58; N, 10.65 |
| 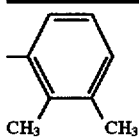 | H | (S) n-C₃H₇SO₂CH₂CH₂ | H | H | $C_{23}H_{33}N_3O_3S \cdot 2.8HCl \cdot 0.3H_2O$ | C, 48.46; H, 6.41; N, 7.32 |
TABLE 4
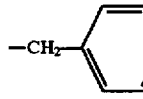
| Z | R¹ | R² | R³ | R⁴ | Formula | C, H, N |
|---|---|---|---|---|---|---|
| 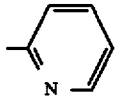 | H | H | H | H | $C_{15}H_{25}N_3S \cdot 3HCl \cdot 1H_2O$ | C, 44.10; H, 7.28; N, 10.45 |
| —CH₂—  | H | H | H | H | $C_{14}H_{23}N_3S \cdot 3HCl \cdot 0.5H_2O \cdot 0.25TFA$ | C, 42.10; H, 6.66; N, 10.31 |
| 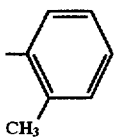 | H | H | H | H | $C_{12}H_{20}N_4S \cdot 4HCl \cdot 1.5H_2O$ | C, 33.93; H, 6.30; N, 13.16 |
|  | H | H | H | H | $C_{13}H_{21}N_3S \cdot 3.35HCl \cdot 0.4H_2O$ | C, 41.04; H, 6.66; N, 11.07 |
|  | H | H | H | H | $C_{14}H_{23}N_3S \cdot 3.45HCl \cdot 0.2H_2O$ | C, 42.60; H, 6.87; N, 11.23 |

TABLE 4-continued

[Structure: HS-CH2-C(=N-R1,H with NH)-CH2-N(piperazine with R2, R3 on one carbon, R4 on another, N-Z)]

| Z | R¹ | R² | R³ | R⁴ | Formula | C, H, N |
|---|----|----|----|----|---------|---------|
| —CH₂—(2,3-dichlorophenyl) | H | H | H | H | C₁₄H₂₁Cl₂N₃S.3HCl.0.45H₂O.0.2TFA | C, 36.43; H, 5.31; N, 8.98 |
| —SO₂—(phenyl) | H | H | H | H | C₁₃H₂₁N₃O₂S₂.2HCl.0.95H₂O | C, 38.31; H, 6.01; N, 10.45 |
| 3-methylphenyl | H | H | H | H | C₁₄H₂₃N₃S.3HCl | C, 45.67; H, 7.46; N, 11.37 |
| 4-methylphenyl | H | H | H | H | C₁₄H₂₃N₃S.3.7HCl.1H₂O | C, 40.20; H, 6.94; N, 11.30 |
| 3-ethylphenyl | H | H | H | H | C₁₅H₂₅N₃S.3HCl.1H₂O | C, 43.97; H, 6.97; N, 10.18 |
| 5,6,7,8-tetrahydronaphth-1-yl | H | H | H | H | C₁₇H₂₇N₃S.3HCl | C, 49.28; H, 7.26; N, 10.09 |
| —CH₂—(2,6-dimethylphenyl) | H | H | H | H | C₂₀H₃₅N₃S.3HCl | C, 48.59; H, 7.90; N, 8.48 |
| —SO₂—(naphth-1-yl) | H | (S)n-C₄H₉ | H | H | C₂₁H₃₁N₃O₂S₂.3HCl | C, 49.15; H, 6.55; N, 8.06 |
| —SO₂—(5-dimethylamino-naphth-1-yl) | H | (S)n-C₄H₉ | H | H | C₂₃H₃₆N₄O₂S₂.3.8HCl.0.5H₂O | C, 45.12; H, 6.71; N, 9.30 |

TABLE 4-continued

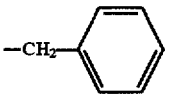

| Z | R¹ | R² | R³ | R⁴ | Formula | C, H, N |
|---|---|---|---|---|---|---|
| —CH₂—(phenyl) | H | (S)n-C₄H₉ | H | (S)CH₃ | $C_{19}H_{33}N_3S \cdot 3.0HCl \cdot 0.75H_2O$ | C, 49.80 H, 8.20; N, 9.20 |

What is claimed is:

1. A compound which inhibits farnesyl-protein transferase of the formula A:

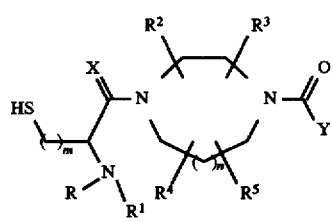

wherein:

X is O or $H_2$;
m is 1 or 2;
n is 0 or 1;
t is 1 to 4;
R and $R^1$ are independently selected from H, $C_{1-4}$ alkyl, or aralkyl; $R^2$, $R^3$, $R^4$, and $R^5$ are independently selected from: H; $C_{1-8}$ alkyl, alkenyl, alkynyl, aryl, heterocycle,

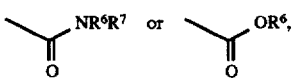

unsubstituted or substituted with one or more of 1) aryl or heterocycle, unsubstituted or substituted with:
   a. Cl 1-4 alkyl,
   b. $(CH_2)_tOR^6$,
   c. $(CH_2)_tNR^6R^7$,
   d. halogen,
2) $C_{3-6}$ cycloalkyl,
3) $OR^6$,
4) $SR^6$, $S(O)R^6$, $SO_2R^6$,
5) —$NR^6R^7$ 6) 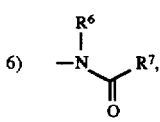

7) 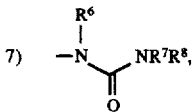

8) 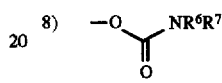

9) 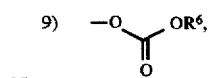

10) 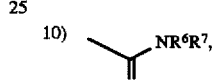

11) —$SO_2$—$NR^6R^7$,

12) 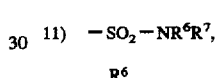

13) 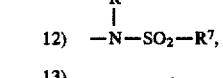

or

14) 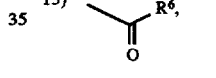

and any two of $R^2$, $R^3$, $R^4$, and $R^5$ are optionally attached to the same carbon atom;

Y is aryl, heterocycle, unsubstituted or substituted with one or more of:

1) $C_{1-4}$ alkyl, unsubstituted or substituted with:
   a. $C_{1-4}$ alkoxy,
   b. $NR^6R^7$,
   c. $C_{3-6}$ cycloalkyl,
   d. aryl or heterocycle,
   e. HO,
2) aryl or heterocycle,
3) halogen,
4) $OR^6$,
5) $NR^6R^7$,
6) CN,
7) $NO_2$, or
7) $CF_3$;

$R^6$, $R^7$ and $R^8$ are independently selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
   a) $C_{1-4}$ alkoxy,
   b) aryl or heterocycle, c) halogen,
d) HO, e) 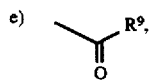

f) —SO$_2$R$^9$, or
g) NRR$^1$, wherein

R$^6$ and R$^7$ may be joined to form a piperidinyl ring;

R$^9$ is C$_{1-4}$ alkyl or aralkyl;

heteroaryl is independently selected from: benzimidazolyl, benzisoxazolyl, benzofurazanyl, benzofuryl, benzothiazolyl, benzothienyl, benzoxazolyl, furyl, imidazolyl, indolyl, isoquinolinyl, isothiazolyl, naphthyridinyl, pyridyl, pyrazinyl, pyrazolyl, pyrimidinyl, pyrrolyl, quinazolinyl, quinolinyl, thiazolyl, thienofuryl, thienothienyl, and thienyl; and heteroaroyl is —C(=O)-heteroaryl;

or a optical isomer, disulfide or pharmaceutically acceptable salt thereof.

2. A compound which inhibits farnesyl-protein transferase of the formula B:

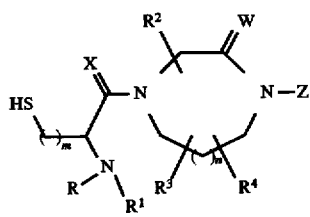 B wherein

X is O or H$_2$;
m is 1 or 2;
n is 0 or 1;
t is 1 to 4;

R and R$^1$ are independently selected from H, C$_{1-4}$ alkyl, or aralkyl; R$^2$, R$^3$ and R$^4$ are independently selected from: H; C$_{1-8}$ alkyl, alkenyl, alkynyl, aryl, heterocycle,

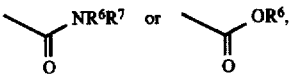

unsubstituted or substituted with one or more of 1) aryl or heterocycle, unsubstituted or substituted with:
  a. C$_{1-4}$ alkyl,
  b. (CH$_2$)$_r$OR$^6$,
  c. (CH$_2$)$_r$NR$^6$R$^7$,
  d. halogen,
2) C$_{3-6}$ cycloalkyl,
3) OR$^6$,
4) SR$^6$, S(O)R$^6$, SO$_2$R$^6$,
5) —NR$^6$R$^7$ 6) 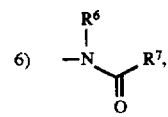

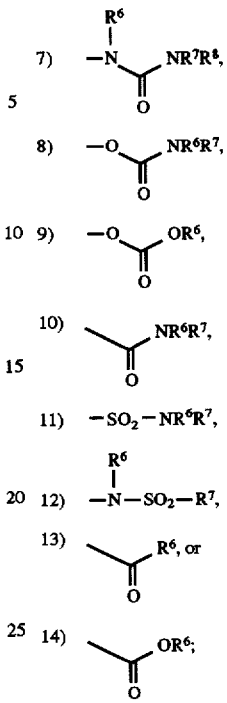

and any two of R$^2$, R$^3$ and R$^4$ are optionally attached to the same carbon atom;

and wherein the carbon adjacent to the C=W moiety is substituted by at least one non-hydrogen group;

W is H$_2$ or O;

Z is aryl, heteroaryl, arylmethyl, heteroarylmethyl, arylsulfonyl, heteroarylsulfonyl, unsubstituted or substituted with one or more of the following:

1) C$_{1-4}$ alkyl, unsubstituted or substituted with:
  a) C$_{1-4}$ alkoxy,
  b) NR$^6$R$^7$,
  c) C$_{3-6}$ cycloalkyl,
  d) aryl or heterocycle, or
  e) HO,
2) aryl or heterocycle,
3) halogen,
4) OR$^6$,
5) NR$^6$R$^7$,
6) CN,
7) NO$_2$, or
8) CF$_3$;

R$^6$, R$^7$ and R$^8$ are independently selected from: H; C$_{1-4}$ alkyl, C$_{3-6}$ cycloalkyl, heterocycle, aryl, aroyl, heteroaroyl, arylsulfonyl, heteroarylsulfonyl, unsubstituted or substituted with:
  a) C$_{1-4}$ alkoxy,
  b) aryl or heterocycle,
  c) halogen,
  d) HO, e) 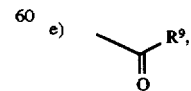

f) —SO R$^9$, or
g) NRR$^1$, wherein

R$^6$ and R$^7$ may be joined to form a piperidine ring, $R^9$ is $C_{1-4}$ alkyl or aralkyl;

heteroaryl is independently selected from: benzimidazolyl, benzisoxazolyl, benzofurazanyl, benzofuryl, benzothiazolyl, benzothienyl, benzoxazolyl, furyl, imidazolyl, indolyl, isoquinolinyl, isothiazolyl, naphthyridinyl, pyridyl, pyrazinyl, pyrazolyl, pyrimidinyl, pyrrolyl, quinazolinyl, quinolinyl, thiazolyl, thienofuryl, thienothienyl, and thienyl;

heteroaroyl is —C(═O)-heteroaryl;

or a optical isomer, disulfide or pharmaceutically acceptable salt thereof.

3. A compound which inhibits farnesyl-protein transferase of the formula C:

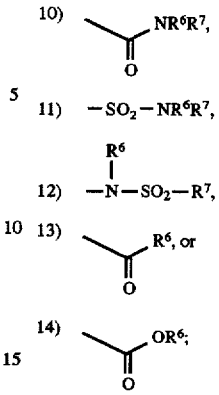

wherein

X is O or $H_2$;

m is 1 or 2;

n is 0 or 1;

t is 1 to 4;

R and $R^1$ are independently selected from H, $C_{1-4}$ alkyl, or aralkyl;

$R^2$, $R^3$ and $R^4$ are independently selected from: H; $C_{1-8}$ alkyl, alkenyl, alkynyl, aryl, heterocycle,

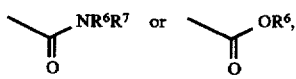

unsubstituted or substituted with one or more of 1) aryl or heterocycle, unsubstituted or substituted with:
  a. $C_{1-4}$ alkyl,
  b. $(CH_2)_tOR^6$,
  c. $(CH_2)_tNR^6R^7$,
  d. halogen,
  $C_{3-6}$ cycloalkyl,
  $OR^6$,
  $SR^6$, $S(O)R^6$, $SO_2R^6$,
5) —$NR^6R^7$

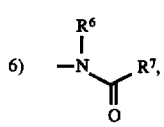

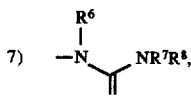

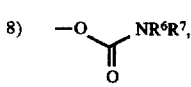

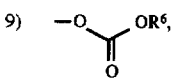

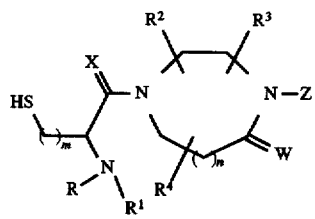

and any two of $R^2$, $R^3$ and $R^4$ are optionally attached to the same carbon atom;

and wherein the carbon adjacent to the C═W moiety is substituted by two hydrogens;

W is $H_2$ or O;

Z is aryl, heteroaryl, arylmethyl, heteroarylmethyl, arylsulfonyl, heteroarylsulfonyl, unsubstituted or substituted with one or more of the following:

1) $C_{1-4}$ alkyl, unsubstituted or substituted with:
  a. $C_{1-4}$ alkoxy,
  b. $NR^6R^7$,
  c. $C_{3-6}$ cycloalkyl,
  d. aryl or heterocycle, or
  e. HO,
2) aryl or heterocycle,
3) halogen,
4) $OR^6$,
5) $NR^6R^7$,
6) CN,
7) $NO_2$, or
8) $CF_3$;

$R^6$, $R^7$ and $R^8$ are independently selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
  a) $C_{1-4}$ alkoxy,
  b) aryl or heterocycle,
  c) halogen,
  d) HO,

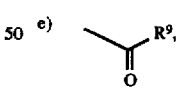

f) —$SO_2R^9$, or
g) $NRR^1$, wherein $R^6$ and $R^7$ may be joined to form a piperidinyl ring, $R^9$ is $C_{1-4}$ alkyl or aralkyl;

heteroaryl is independently selected from: benzimidazolyl, benzisoxazolyl, benzofurazanyl, benzofuryl, benzothiazolyl, benzothienyl, benzoxazolyl, furyl, imidazolyl, indolyl, isoquinolinyl, isothiazolyl, naphthyridinyl, pyridyl, pyrazinyl, pyrazolyl, pyrimidinyl, pyrrolyl, quinazolinyl, quinolinyl, thiazolyl, thienofuryl, thienothienyl, and thienyl; and heteroaroyl is —C(═O)-heteroaryl;

or a optical isomer, disulfide or pharmaceutically acceptable salt thereof.

4. The compound according to claim 1 of the formula A:

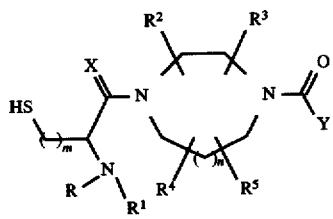

wherein
X is $H_2$;
m is 1;
n is 0;
R, $R^1$, $R^3$, $R^4$, $R^5$ is H or $CH_3$;
$R^2$ is H; $C_{1-5}$ alkyl,

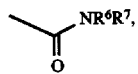

unbranched or branched, unsubstituted or substituted with one or more of
1) aryl,
2) heterocycle,
3) $OR^6$,
4) $SR^6$, $SO_2R^6$, or 5) 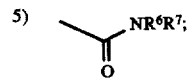

and any two of $R^2$, $R^3$, $R^4$, and $R^5$ are optionally attached to the same carbon atom;
Y is aryl, heterocycle, unsubstituted or substituted with one or more of:
a) $C_{1-4}$ alkyl,
b) $C_{1-4}$ alkoxy,
c) halogen, or
d) $NR^6R^7$;
$R^6$, $R^7$ is independently selected from H; $C_{1-4}$ alkyl, $C_{3-6}$ cycloalkyl, aryl, heterocycle, unsubstituted or substituted with:
a) $C_{1-4}$ alkoxy,
b) halogen, or
c) aryl or heterocycle;
or a optical isomer, disulfide or pharmaceutically acceptable salt thereof.

5. The compound according to claim 1 of the formula A:

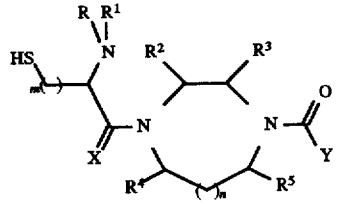

wherein
X is $H_2$;
m is 1;
n is 0;
R, $R^1$, $R^3$, $R^4$, $R^5$ is H;
$R^2$ is $C_{1-4}$ alkyl, unsubstituted or substituted with one or more of:

1) phenyl,
2) pyridyl,
3) $OR^6$, or
4) $SR^6$, $SO_2R^6$;
Y is Dihydrobenzofuryl, isoquinolinyl, naphthyl, quinolinyl, phenyl, unsubstituted or substituted with one or more of:
a) $C_{1-3}$ alkyl,
b) $C_{1-3}$ alkoxy, or
c) F, Cl;
$R^6$ is
1) $C_{1-4}$ alkyl unsubstituted or substituted with:
a. phenyl,
b. pyridyl,
c. $C_{1-3}$ alkoxy,
1) phenyl, or
3) pyridyl;
or a optical isomer, disulfide or pharmaceutically acceptable salt thereof.

6. A compound which inhibits farnesyl-protein transferase which is:

1-[2-(R)-Amino-3-mercaptopropyl]-2(S)-(1-butyl)-4-(2,3-dimethylbenzoyl)piperazine dihydrochloride

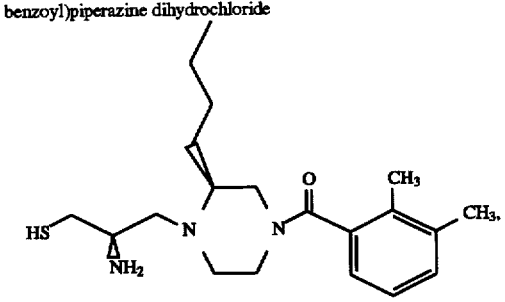

1-[2(R)-Amino-3-mercaptopropyl]-2(S)-(n-butyl)-4-(1-naphthoyl)piperazine

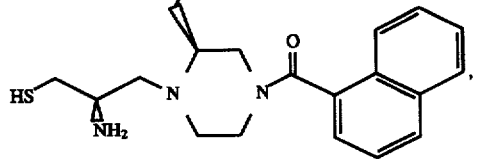

1-[2(R)-Amino-3-mercaptopropyl]-2(S)-benzyl-4-[1-(2,3-dimethyl)benzoyl]piperazine

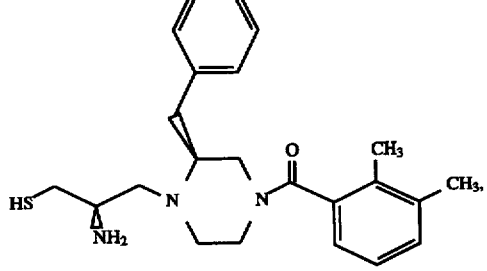

1-[2(R)-Amino-3-mercaptopropyl]-2(S)-(2-methoxy)ethyl-4-[1-(2,3-dimethyl)benzoyl]piperazine

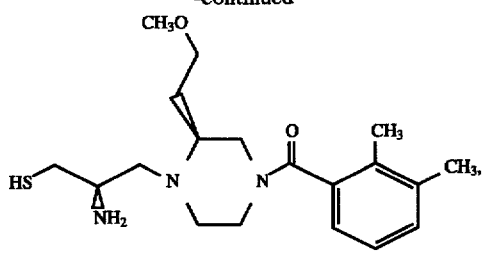

1-[2(R)-Amino-3-mercaptopropyl]-2(S)-(2-methylthio)ethyl-4-[1-(2,3-dimethyl)benzoyl]piperazine

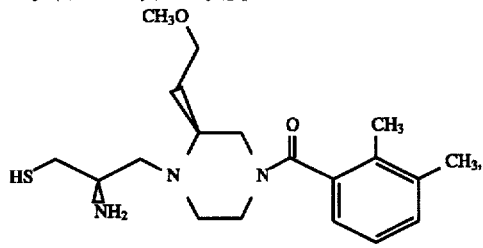

1-[2(R)-Amino-3-mercaptopropyl]-2(S)-(n-butyl)-4[(7-2,3-dihydrobenzofuroyl)]piperazine

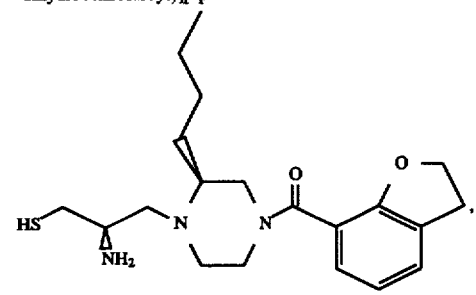

1-(2(R)-Amino-3-mercaptopropyl)-4-(1-naphthoyl)-2(S)-pyridinylcarboxyl-4-piperazine dihydrochloride

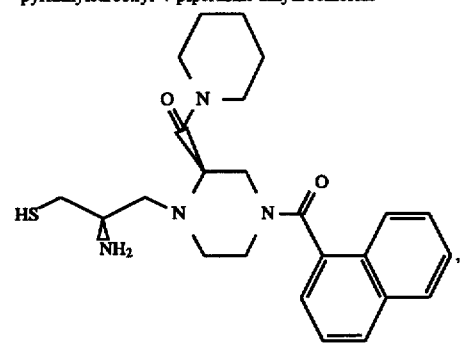

Methyl 4-(2(R)-amino-3-mercaptopropyl)-1-(1-naphthyl-methyl)piperazine-2-carboxylate hydrochloride

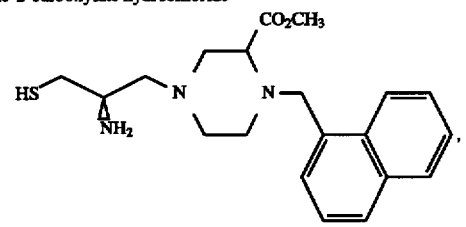

1-[2(R)-Amino-3-mercaptopropyl]-2(S)-(2-methoxyethyl)-4-(1-naphthoyl)piperazine

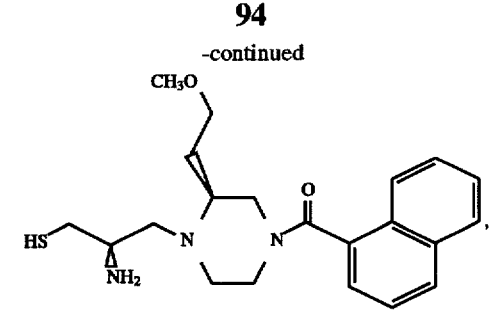

1-[2(R)-Amino-3-mercaptopropyl]-2(S)-n-butyl-4-(8-quinolinylcarbonyl)piperazine

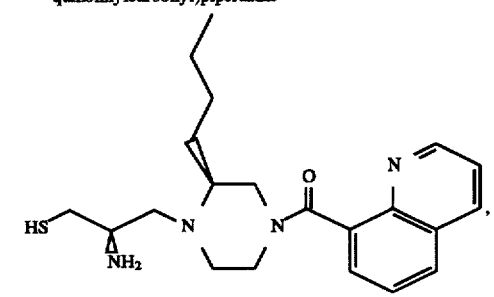

1-[2(R)-Amino-3-mercaptopropyl]-2(S)-(2-(1-propoxy)ethyl)-4-(1-naphthoyl)piperazine

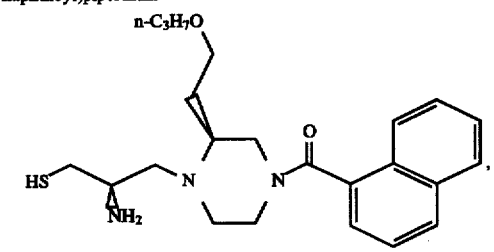

1-[2(R)-Amino-3-mercaptopropyl]-2(S)-(3-methoxy-1-propyl)-4-(1-naphthoyl)piperazine

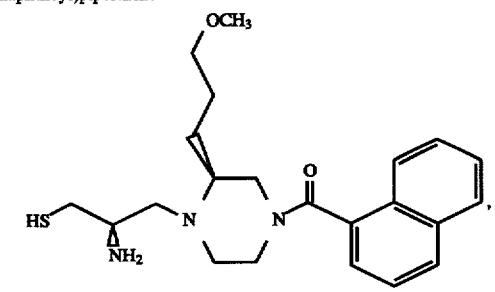

1-[2(R)-Amino-3-mercaptopropyl]-2(S)-(2-(1-propoxy)ethyl)-4-(8-quinolinoyl)piperazine

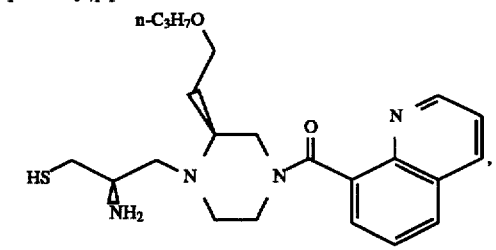

1-[2(R)-Amino-3-mercaptopropyl]-2(S)-[(3-pyridyl)methoxyethyl)]-4-(1-naphthoyl)piperazine -continued

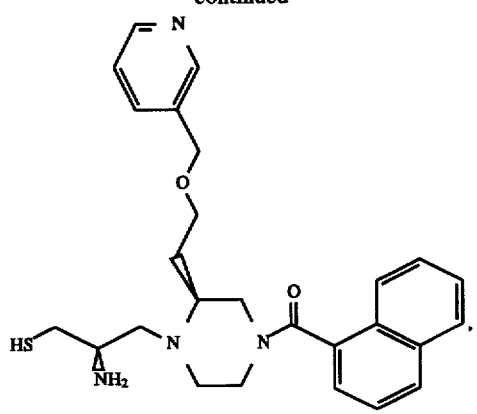

1-[2(R)-Amino-3-mercaptopropyl]-4-naphthoyl-2(S)-(2-phenylsulfonyl-ethyl)piperazine dihydrochloride

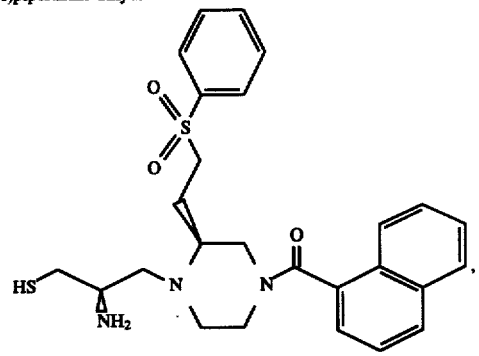

bis-1,1'-[2(R)-Amino-3-(2(S)-(2-methoxyethyl)-4-naphthoyl-1-piperazinyl)]propyl disulfide tetrahydrochloride

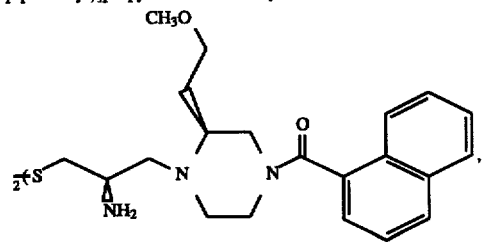

bis-1,1'-[2(R)-Amino-3-(4-naphthoyl-2(S)-(2-phenylsulfonyl-ethyl)-1-piperazinyl)]propyl disulfide tetrahydrochloride

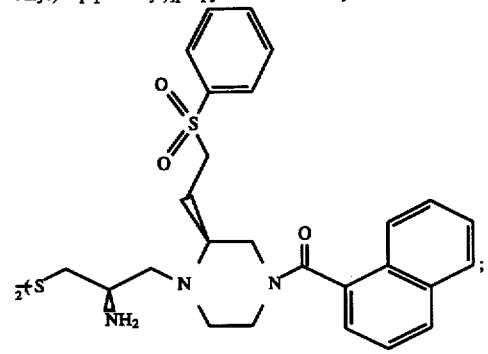

or

1-[2(R)-Amino-3-mercaptopropyl]-4-(1-naphthoyl)-2(S)-(4-acetamidobutyl)piperazine dihydrochloride -continued

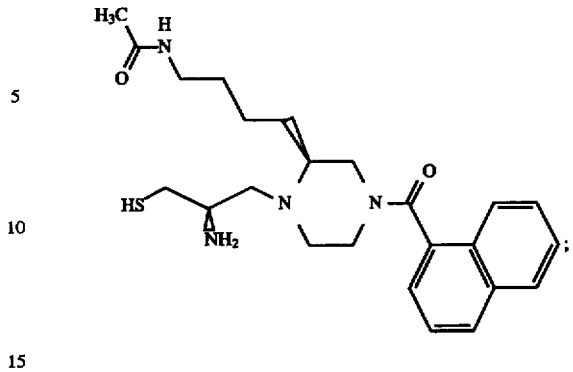

or a pharmaceutically acceptable salt thereof.

7. The compound of claim 6 which is:

1-[2(R)-Amino-3-mercaptopropyl]-2(S)-[(3-pyridyl)methoxyethyl)]-4-(1-naphthoyl)piperazine

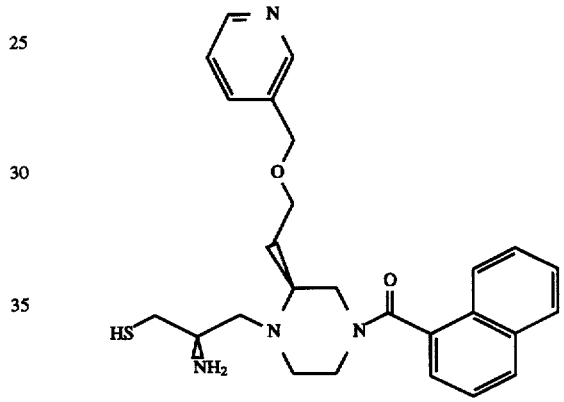

or a pharmaceutically acceptable salt thereof.

8. The compound of claim 6 which is:

1-[2(R)-Amino-3-mercaptopropyl]-2(S)-(2-methoxyethyl)-4-(1-naphthoyl)piperazine

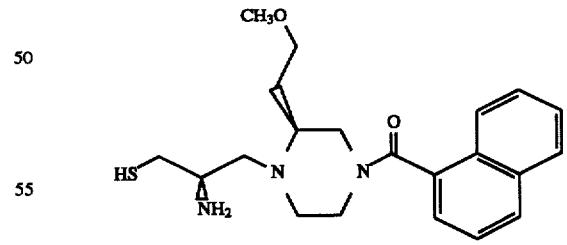

or a pharmaceutically acceptable salt thereof.

9. The compound of claim 6 which is:

1-[2(R)-Amino-3-mercaptopropyl]-2(S)-(2-(1-propoxy)ethyl)-4-(1-naphthoyl)piperazine -continued

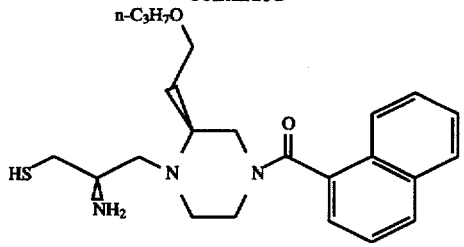

or a pharmaceutically acceptable salt thereof.

10. The compound of claim 6 which is:

1-[2(R)-Amino-3-mercaptopropyl]-4-naphthoyl-2(S)-(2-phenylsulfonylethyl)piperazine dihydrochloride

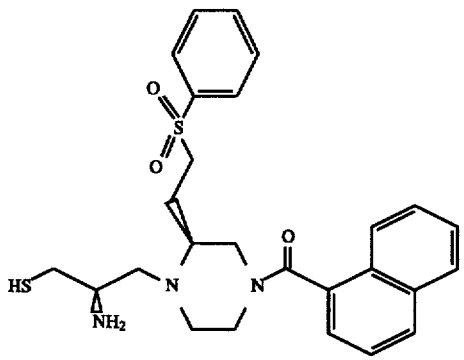

or a pharmaceutically acceptable salt thereof.

11. The compound of claim 6 which is:

bis-1,1'-[2(R)-Amino-3-(2(S)-(2-methoxyethyl)-4-naphthoyl-1-piperazinyl)]propyl disulfide tetrahydrochloride -continued

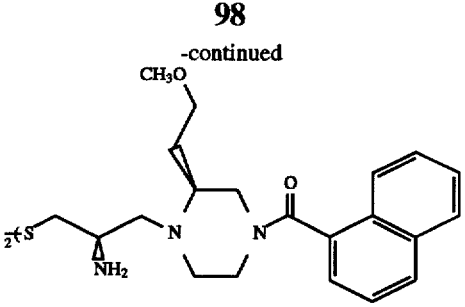

or a pharmaceutically acceptable salt thereof.

12. A pharmaceutical composition comprising a pharmaceutical carrier, and dispersed therein, a therapeutically effective amount of a compound of claim 1.

13. A pharmaceutical composition comprising a pharmaceutical carrier, and dispersed therein, a therapeutically effective amount of a compound of claim 2.

14. A pharmaceutical composition comprising a pharmaceutical carrier, and dispersed therein, a therapeutically effective amount of a compound of claim 3.

15. A pharmaceutical composition comprising a pharmaceutical carrier, and dispersed therein, a therapeutically effective amount of a compound of claim 6.

16. A method for inhibiting farnesyl-protein transferase which comprises administering to a mammal in need thereof a therapeutically effective amount of a composition of claim 12.

17. A method for inhibiting farnesyl-protein transferase which comprises administering to a mammal in need thereof a therapeutically effective amount of a composition of claim 13.

18. A method for inhibiting farnesyl-protein transferase which comprises administering to a mammal in need thereof a therapeutically effective amount of a composition of claim 14.

19. A method for inhibiting farnesyl-protein transferase which comprises administering to a mammal in need thereof a therapeutically effective amount of a composition of claim 15.

* * * * *

UNITED STATES PATENT AND TRADEMARK OFFICE
CERTIFICATE OF CORRECTION

PATENT NO. : 5,736,539
DATED : April 7, 1998
INVENTOR(S) : Graham, et. al.

It is certified that error appears in the above-identified patent and that said Letters Patent is hereby corrected as shown below:

In Column 85, line 48 should read:

a. $C_{1-4}$ alkyl

In Column 88, line 65 should read:

f) $SO_2R^9$, or

In Column 93, line 24-25 should read:

-- 1-[2(R)-Amino-3-mercaptopropyl]-2(S)-(n-butyl)-4-[7-(2,3-dihydrobenzofuroyl)] piperazine Signed and Sealed this Fifteenth Day of December, 1998

Attest:

BRUCE LEHMAN

*Attesting Officer*    *Commissioner of Patents and Trademarks*